(12) United States Patent
Diener et al.

(10) Patent No.: US 7,767,803 B2
(45) Date of Patent: Aug. 3, 2010

(54) STABILIZED APTAMERS TO PSMA AND THEIR USE AS PROSTATE CANCER THERAPEUTICS

(75) Inventors: John L. Diener, Cambridge, MA (US); Paul Hatala, Charlestown, MA (US); Jess Wagner-Whyte, Lynn, MA (US); Charles Wilson, Concord, MA (US)

(73) Assignee: Archemix Corp., Cambridge, MA (US)

( * ) Notice: Subject to any disclaimer, the term of this patent is extended or adjusted under 35 U.S.C. 154(b) by 945 days.

(21) Appl. No.: 11/370,491

(22) Filed: Mar. 7, 2006

(65) Prior Publication Data

US 2007/0041901 A1 Feb. 22, 2007

Related U.S. Application Data

(63) Continuation-in-part of application No. 10/826,077, filed on Apr. 15, 2004, now abandoned, which is a continuation-in-part of application No. 10/600,007, filed on Jun. 18, 2003, now abandoned.

(60) Provisional application No. 60/390,042, filed on Jun. 18, 2002, provisional application No. 60/660,514, filed on Mar. 7, 2005, provisional application No. 60/670,518, filed on Apr. 11, 2005.

(51) Int. Cl.
*A61K 21/00* (2006.01)

(52) U.S. Cl. .................. 536/24.5; 536/23.1; 435/6; 514/44

(58) Field of Classification Search .................. None
See application file for complete search history.

(56) References Cited

U.S. PATENT DOCUMENTS

| | | | |
|---|---|---|---|
| 3,710,795 A | 1/1973 | Higuchi et al. | 128/260 |
| 4,137,230 A | 1/1979 | Hashimoto et al. | 260/239.3 |
| 4,360,462 A | 11/1982 | Higashide et al. | 260/239.3 |
| 4,870,162 A | 9/1989 | Trouet et al. | 530/363 |
| 5,208,020 A | 5/1993 | Chari et al. | 424/85.91 |
| 5,262,564 A | 11/1993 | Kun et al. | 562/430 |
| 5,270,163 A | 12/1993 | Gold et al. | 435/6 |
| 5,475,096 A | 12/1995 | Gold et al. | 536/23.1 |
| 5,496,938 A | 3/1996 | Gold et al. | 536/22.1 |
| 5,567,588 A | 10/1996 | Gold et al. | 435/6 |
| 5,580,737 A | 12/1996 | Polisky et al. | 435/6 |
| 5,637,459 A | 6/1997 | Burke et al. | 435/6 |
| 5,648,214 A | 7/1997 | Nieuwlandt et al. | 435/6 |
| 5,660,985 A | 8/1997 | Pieken et al. | 435/6 |
| 5,672,695 A | 9/1997 | Eckstein et al. | 536/24.5 |
| 5,683,867 A | 11/1997 | Biesecker et al. | 435/6 |
| 5,698,687 A | 12/1997 | Eckstein et al. | 536/25.3 |
| 5,705,337 A | 1/1998 | Gold et al. | 435/6 |
| 5,707,796 A | 1/1998 | Gold et al. | 435/6 |
| 5,763,177 A | 6/1998 | Gold et al. | 435/6 |
| 5,817,635 A | 10/1998 | Eckstein et al. | 514/44 |
| 5,861,254 A | 1/1999 | Schneider et al. | 435/6 |
| 5,958,691 A | 9/1999 | Pieken et al. | 435/6 |
| 6,011,020 A | 1/2000 | Gold et al. | 514/44 |
| 6,051,698 A | 4/2000 | Janjic et al. | 536/24.31 |
| 6,107,090 A | 8/2000 | Bander | 435/344 |
| 6,333,410 B1 | 12/2001 | Chari | 540/456 |
| 6,933,114 B2 | 8/2005 | Lupold et al. | 435/6 |
| 2004/0022727 A1 | 2/2004 | Stanton et al. | 424/1.49 |
| 2004/0180360 A1 | 9/2004 | Wilson et al. | 435/6 |
| 2004/0197804 A1 | 10/2004 | Keefe et al. | 435/6 |
| 2004/0249130 A1 | 12/2004 | Stanton et al. | 530/350 |
| 2005/0037394 A1 | 2/2005 | Keefe et al. | 435/6 |
| 2006/0030535 A1 | 2/2006 | Healy et al. | 514/44 |

FOREIGN PATENT DOCUMENTS

| | | |
|---|---|---|
| WO | WO 92/07065 | 4/1992 |
| WO | WO 98/18480 | 5/1998 |

OTHER PUBLICATIONS

Brady et al., "Design and synthesis of a pro-drug of vinblastine targeted at treatment of prostate cancer with enhanced efficacy and reduced systemic toxicity", *J. Med. Chem.*, 45:4706-4715 (2002).
Colcher et al., "Effects of genetic engineering on the pharmacokinetics of antibodies", *Q. J. Nucl. Med.*, 43:132-139 (1999).
Cotton et al., "2'-O-methyl, 2'-O-ethyl oligoribonucleotides and phosphorothiate oligodeoxyribonucleotides as inhibitors of the in vitro U7 snRNP-dependent mRNA processing event", *Nucl. Acids Res.*, 19:2629-2635 (1991).
Eggen et al., "The Cryptophycins: Their Synthesis and Anticancer Activity", *Medical Research Reviews*, 22(2):85-101 (2002).
Farokhzad et al., "Nanoparticle-Aptamer Bioconjugates: A New Approach for Targetting Prostate Cancer Cells", *Cancer Research*, 64:7668-7672 (2004).
Froehler et al., "Synthesis of DNA via deoxynucleoside H-phosphonate intermediates", *Nucl. Acids Res.*, 14(13):5399-5407 (1986).
Froehler, B.C., "Deoxynucleoside H-Phosphonate Diester Intermediates in the Synthesis of Internucleotide Phosphate Analogues", *Tet. Letters*, 27(46):5575-5578 (1986).
Green et al., "Nuclease-resistant nucleic acid ligands to vascular permeability factor/vascular endothelial growth factor", *Chem. Biol.*, 2:683-695 (1995).
Greenwald et al., "Highly Water Soluble Taxol Derivatives: 7-Polyethylene Glycol Carbamates and Carbonates", *J. Org. Chem.*, 60:331-336 (1995).

(Continued)

*Primary Examiner*—J D Schultz
(74) *Attorney, Agent, or Firm*—Mintz, Levin, Cohn, Ferris, Glovsky and Popeo P.C.; Ivor R. Elrifi

(57) ABSTRACT

The present invention provides stabilized, high affinity nucleic acid ligands to PSMA. Methods for the identification and preparation of novel, stable, high affinity ligands to PSMA using the SELEX™ method with 2'-O-methyl substituted nucleic acids, and cell surface SELEX™ are described herein. Also included are methods and compositions for the treatment and diagnosis of disease characterized by PSMA expression, using the described nucleic acid ligands.

18 Claims, 15 Drawing Sheets

OTHER PUBLICATIONS

Hamann et al., "Gemtuzumab Ozogamicin, A Potent and Selective Anti-CD33 Antibody-Calicheamicin Conjugate for Treatment of Acute Myeloid Leukemia", *Bioconjugate Chem.*, 13:47-58 (2002).

Harris et al., "Effect of Pegylation on Pharmaceuticals", *Nat. Rev.*, 2:214-221 (2003).

Hicke et al., "Escort aptamers: a delivery service for diagnosis and therapy", *J. Clin. Invest.*, 106:923-928 (2000).

Hirose et al., "Rapid Synthesis of Trideoxyribonucleotide Blocks", *Tet. Letters*, 28:2449-2452 (1978).

Hobbs et al., "Polynucleotides containing 2'-amino-2'-deoxyribose and 2'-azido-2'-deoxyribose", *Biochem.*, 12(25):5138-5145 (1973).

Kupchan et al., "Structural Requirements for Antileukemic Activity among the Naturally Occuring and Semisynthetic Maytansinoids", *J. Med. Chem.*, 21:31-37 (1978).

Padilla et al., "A Y639F/H784A T7 RNA polymerase double mutant displays superior properties for synthesizing RNAs with non-canonical NTPs", *Nuc. Acids Res.*, 30(24):e138 (2002).

Pietersz et al., "A 16-mer peptide (RQIKIWFQNRRMKWKK) from antennapedia preferentially targets the class I pathway", *Vaccine*, 19(11-12):1397-1405 (2001).

Rothbard et al., "Arginine-Rich Molecular Transporters for Drug Delivery: Role of Backbone Spacing in Cellular Uptake", *J. Med. Chem.*, 45(17):3612-3618 (2002).

Rothbard et al., "Conjugation of arginine oligomers to cyclosporine A facilitates topical delivery and inhibition of inflammation", *Nat. Med.*, 6(11):1253-1257 (2000).

Sood et al., "A rapid and convenient synthesis of poly-thymidylic acid by the modified triester approach", *Nuc. Acids Res.*, 4(8):2757-2765 (1977).

Sproat et al., "New synthetic routes to synthons suitable for 2'-O'allyloligoribonucleotide assembly", *Nuc. Acids Res.*, 19(4):733-738 (1990).

Tucker et al., "Detection and plasma pharmacokinetics of an anti-vascular endothelial growth factor oligonucleotide-aptamer (NX1838) in rhesus monkeys", *J. Chromatograph. B.*, 732:203-212 (1999).

Vives et al., "A Truncated HIV-1 Tat Protein Basic Domain Rapidly Translocates Through the Plasma Membrane and Accumulates in the Cell nucleus", *J. Biol. Chem.*, 272(25):16010-16017 (1997).

International Search Report for PCT/US06/08193, mailed Sep. 18, 2006.

ARC1091

SEQ. ID NO.: 17

*OMITTED IN ROUND 1

Fig. 10

| Aptamer ID | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | IC50 nM |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| SEQ ID 22 5'- | G | G | A | G | G | A | fC | fC | G | A | A | A | A | A | G | A | fC | fC | fU | G | A | fC | fU | fC | fU | A | fU | A | A | fC | fU | A | A | G | fU | fC | fU | A | A | fC | G | fU | fU | fC | fC | fU | fC | fC | -3' 6-18 |
| SEQ ID 77 5'- | G | G | A | G | G | A | fC | fC | G | A | A | A | A | A | G | A | fC | fC | fU | G | A | fC | fU | fC | fU | A | fU | A | A | fC | fU | A | A | G | fU | fC | fU | A | A | fC | G | fU | fU | fC | fC | fU | fC | fC | -3' 61 |
| SEQ ID 78 5'- | G | G | A | G | G | A | fC | fC | G | A | A | A | A | A | G | A | fC | fC | fU | G | A | fC | fU | fC | fU | A | fU | A | A | fC | fU | A | A | G | fU | fC | fU | A | A | fC | G | fU | fU | fC | fC | fU | fC | fC | -3' 23 |
| SEQ ID 79 5'- | G | G | A | G | G | A | fC | fC | G | A | A | A | U | A | G | A | fC | fC | fU | G | A | fC | fU | fC | fU | A | fU | A | A | fC | fU | A | A | G | fU | fC | fU | A | A | fC | G | fU | fU | fC | fC | fU | fC | fC | -3' 15 |
| SEQ ID 80 5'- | G | G | A | G | G | A | fC | fC | G | A | A | A | A | A | G | A | fC | fC | fU | G | A | fC | fU | fC | fU | A | fU | A | A | fC | fU | A | A | G | fU | fC | fU | A | A | fC | G | fU | fU | fC | fC | fU | fC | fC | -3' 31 |
| SEQ ID 81 5'- | G | G | A | G | G | A | fC | fC | G | A | A | A | A | A | G | A | fC | fC | fU | G | A | fC | fU | fC | fU | A | fU | A | A | fC | fU | A | A | G | G | fC | fU | A | A | fC | G | fU | fU | fC | fC | fU | fC | fC | -3' 187 |
| SEQ ID 82 5'- | G | G | A | G | G | A | fC | fC | G | A | A | A | A | A | G | A | fC | fC | fU | G | A | fC | fU | fC | fU | A | fU | A | A | fC | fU | A | A | G | fU | fC | fU | A | A | fC | G | fU | fU | fC | fC | fU | fC | fC | -3' 16 |
| SEQ ID 83 5'- | G | G | A | G | G | A | fC | fC | G | A | A | A | A | A | G | A | fC | fC | fU | G | A | fC | fU | fC | fU | A | fU | A | A | fC | fU | A | A | G | fU | fC | fU | A | A | fC | G | fU | fU | fC | fC | fU | fC | fC | -3' 14 |
| SEQ ID 84 5'- | G | G | A | G | G | A | fC | fC | G | A | A | A | A | A | G | A | fC | fC | fU | G | A | fC | fU | fC | fU | A | fU | A | A | fC | fU | A | A | G | fU | fC | fU | A | G | fC | G | fU | fU | fC | fC | fU | fC | fC | -3' 18 |
| SEQ ID 85 5'- | G | G | A | G | G | A | fC | fC | G | A | A | A | A | A | G | A | fC | fC | fU | G | A | fC | fU | fC | fU | A | fU | A | A | fC | fU | A | A | G | fU | fC | fU | A | A | fC | G | fU | fU | fC | fC | fU | fC | fC | -3' 27 |
| SEQ ID 86 5'- | G | G | A | G | G | A | fC | fC | G | A | A | A | A | A | G | A | fC | fC | fU | G | A | fC | fU | fC | fU | A | fU | A | A | fC | fU | A | A | G | fU | fC | fU | A | A | A | G | A | fU | fC | fC | fU | fC | fC | -3' 48 |
| SEQ ID 87 5'- | mG | mG | mA | mG | mG | mA | fC | fC | G | A | A | A | A | A | G | A | fC | fC | fU | G | A | fC | fU | fC | fU | A | fU | A | A | fC | fU | A | A | G | fU | fC | fU | A | A | fC | G | fU | fU | fC | fC | fU | fC | fC | -3' 11 |

PHASE 2 OPTIMIZATION

| APTAMER ID | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | | IC50 Naaladase (nM) | Seq. ID |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| ARC 1574 | 5'- | mC | mG | mG | mA | fC | fC | mG | A | A | mA | mA | mG | mG | mC | mC | fC | fU | G | A | fC | fU | fU | fC | fU | A | A | fC | fU | A | mG | mC | mC | mC | mU | mU | fC | mG | fU | mU | mC | mC | mG | 3T | 3' | | 16 | 143 |
| ARC 1575 | 5'- | mC | mG | mG | mA | fC | fC | mG | A | A | A | mA | mG | mG | mC | mC | fC | fU | G | A | fC | fU | fU | fC | fU | A | A | fC | fU | A | mG | mC | mC | mC | mU | mU | fC | mG | fU | mU | mC | mC | mG | 3T | 3' | | 34 | 144 |
| ARC 1576 | 5'- | mC | mG | mG | mA | fC | fC | mG | A | A | mA | A | mG | mG | mC | mC | fC | fU | G | A | fC | fU | fU | fC | fU | A | A | fC | fU | A | mG | mC | mC | mC | mU | A | fC | mG | fU | mU | mC | mC | mG | 3T | 3' | | 32 | 145 |
| ARC 1577 | 5'- | mC | mG | mG | mA | fC | fC | mG | A | A | mA | A | mG | mG | mC | mC | fC | fU | G | A | fC | fU | fU | fC | fU | A | A | fC | fU | A | mG | mC | mC | mC | mU | mU | fC | mG | fU | mU | mC | mC | mG | 3T | 3' | | 9 | 146 |
| ARC 1578 | 5'- | mC | mG | mG | mA | fC | fC | mG | A | A | mA | A | mG | mG | mC | mC | fC | fU | dG | A | fC | fU | fU | fC | fU | A | A | fC | fU | A | mG | mC | mC | mC | mU | mU | fC | mG | fU | mU | mC | mC | mG | 3T | 3' | | 28 | 147 |
| ARC 1579 | 5'- | mC | mG | mG | mA | fC | fC | mG | A | A | mA | A | mG | mG | mC | mC | fC | fU | dG | A | A | fC | fU | fU | fC | fU | A | A | fC | fU | A | mG | mC | mC | mC | mU | A | fC | mG | fU | mU | mC | mC | mG | 3T | 3' | | 76 | 148 |
| ARC 1580 | 5'- | mC | mG | mG | mA | fC | fC | mG | A | A | mA | A | mG | mG | mC | mC | fC | fU | G | mA | fC | fU | fU | fC | fU | A | A | fC | fU | A | mG | mC | mC | mC | mU | mU | fC | mG | fU | mU | mC | mC | mG | 3T | 3' | | 17 | 149 |
| ARC 1581 | 5'- | mC | mG | mG | mA | fC | fC | mG | A | A | mA | A | mG | mG | mC | mC | fC | fU | G | mA | fC | fU | fU | fC | fU | mA | A | fC | fU | dA | mG | mC | mC | mC | mU | mU | fC | mG | fU | mU | mC | mC | mG | 3T | 3' | | 360 | 150 |
| ARC 1582 | 5'- | mC | mG | mG | mA | fC | fC | mG | dA | dA | mA | A | mG | mG | mC | mC | fC | fU | dG | mA | fC | fU | fU | fC | fU | mA | A | fC | fU | dA | mG | mC | mC | mC | mU | mU | fC | mG | fU | mU | mC | mC | mG | 3T | 3' | | 30 | 151 |
| ARC 1583 | 5'- | mC | mG | mG | mA | fC | fC | mG | dA | A | mA | mA | mG | mG | mC | mC | fC | fU | dG | mA | fC | fU | fU | fC | fU | mA | A | fC | fU | dA | mG | mC | mC | mC | mU | mU | mA | fC | mG | fU | mU | mC | mC | mG | 3T | 3' | | 52 | 152 |
| ARC 1584 | 5'- | mC | mG | mG | mA | fC | fC | mG | A | A | mA | mA | mG | mG | mC | mC | fC | fU | G | mA | fC | fU | fU | fC | fU | mA | A | fC | fU | dA | mG | mC | mC | mC | mU | mU | fC | mG | fU | mU | mC | mC | mG | 3T | 3' | | 126 | 153 |
| ARC 1585 | 5'- | mC | mG | mG | mA | fC | fC | mG | dA | dA | mA | mA | mG | mG | mC | mC | fC | fU | dG | mA | fC | fU | fU | fC | fU | mA | A | fC | fU | dA | mG | mC | mC | mC | mU | mU | fC | mG | fU | mU | mC | mC | mG | 3T | 3' | | 43 | 154 |
| ARC 1586 | 5'- | mC | mG | mG | mA | fC | fC | mG | dA | dA | mA | mA | mG | mG | mC | mC | fC | fU | dG | mA | fC | fU | fU | fC | fU | mA | mA | fC | fU | dA | mA | mG | mC | mC | mC | mU | mU | mA | fC | mG | fU | mU | mC | mC | mG | 3T | 3' | | 460 | 155 |

Fig. 11-3

PHASE 3 OPTIMIZATION

| APTAMER ID | | 1 | 2 | 2 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | | IC50 Naaladase (nM) | Seq. ID |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| ARC 1721 | 5'- | mC | mG | mG | mA | fC | fC | mG | A | A | A | mA | mG | mG | mC | mC | fC | fU | G | A | fC | fU | fU | fC | fU | mA | fU | A | fC | fU | A | mG | mC | mC | mC | mU | mU | fC | mG | fU | mU | mC | mG | mG | 3T | 3' | | 82 | 156 |
| ARC 1722 | 5'- | mC | mG | mG | mA | fC | fC | mG | dA | A | A | mA | mG | mG | mC | mC | fC | fU | G | A | fC | fU | fU | fC | fU | mA | fU | A | fC | fU | A | mG | mC | mC | mC | mU | mU | fC | mG | fU | mU | mC | mG | mG | 3T | 3' | | 52 | 159 |
| ARC 1723 | 5'- | mC | mG | mG | mA | fC | fC | mG | dA | dA | A | mA | mG | mG | mC | mC | fC | fU | G | A | fC | fU | fU | fC | fU | mA | fU | A | fC | fU | dA | mG | mC | mC | mC | mU | mU | fC | mG | fU | mU | mC | mG | mG | 3T | 3' | | | 160 |
| ARC 1724 | 5'- | mC | mG | mG | mA | fC | fC | mG | dA | dA | A | mA | mG | mG | mC | mC | fC | fU | G | A | fC | fU | fU | fC | fU | mA | fU | A | fC | fU | dA | mG | mC | mC | mC | mU | mU | fC | mG | fU | mU | mC | mG | mG | 3T | 3' | | 260 | 161 |
| ARC 1725 | 5'- | mC | mG | mG | mA | fC | fC | mG | dA | dA | A | mA | mG | mG | mC | mC | fC | fU | sdG | mA | fC | fU | fU | fC | fU | mA | fU | A | fC | fU | dA | mG | mC | mC | mC | mU | mU | fC | mG | fU | mU | mC | mG | mG | 3T | 3' | | 47 | 162 |
| ARC 1726 | 5'- | mC | mG | mG | mA | fC | fC | mG | dA | dA | A | mA | mG | mG | mC | mC | fC | fU | sdG | mA | fC | fU | fU | fC | fU | mA | fU | A | fC | fU | dA | mG | mC | mC | mC | mU | mU | fC | mG | fU | mU | mC | mG | mG | 3T | 3' | | | 164 |
| ARC 1727 | 5'- | mC | mG | mG | mA | fC | fC | mG | dA | sdA | A | mA | mG | mG | mC | mC | fC | fU | G | mA | fC | fU | fU | fC | fU | mA | fU | A | fC | fU | dA | mG | mC | mC | mC | mU | mU | mA | fC | mG | fU | mU | mC | mG | mG | 3T | 3' | | 82 | 165 |

Fig. 11-4

STABILIZED APTAMERS TO PSMA AND THEIR USE AS PROSTATE CANCER THERAPEUTICS

REFERENCE TO RELATED APPLICATIONS

This application is a continuation-in-part of U.S. patent application Ser. No. 10/826,077, filed on Apr. 15, 2004, now abandoned, which is a continuation-in-part of U.S. patent application Ser. No. 10/600,007 filed Jun. 18, 2003, now abandoned, which claims priority under 35 U.S.C. §119(e) to U.S. Provisional Patent Application No. 60/390,042 filed Jun. 18, 2002. This application also claims priority under 35 U.S.C. §119(e) to the following provisional patent applications: U.S. Provisional Patent Application No. 60/660,514 filed Mar. 7, 2005, and U.S. Provisional Patent Application No. 60/670,518 filed Apr. 11, 2005; each of which is incorporated by reference herein.

FIELD OF INVENTION

The invention relates generally to the field of nucleic acids and more particularly to aptamers capable of binding to PSMA useful as therapeutics in and diagnostics of prostate cancer and/or other diseases or disorders in which PSMA has been implicated. The invention further relates to materials and methods for the administration of aptamers capable of binding to PSMA.

BACKGROUND OF THE INVENTION

Aptamers are nucleic acid molecules having specific binding affinity to molecules through interactions other than classic Watson-Crick base pairing.

Aptamers, like peptides generated by phage display or monoclonal antibodies ("mAbs"), are capable of specifically binding to selected targets and modulating the target's activity, e.g., through binding aptamers may block their target's ability to function. Created by an in vitro selection process from pools of random sequence oligonucleotides, aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., aptamers will typically not bind other proteins from the same gene family). A series of structural studies have shown that aptamers are capable of using the same types of binding interactions (e.g., hydrogen bonding, electrostatic complementarity, hydrophobic contacts, steric exclusion) that drive affinity and specificity in antibody-antigen complexes.

Aptamers have a number of desirable characteristics for use as therapeutics and diagnostics including high specificity and affinity, biological efficacy, and excellent pharmacokinetic properties. In addition, they offer specific competitive advantages over antibodies and other protein biologics, for example:

1) Speed and control. Aptamers are produced by an entirely in vitro process, allowing for the rapid generation of initial leads, including therapeutic leads. In vitro selection allows the specificity and affinity of the aptamer to be tightly controlled and allows the generation of leads, including leads against both toxic and non-immunogenic targets.

2) Toxicity and Immunogenicity. Aptamers as a class have demonstrated little or no toxicity or immunogenicity. In chronic dosing of rats or woodchucks with high levels of aptamer (10 mg/kg daily for 90 days), no toxicity is observed by any clinical, cellular, or biochemical measure. Whereas the efficacy of many monoclonal antibodies can be severely limited by immune response to antibodies themselves, it is extremely difficult to elicit antibodies to aptamers most likely because aptamers cannot be presented by T-cells via the MHC and the immune response is generally trained not to recognize nucleic acid fragments.

3) Administration. Whereas most currently approved antibody therapeutics are administered by intravenous infusion (typically over 2-4 hours), aptamers can be administered by subcutaneous injection (aptamer bioavailability via subcutaneous administration is >80% in monkey studies (Tucker et al., J. Chromatography B. 732: 203-212, 1999)). This difference is primarily due to the comparatively low solubility and thus large volumes necessary for most therapeutic mAbs. With good solubility (>150 mg/mL) and comparatively low molecular weight (aptamer: 10-50 kDa; antibody: 150 kDa), a weekly dose of aptamer may be delivered by injection in a volume of less than 0.5 mL. In addition, the small size of aptamers allows them to penetrate into areas of conformational constrictions that do not allow for antibodies or antibody fragments to penetrate, presenting yet another advantage of aptamer-based therapeutics or prophylaxis.

4) Scalability and cost. Therapeutic aptamers are chemically synthesized and consequently can be readily scaled as needed to meet production demand. Whereas difficulties in scaling production are currently limiting the availability of some biologics and the capital cost of a large-scale protein production plant is enormous, a single large-scale oligonucleotide synthesizer can produce upwards of 100 kg/year and requires a relatively modest initial investment. The current cost of goods for aptamer synthesis at the kilogram scale is estimated at $500/g, comparable to that for highly optimized antibodies. Continuing improvements in process development are expected to lower the cost of goods to <$100/g in five years.

5) Stability. Therapeutic aptamers are chemically robust. They are intrinsically adapted to regain activity following exposure to factors such as heat and denaturants and can be stored for extended periods (>1 yr) at room temperature as lyophilized powders.

Prostate Cancer and Current Treatments

Prostate cancer is a major medical problem of unmet need. It is the most common form of cancer in men with a lifetime incidence (cumulative from birth to death) of 1 in 6. Overall, prostate cancer is the second highest cause of cancer deaths in men (~30,000 per year). Within the U.S., 220,900 patients were diagnosed with prostate cancer in 2003. Most of these patients are diagnosed early and the cure rate is very high with surgery and/or radiation treatment. However, 10-50% of patients with localized disease will progress to advanced metastatic disease (Stage III).

There are currently limited treatment options available for advanced metastatic prostate cancer. Life-long androgen ablation therapy (androgen deprivation therapy, hormone deprivation therapy) is the current standard of care for metastatic prostate cancer. Gonadotropin Releasing Hormone ("GnRH") (also referred to as Lutenizing Hormone Releasing Hormone or "LHRH") antagonists, such as Lupron Depot® and Zoladex® block the production of androgens at the level of the pituitary gland, while drugs such as flutamide block androgen production at the level of the adrenal gland, and finasteride block binding of androgens to its receptor. However, cure is rare at this late stage, and the median length of response to hormone therapy is 18-24 months, with most if not all patients subsequently relapsing. The prognosis for patients showing rising prostate specific antigen ("PSA") or other signs of progression at this stage is poor with only 60% surviving another year. In this late stage, quality of life ("QOL") is generally reduced, at least in part due to the side effects of androgen deprivation therapy, which include fatigue, loss of muscle mass, sexual dysfunction, nausea and vomiting, emotional distress and gynecomastia.

Oftentimes upon relapse, prostate cancer which was once responsive to androgen ablation therapy becomes unresponsive, or androgen independent, after which effective treatment options drastically decline. Chemotherapy is currently utilized in patients with androgen-independent metastatic disease (Stage IV), also known as androgen independent prostate cancer ("AIPC"). It is currently the only available therapeutic option for AIPC, and is often used in combination with corticosteroids, such as prednisone, to reduce pain and increase QOL. However, current chemotherapeutic regimes offer little in terms of increased survival and have been approved mainly on the basis of improvement in QOL, primarily through effects in managing pain.

Until recently, Novantron® (mitoxantrone), administered in combination with prednisone, was the standard of care for AIPC. In clinical trials supporting development of Novantron®, palliation response was the primary endpoint; survival, lesion size change, PSA level decline, and QOL were secondary endpoints. The pivotal studies supporting registration showed modest efficacy in terms of the palliation response endpoint and secondary endpoints, but no effect on survival. In May, 2004 the FDA approved Taxotere® (docetaxel) injection in combination with prednisone for the treatment of patients with androgen independent metastatic prostate cancer. Safety and effectiveness of Taxotere was established in a randomized, multi-center global clinical trial with over 1,000 patients comparing chemotherapy with Taxotere® and prednisone, to mitoxantrone and prednisone, in men with metastatic, androgen independent prostate cancer. Taxotere®, in combination with prednisone, given every three weeks showed a survival advantage of approximately 2.5 months over the control group in the trial. This is the first drug approved for hormone refractory prostate cancer that has shown any survival benefit, although minimal.

Aptamer-Toxin Conjugates as a Cancer Therapeutic

Extensive previous work has developed the concept of antibody-toxin conjugates ('immunoconjugates') as potential therapies for a range of indications, mostly directed at the treatment of cancer with a primary focus on hematological tumors. A variety of different payloads for targeted delivery have been tested in pre-clinical and clinical studies, including protein toxins, high potency small molecule cytotoxics, radioisotopes, and liposome-encapsulated drugs. While these efforts have successfully yielded three FDA-approved therapies for hematological tumors (Myotarg, Zevalin®, and Bexxar®), immunoconjugates as a class (especially for solid tumors) have historically yielded disappointing results that have been attributable to multiple different properties of antibodies, including tendencies to develop neutralizing antibody responses to non-humanized antibodies, limited penetration in solid tumors, loss of target binding affinity as a result of toxin conjugation, and imbalances between antibody half-life and toxin conjugate half-life that limit the overall therapeutic index (reviewed by Reff and Heard, Critical Reviews in Oncology/Hematology, 40 (2001):25-35).

As previously mentioned, aptamers are functionally similar to antibodies, except their absorption, distribution, metabolism, and excretion ("ADME") properties are intrinsically different and they generally lack many of the immune effector functions generally associated with antibodies (e.g., antibody-dependent cellular cytotoxicity, complement-dependent cytotoxicity). In comparing many of the properties of aptamers and antibodies previously described, several factors suggest that toxin-delivery via aptamers offers several concrete advantages over delivery with antibodies, ultimately affording them better potential as therapeutics. Several examples of the advantages of toxin-delivery via aptamers over antibodies are as follows:

1) Aptamer-toxin conjugates are entirely chemically synthesized. Chemical synthesis provides more control over the nature of the conjugate. For example, the stoichiometry (ratio of toxins per aptamer) and site of attachment can be precisely defined. Different linker chemistries can be readily tested. The reversibility of aptamer folding means that loss of activity during conjugation is unlikely and provides more flexibility in adjusting conjugation conditions to maximize yields.

2) Smaller size allows better tumor penetration. Poor penetration of antibodies into solid tumors is often cited as a factor limiting the efficacy of conjugate approaches (Colcher, D., Goel, A., Pavlinkova, G., Beresford, G., Booth, B., Batra, S. K. (1999) "Effects of genetic engineering on the pharmacokinetics of antibodies", *Q. J. Nucl. Med.*, 43: 132-139). Studies comparing the properties of unPEGylated anti-tenascin C aptamers with corresponding antibodies demonstrate efficient uptake into tumors (as defined by the tumor:blood ratio) and evidence that aptamer localized to the tumor is unexpectedly long-lived ($t_{1/2}$>12 hours) (Hicke, B. J., Stephens, A. W., "Escort aptamers: a delivery service for diagnosis and therapy", *J. Clin. Invest.*, 106:923-928 (2000)).

3) Tunable PK. Aptamer half-life/metabolism can be easily tuned to match properties of payload, optimizing the ability to deliver toxin to the tumor while minimizing systemic exposure. Appropriate modifications to the aptamer backbone and addition of high molecular weight PEGs should make it possible to match the half-life of the aptamer to the intrinsic half-life of the conjugated toxin/linker, minimizing systemic exposure to non-functional toxin-bearing metabolites (expected if $t_{1/2}$(aptamer)<<$t_{1/2}$(toxin)) and reducing the likelihood that persisting unconjugated aptamer will functionally block uptake of conjugated aptamer (expected if $t_{1/2}$(aptamer)>>$t_{1/2}$(toxin)).

4) Relatively low material requirements. It is likely that dosing levels will be limited by toxicity intrinsic to the cytotoxic payload. As such, a single course of treatment will likely entail relatively small (<100 mg) quantities of aptamer, reducing the likelihood that the cost of oligonucleotide synthesis will be a barrier for aptamer-based therapies.

5) Parenteral administration is preferred for this indication. There will be no special need to develop alternative formulations to drive patient/physician acceptance.

PSMA

Prostate specific membrane antigen ("PSMA") is a homodimeric type II integral membrane protein with NAALADase enzymatic activity. It is highly expressed on prostatic epithelial cells, and is known to be up-regulated throughout progression of prostate cancer. PSMA constitutively internalizes via clathrin coated pits. This constitutive internalization combined with high expression on prostate cancer cells makes PSMA an attractive target for new prostate cancer therapeutics. Interestingly, PSMA expression has also been discovered in the neovasculature of non-prostate solid tumors, thus making it an attractive target for the development an anti-angiogenic agent for non-prostate solid tumors as well.

As previously described, PSMA is a membrane protein whose expression is limited to prostate cells and the neovasculature of other solid non-prostate tumors, is highly upregulated in the progression of prostate cancer, and is constitutively internalized. Thus, aptamers specific for PSMA can be used to specifically deliver a toxic payload to PSMA expressing cells only, causing little to no toxic side effects in non-PSMA expressing cells. Due to the critical unmet medical need for effective therapeutics in the treatment of advance metastatic and androgen independent prostate cancer, it would be beneficial to have toxin-conjugated PSMA specific aptamers for the delivery of cytotoxic moieties to PSMA expressing cells. The present invention provides materials and methods to meet these and other needs.

SUMMARY OF THE INVENTION

The present invention provides materials and methods for targeted delivery of toxic payloads to PSMA expressing cells, and materials and methods for the treatment of diseases associated with PSMA expression. In some embodiments, the methods and materials of the invention are used to treat prostate cancer, while in other embodiments, the methods and materials are used as an anti-angiogenic agent for the treatment of non-prostate solid tumors. While in still other embodiments, the methods and materials of the invention are used in in vitro and in vivo diagnostics.

The present invention provides aptamers that specifically bind to prostate specific membrane antigen ("PSMA"), particularly to the extracellular domain ("ECD") of PSMA. In some embodiments, the PSMA to which the aptamers of the invention specifically bind is human PSMA, particularly the ECD of the human PSMA. In some embodiments, the PSMA to which the aptamers of the invention bind is a variant of human PSMA that performs a biological function that is essentially the same as a function of human PSMA. In some embodiments, the ECD of PSMA to which the aptamers of the invention bind is a variant ECD of human PSMA that performs a biological function that is essentially the same as a function of the ECD of human PSMA. In some embodiments, the biological function of PSMA, ECD of PSMA or a variant thereof, to which the aptamers of the invention bind, is NAALADase activity. In some embodiments, the variant of human ECD of PSMA has substantially the same structure and substantially the same ability to bind the aptamer of the invention as that of human ECD of PSMA. In some embodiments, the aptamer of the invention binds the ECD of PSMA, or a variant thereof, that comprises an amino acid sequence which is at least 80%, particularly at least 90% identical to SEQ ID NO 5. In some embodiments, the ECD of PSMA to which the aptamers of the invention bind comprises the amino acid sequence of SEQ ID NO 5.

In some embodiments, the aptamer of the invention has a dissociation constant ($K_D$) for human ECD of PSMA or a variant thereof of at least 1 µM or less, 50 nM or less, 20 nM or less, 10 nM or less, 5 nM or less or 500 pM or less. In some embodiments, the $K_D$ values are determined by setting up binding reactions in which trace 5'-$^{32}$P-labeled aptamer is incubated with a dilution series of purified recombinant PSMA in 1×DPBS (with Ca$^{++}$ and Mg$^{++}$) with 0.1 mg/mL BSA at room temperature for 30 minutes. The binding reactions are then analyzed by nitrocellulose filtration using a Minifold I dot-blot, 96-well vacuum filtration manifold (Schleicher & Schuell, Keene, N.H.) (dot blot binding assay).

A three-layer filtration medium is used, consisting (from top to bottom) of Protran nitrocellolose (Schleicher & Schuell), Hybond-P nylon (Amersham Biosciences, Piscataway, N.J.) and GB002 gel blot paper (Schleicher & Schuell). The nitrocellulose layer, which selectively binds protein over nucleic acid, preferentially retains the anti-PSMA aptamer in complex with a protein ligand, while non-complexed anti-PSMA aptamer passes through the nitrocellulose and adhered to the nylon (the gel blot paper is included as a supporting medium for the other filters). Following filtration, the filter layers are separated, dried and exposed on a phosphor screen (Amersham Biosciences) and quantified using a Storm 860 Phosphorimager® blot imaging system (Amersham Biosciences) and $K_D$ values are calculated by fitting the equation y=(max/(1+K/protein))+yint. In other embodiments, the $K_D$ values are determined by the nitrocellulose filter binding assay under the conditions described in Example 1 below.

In some embodiments, the aptamer of the invention has substantially the same ability to bind the ECD of PSMA as that of an aptamer comprising a nucleotide sequence selected from the group consisting of SEQ ID NOs 11-13, 15-26, 30-90, 122-165, 167. In other embodiments, the aptamer of the invention has substantially the same structure and substantially the same ability to bind the ECD of PSMA as that of an aptamer comprising a nucleotide sequence selected from the group consisting of SEQ ID 11-13, 15-26, 30-90, 122-165, 167.

In some embodiments, the aptamer of the invention comprises a nucleic acid sequence which is at least 80% identical to any one of the sequences selected from the group consisting of SEQ ID NOs: 11-13, 15-26, 30-90, 122-165, and 167. In other embodiments, the aptamer of the invention comprises a nucleic acid sequence which is at least 90% identical to any one of the sequences selected from the group consisting of SEQ ID NOs 11-13, 15-26, 30-90, 122-165, and 167. In yet another embodiment, the aptamer of the invention comprises a nucleic acid sequence which is at least 95% identical to any one of the sequences selected from the group consisting of SEQ ID NOs 11-13, 15-26, 30-90, 122-165, and 167. In yet another embodiment, the aptamer of the invention comprises a nucleic acid sequence selected from the group consisting of SEQ ID NOs 11-13, 15-26, 30-90, 122-165, and 167.

In some embodiments, the aptamer of the invention comprises a nucleic acid sequence which is at least 80% identical, particularly at least 90% identical, more particularly at least 95% identical to any one of the sequences selected from the group consisting of SEQ ID NOs: 11-13 and 15-19.

In a preferred embodiment, the aptamer of the invention comprises a nucleic acid sequence selected from the group consisting of: SEQ ID NO 17 (ARC1091), SEQ ID NO 18 (ARC1142), SEQ ID NO 19 (ARC1786), SEQ ID NO 22 (ARC591), SEQ ID NO 23 (ARC2038), SEQ ID NO 24 (ARC2039), SEQ ID NO 88 (ARC1113), SEQ ID NO 89 (ARC2035), SEQ ID NO 90 (ARC2036), SEQ ID NO 128 (ARC942), SEQ ID NO 129 (ARC2037), SEQ ID NO 130 (ARC1026), SEQ ID NO 156 (ARC1721), SEQ ID NO 157 (ARC2033), SEQ ID NO 158 (ARC2038), SEQ ID NO 162 (ARC1725), SEQ ID NO 163 (ARC2032).

In some embodiments, the aptamer of the invention is selected according to a method of the invention comprising: preparing a candidate mixture of nucleic acids; contacting the candidate mixture of nucleic acid sequences with a suspension of cells which express an aptamer target, e.g. PSMA, on the cell surface; isolating a population of nucleic acid sequences having increased affinity for the target expressing live cells only, e.g. the PSMA expressing live cells only; and amplifying the increased affinity nucleic acid sequences to yield a mixture of nucleic acid sequences enriched for nucleic acids with relatively higher affinity and specificity for binding to target expressing, e.g. PSMA expressing, cells. In some embodiments the contacting, isolating and amplifying steps are repeated iteratively. In some embodiments the enriched nucleic mixture is transcribed prior to the contacting step, particularly where the contacting, isolating, amplifying and transcribing steps are repeated iteratively. In a further embodiment the method comprises the additional step of identifying a nucleic acid ligand that binds to the target, e.g. PSMA. In some embodiments, the method further comprises nucleic acid ligand analysis in a functional assay such as an in vitro biochemical assay and/or a functional cell based assay and/or by binding in a dot blot assay.

In one embodiment of the method, the candidate nucleic acid mixture is a biased pool that has previously undergone SELEX™ where the target was an isolated protein rather than one expressed on the cell surface. In a particular embodiment of the method of selecting an aptamer of the invention, the candidate nucleic acid mixture is a synthetic degenerate pool based on an aptamer nucleic sequence previously identified by SELEX™ that binds specifically to a target, e.g., PSMA, particularly the ECD of PSMA, more particularly, the ECD of human PSMA. In a preferred embodiment, said method further comprises contacting the nucleic acid mixture with a suspension of cells which do not express the target, e.g. PSMA, on the cell surface in a negative selection step. In some embodiments, the nucleic acid mixture is contacted with the cells that do not express the aptamer target, e.g. that do not express PSMA, prior to contacting the mixture with target expressing, e.g. the PSMA expressing, cells. In a particular embodiment, the cells that do not express the aptamer target, e.g. that do not express PSMA, are of a different cell type than those that do express the target, e.g. PSMA. In some embodiments, the PSMA expressing cells which are contacted with the nucleic acid mixture are LNCaP cells and the non-PSMA expressing cells are PC3 cells. In some embodiments of the method of selecting an aptamer of the invention, the method used to isolate the population of increased affinity nucleic acids associated with live cells is FACS analysis.

In some embodiments, the aptamers of the invention modulates a function of PSMA. In some embodiments, the aptamers of the invention modulate a function of PSMA in vitro. In some embodiments, the aptamers of the invention modulate a function of PSMA in vivo. In some embodiments, the aptamers of the invention inhibit a function of PSMA. In some embodiments, the biological function of PSMA modulated by the aptamer of the invention is NAALADase activity.

The present invention provides aptamers that are ribonucleic acid or deoxyribonucleic acid. Aptamers of the invention may be single stranded ribonucleic acid, deoxyribonucleic acid, or a combination of ribonucleic and deoxyribonucleic acids. In some embodiments, the aptamer of the invention comprises at least one chemical modification. In some embodiments, the modification is selected from the group consisting: of a chemical substitution at a sugar position; a chemical substitution at a phosphate position; and a chemical substitution at a base position, of the nucleic acid. In other embodiments, the modification is selected from the group consisting of: incorporation modified nucleotides; 3' capping, 5' capping, conjugation to a high molecular weight, non-immunogenic compound, conjugation to an amine linker, conjugation to a lipophilic compound, and incorporation of phosphorothioate into the phosphate back bone. In a preferred embodiment, the non-immunogenic, high molecular weight compound is polyalkylene glycol, more preferably polyethylene glycol. In another preferred embodiment, the modified nucleotides comprise 2'-fluoro modified nucleotides, 2'-O-methyl modified nucleotides, and 2'-deoxy modified nucleotides.

The present invention provides aptamers that are conjugated to a drug, such as a cytotoxic moiety or labeling with a radioisotope. In some embodiments, the drug such as the cytotoxic moiety is conjugated to the 3'-end of the aptamer, while in other embodiments, the drug, such as the cytotoxic moiety is conjugated to the 5'-end of the aptamer. In some embodiments, the drug such as the cytotoxic moiety is encapsulated in nanoparticle forms, including but no limited to liposomes, dendrimers, and comb polymers. In one embodiment the cytotoxic moiety is a small molecule, including without limitation, vinblastine hydrazide, calicheamicin, vinca alkaloid, a cryptophycin, a tubulysin, dolastatin-10, dolastatin-15, auristatin E, rhizoxin, epothilone B, epithilone D, taxoids, maytansinoids and any variants and derivatives thereof. In another embodiment, the cytotoxic moiety is a radioisotope, including but not limited to yttrium-90, indium-111, iodine-131, lutetium-177, copper-67, rhenium-186, rhenium-188, bismuth-212, bismuth-213, astatine-211, and actinium-225. In yet another embodiment, the cytotoxic moiety is a protein toxin, including without limitation, diphtheria toxin, ricin, abrin, gelonin, and Pseudomonas exotoxin A.

In some embodiments, the aptamer conjugated to a cytotoxic moiety is selected from the group consisting of: SEQ ID NOs 11-13, 15-26, 30-90, 122-165, 167 and 168. In some embodiments the aptamer conjugated to a cytotoxic moiety is selected from the group consisting of SEQ ID NO 17 (ARC1091), SEQ ID NO 18 (ARC1142), SEQ ID NO 19 (ARC1786), SEQ ID NO 22 (ARC591), SEQ ID NO 23 (ARC2038), SEQ ID NO 24 (ARC2039), SEQ ID NO 88 (ARC1113), SEQ ID NO 89 (ARC2035), SEQ ID NO 90 (ARC2036), SEQ ID NO 128 (ARC942), SEQ ID NO 129 (ARC2037), SEQ ID NO 130 (ARC1026), SEQ ID NO 156 (ARC1721), SEQ ID NO 157 (ARC2033), SEQ ID NO 158 (ARC2038), SEQ ID NO 162 (ARC1725), SEQ ID NO 163 (ARC2032), SEQ ID NO 167 (ARC964) and SEQ ID NO 168 (A9). In some embodiments, the aptamer conjugated to a cytotoxic moiety is selected from the group consisting of SEQ ID NO 18, SEQ ID NO 88, and SEQ ID NO 130. In particular embodiments, the aptamer conjugated to the cytotoxic moiety is selected from the group consisting of SEQ ID NO 18, SEQ ID NO 88, SEQ ID NO 130 and SEQ ID NO 167 and the cytotoxic moiety is selected from the group consisting of vinblastine and DM1.

In a particular embodiment, the aptamer-toxin conjugate of the invention comprises the following structure:

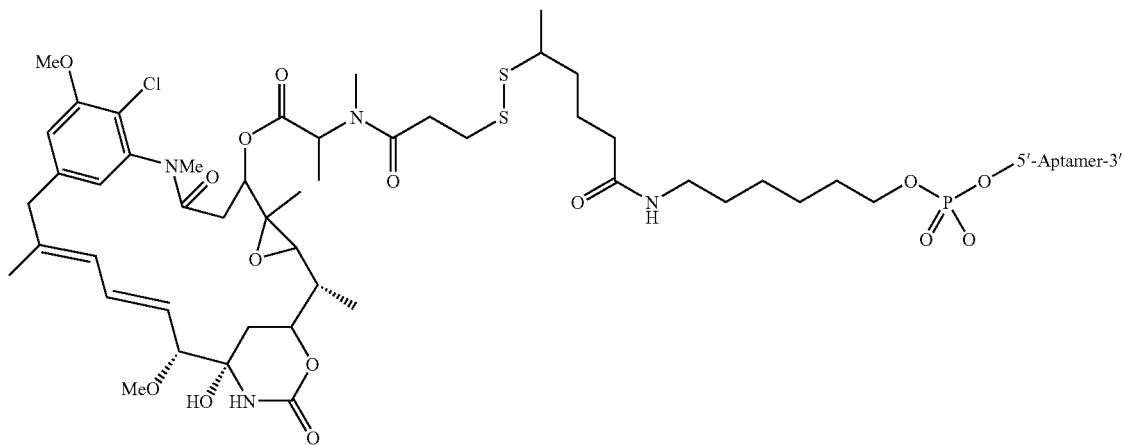

wherein the aptamer is selected from the group consisting of any one of: SEQ ID NO 17 and 90.

In another particular embodiment, the aptamer-toxin conjugate of the inventions comprises the following structure:

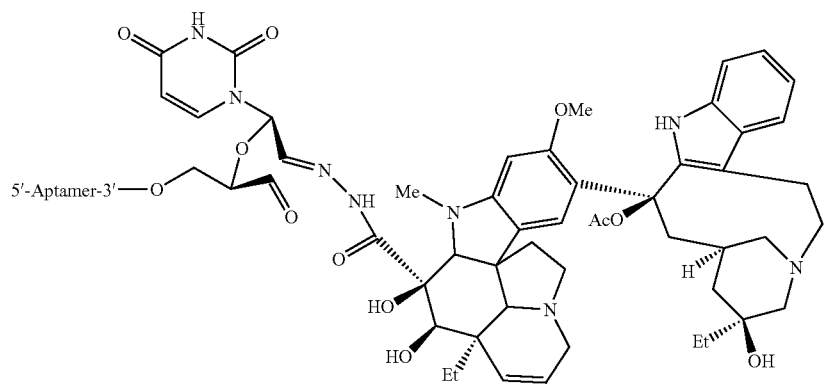

wherein the aptamer is selected from the group consisting of any one of SEQ ID NO 18, 130 and 167.

In some embodiments, the aptamers of the invention which are conjugated to a cytotoxic moiety are also conjugated to a high molecular weight, non-immunogenic compound. In a preferred embodiment, the high molecular weight, non-immunogenic compound is a polyethylene glycol moiety (PEG). In some embodiments of the PEG-aptamer-cytotoxin of the invention, the PEG moiety is conjugated to the 5'end of the aptamer, and the cytotoxic moiety is conjugated to the 3' end, while in other embodiments, the PEG moiety is conjugated to the 3' end of the aptamer and the cytotoxic moiety is conjugated to the 5'end. While in some embodiments, the aptamer is linked to the cytotoxin by the PEG moiety.

In some embodiments, the invention provides aptamer-toxin conjugates for use in the treatment, prevention and/or amelioration of prostate cancer. In another embodiment, the invention provides aptamer-toxin conjugates for use as an anti-angiogenic agent for the treatment, prevention and/or amelioration solid tumors in which PSMA is expressed, e.g., expressed in the neo-vasculature of the tumor. In another embodiment, a pharmaceutical composition comprising therapeutically effective amount of an aptamer-drug conjugate, particularly an aptamer-cytotoxin conjugate of the invention or a salt thereof, and a pharmaceutically acceptable carrier or diluent is provided. In some embodiments, the invention provides aptamer-toxin conjugates for use in in vitro and/or in vivo diagnostics.

The present invention provides a method for selecting aptamers specific for the PSMA comprising: preparing a candidate mixture of nucleic acids; contacting the candidate mixture of nucleic acid sequences with a suspension of cells which express PSMA on the cell surface; isolating the population of nucleic acid sequences having increased affinity for PSMA expressing live cells only; and amplifying the increased affinity nucleic acid sequences to yield a mixture of nucleic acid sequences enriched for nucleic acids with relatively higher affinity and specificity for binding to PSMA expressing cells. In a further embodiment, the method comprises the additional step of identifying a nucleic acid ligand that binds to PSMA. In some embodiments the identification step comprises analysis in a functional assay such as an in vitro biochemical assay and/or a functional cell based assay and/or by binding in a dot blot assay.

In one embodiment of said method of selecting an aptamer of the invention, the candidate nucleic acid mixture is a synthetic degenerate pool based on an aptamer nucleic sequence previously identified by SELEX™ that binds specifically to a target, e.g., PSMA, particularly the ECD of PSMA, more particularly, the ECD of human PSMA. In a preferred embodiment, said method further comprises contacting the nucleic acid mixture with a suspension of cells which do not express PSMA on the cell surface in a negative selection step. In some embodiments the negative selection step is performed prior to contacting the mixture with PSMA expressing cells. In a particular embodiment, the cells that do not express PSMA are of a different cell type as those that do express PSMA. In some embodiments, the PSMA expressing cells which are contacted with the nucleic acid mixture are LNCaP cells and the non-PSMA expressing cells are PC3 cells. In some embodiments of the method of selecting an aptamer of the invention, the method used to isolate the population of increased affinity nucleic acids associated with live cells is FACS analysis.

The present invention also provides a method of treating, preventing and/or ameliorating a disease associated with PSMA expression, comprising administering a pharmaceutical composition of the invention to a vertebrate, preferably a mammal, more preferably a human. In some embodiments, the disease to be treated, prevented or ameliorated is selected from the group consisting of: prostate cancer, including androgen dependent or androgen independent prostate cancer, and metastases thereof. In another embodiment, the disease to be treated prevented or ameliorated includes non-prostate solid tumors in which PSMA is expressed in the neovasculature of the tumor.

The present invention also provides aptamers that bind to PSMA for use as in vitro and in vivo diagnostics. In some embodiments, the aptamer of the invention to be used for in vivo or in vitro diagnostics is conjugated to a metal chelating agent to enable labeling with gamma emitting radioisotopes (e.g., $^{99}$Tc and $^{111}$Ind). In some embodiments, the present invention provides a diagnostic method comprising contacting an aptamer of the invention with a composition and detecting the presence or absence of PSMA or a variant thereof. In another embodiment, the present invention provides a diagnostic method for the detection, staging, and treatment of prostate cancer comprising the steps of labeling an aptamer specific for PSMA with a gamma-emitting radioisotope, administering the gamma emitting radiolabeled aptamer to a subject, and detecting localized radiometal in the subject. In some embodiments, the diagnostic method is for use in vitro, while in other embodiments, the diagnostic method is for use in vivo.

BRIEF DESCRIPTION OF THE DRAWINGS

FIG. 7 illustrates that chemically synthesized A9 minimer, ARC591 is functional and specific for PSMA.

FIG. 10 is a table showing the aligned sequences for the point mutant constructs designed and synthesized to optimize ARC591, indicating the positional mutations for each construct, and the effect of each point mutations on the apparent $IC_{50}$ (final column of the table) in a NAALADase inhibition assay, relative to the parent ARC591 aptamer.

FIG. 11 is a table a table showing the aligned sequences for all constructs generated during different phases of sequence optimization for ARC591 indicating the positions where mutations or 2'-substitutions were made for each construct, and the effect these changes on the apparent $IC_{50}$ (final column of the table) for each in a NAALADase inhibition assay, as compared to the parent ARC591 sequence.

(open squares) refer to unconjugated aptamers. Control aptamer-vin (filled squares) is a conjugate of vinblastine with ARC725, a non-functional minimer with a composition similar to ARC1142 shown not to exhibit PSMA binding.

DETAILED DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

The SELEX™ Method

Figure 1:
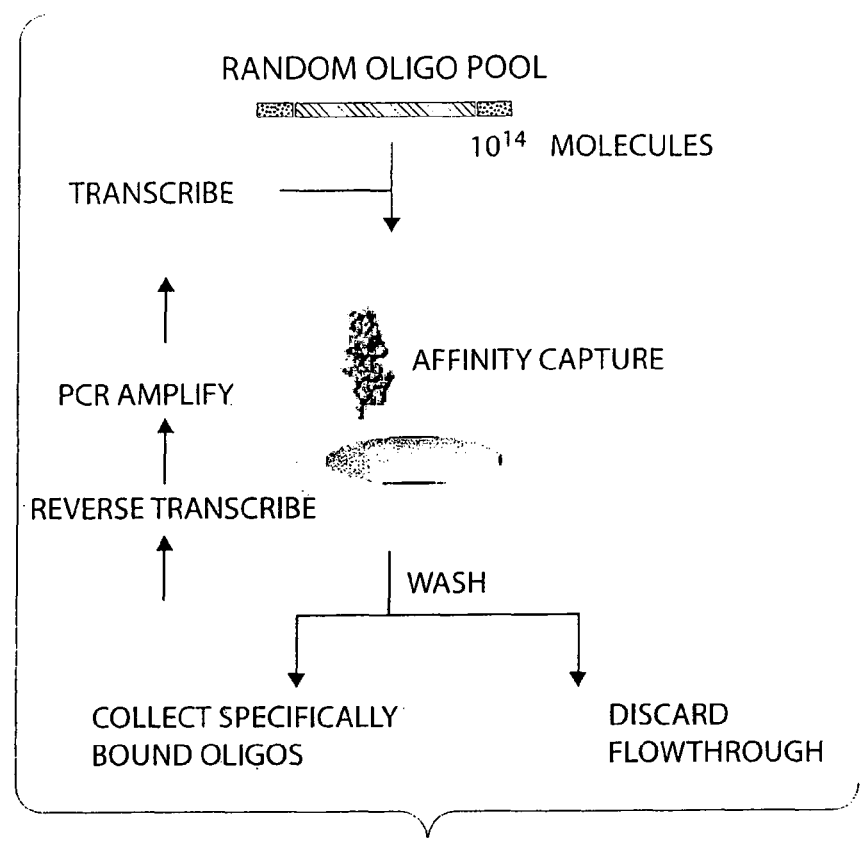
FIG. 1 is a schematic representation of the in vitro aptamer selection (SELEX™) process from pools of random sequence oligonucleotides.

A suitable method for generating an aptamer is with the process entitled "Systematic Evolution of Ligands by Exponential Enrichment" ("SELEX™") generally depicted in FIG. 1. The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX™-identified nucleic acid ligand, i.e., each aptamer, is a specific ligand of a given target compound or molecule. The SELEX™ process is based on the unique insight that nucleic acids have sufficient capacity for forming a variety of two- and three-dimensional structures and sufficient chemical versatility available within their monomers to act as ligands (i.e., form specific binding pairs) with virtually any chemical compound, whether monomeric or polymeric. Molecules of any size or composition can serve as targets.

SELEX™ relies as a starting point upon a large library or pool of single stranded oligonucleotides comprising randomized sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed and/or conserved sequence incorporated within randomized sequence. In other examples, the pool comprises random or partially random oligonucleotides containing at least one fixed and/or conserved sequence at its 5' and/or 3' end which may comprise a sequence shared by all the molecules of the oligonucleotide pool. Fixed sequences are sequences such as hybridization sites for PCR primers, promoter sequences for RNA polymerases (e.g., T3, T4, T7, and SP6), restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool preferably include a randomized sequence portion as well as fixed sequences necessary for efficient amplification. Typically the oligonucleotides of the starting pool contain fixed 5' and 3' terminal sequences which flank an internal region of 30-50 random nucleotides. The randomized nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs. See, e.g., U.S. Pat. No. 5,958,691; U.S. Pat. No. 5,660,985; U.S. Pat. No. 5,958,691; U.S. Pat. No. 5,698,687; U.S. Pat. No. 5,817,635; U.S. Pat. No. 5,672,695, and PCT Publication WO 92/07065. Random oligonucleotides can be synthesized from phosphodiester-linked nucleotides using solid phase oligonucleotide synthesis techniques well known in the art. See, e.g., Froehler et al., Nucl. Acid Res. 14:5399-5467 (1986) and Froehler et al., Tet. Lett. 27:5575-5578 (1986). Random oligonucleotides can also be synthesized using solution phase methods such as triester synthesis methods. See, e.g., Sood et al., Nucl. Acid Res. 4:2557 (1977) and Hirose et al., Tet. Lett., 28:2449 (1978). Typical syntheses carried out on automated DNA synthesis equipment yield $10^{14}$-$10^{16}$ individual molecules, a number sufficient for most SELEX™ experiments. Sufficiently large regions of random sequence in the sequence design increases the likelihood that each synthesized molecule is likely to represent a unique sequence.

The starting library of oligonucleotides may be generated by automated chemical synthesis on a DNA synthesizer. To synthesize randomized sequences, mixtures of all four nucleotides are added at each nucleotide addition step during the synthesis process, allowing for random incorporation of nucleotides. As stated above, in one embodiment, random oligonucleotides comprise entirely random sequences; however, in other embodiments, random oligonucleotides can comprise stretches of nonrandom or partially random sequences. Partially random sequences can be created by adding the four nucleotides in different molar ratios at each addition step.

The starting library of oligonucleotides may be for example, RNA, DNA, or RNA/DNA hybrid. In those instances where an RNA library is to be used as the starting library it is typically generated by transcribing a DNA library in vitro using T7 RNA polymerase or modified T7 RNA polymerases and purified. The library is then mixed with the target under conditions favorable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. A nucleic acid mixture comprising, for example, a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands or aptamers.

Cycles of selection and amplification are repeated until a desired goal is achieved. In the most general case, selection/amplification is continued until no significant improvement in binding strength is achieved on repetition of the cycle. The method is typically used to sample approximately $10^{14}$ different nucleic acid species but may be used to sample as many as about $10^{18}$ different nucleic acid species. Generally, nucleic acid aptamer molecules are selected in a 5 to 20 cycle procedure. In one embodiment, heterogeneity is introduced only in the initial selection stages and does not occur throughout the replicating process.

In one embodiment of SELEX™, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX™ until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX™ process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX™ procedures with contiguous randomized segments be initiated with nucleic acid sequences containing a randomized segment of between about 20 to about 50 nucleotides and in some embodiments, about 30 to about 40 nucleotides. In one example, the 5'-fixed:random:3'-fixed sequence comprises a random sequence of about 30 to about 50 nucleotides.

The core SELEX™ method has been modified to achieve a number of specific objectives. For example, U.S. Pat. No. 5,707,796 describes the use of SELEX™ in conjunction with gel electrophoresis to select nucleic acid molecules with specific structural characteristics, such as bent DNA. U.S. Pat. No. 5,763,177 describes SELEX™ based methods for selecting nucleic acid ligands containing photoreactive groups capable of binding and/or photocrosslinking to and/or photoinactivating a target molecule. U.S. Pat. No. 5,567,588 and U.S. Pat. No. 5,861,254 describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705,337 describes methods for covalently linking a ligand to its target.

SELEX™ can also be used to obtain nucleic acid ligands that bind to more than one site on the target molecule, and to obtain nucleic acid ligands that include non-nucleic acid species that bind to specific sites on the target. SELEX™ provides means for isolating and identifying nucleic acid ligands which bind to any envisionable target, including large and small biomolecules such as nucleic acid-binding proteins and proteins not known to bind nucleic acids as part of their biological function as well as cofactors and other small molecules. For example, U.S. Pat. No. 5,580,737 discloses nucleic acid sequences identified through SELEX™ which are capable of binding with high affinity to caffeine and the closely related analog, theophylline.

Counter-SELEX™ is a method for improving the specificity of nucleic acid ligands to a target molecule by eliminating nucleic acid ligand sequences with cross-reactivity to one or more non-target molecules. Counter-SELEX™ is comprised of the steps of: (a) preparing a candidate mixture of nucleic acids; (b) contacting the candidate mixture with the target, wherein nucleic acids having an increased affinity to the target relative to the candidate mixture may be partitioned from the remainder of the candidate mixture; (c) partitioning the increased affinity nucleic acids from the remainder of the candidate mixture; (d) dissociating the increased affinity nucleic acids from the target; e) contacting the increased affinity nucleic acids with one or more non-target molecules such that nucleic acid ligands with specific affinity for the non-target molecule(s) are removed; and (f) amplifying the nucleic acids with specific affinity only to the target molecule to yield a mixture of nucleic acids enriched for nucleic acid sequences with a relatively higher affinity and specificity for binding to the target molecule. As described above for SELEX™ cycles of selection and amplification are repeated as necessary until a desired goal is achieved.

One potential problem encountered in the use of nucleic acids as therapeutics and vaccines is that oligonucleotides in their phosphodiester form may be quickly degraded in body fluids by intracellular and extracellular enzymes such as endonucleases and exonucleases before the desired effect is manifest. The SELEX™ method thus encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX™-identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-O-methyl (2'-OMe) substituents.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Modifications to generate oligonucleotide populations which are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, and unusual base-pairing combinations such as the isobases isocytidine and isoguanosine. Modifications can also include 3' and 5' modifications such as capping.

In one embodiment, oligonucleotides are provided in which the P(O)O group is replaced by P(O)S ("thioate"), P(S)S ("dithioate"), P(O)NR$_2$ ("amidate"), P(O)R, P(O)OR', CO or CH$_2$ ("formacetal") or 3'-amine (—NH—CH$_2$—CH$_2$—), wherein each R or R' is independently H or substituted or unsubstituted alkyl. Linkage groups can be attached to adjacent nucleotides through an —O—, —N—, or —S— linkage. Not all linkages in the oligonucleotide are required to be identical. As used herein, the term phosphorothioate encompasses one or more non-bridging oxygen atoms in a phosphodiester bond replaced by one or more sulfur atoms.

In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described, e.g., in Sproat, et al., Nucl. Acid Res. 19:733-738 (1991); Cotten, et al., Nucl. Acid Res. 19:2629-2635 (1991); and Hobbs, et al., Biochemistry 12:5138-5145 (1973). Other modifications are known to one of ordinary skill in the art. Such modifications may be pre-SELEX™ process modifications or post-SELEX™ process modifications (modification of previously identified unmodified ligands) or may be made by incorporation into the SELEX™ process.

Pre-SELEX™ process modifications or those made by incorporation into the SELEX™ process yield nucleic acid ligands with both specificity for their SELEX™ target and improved stability, e.g., in vivo stability. Post-SELEX™ process modifications made to nucleic acid ligands may result in improved stability, e.g., in vivo stability without adversely affecting the binding capacity of the nucleic acid ligand.

The SELEX™ method encompasses combining selected oligonucleotides with other selected oligonucleotides and non-oligonucleotide functional units as described in U.S. Pat. No. 5,637,459 and U.S. Pat. No. 5,683,867. The SELEX™ method further encompasses combining selected nucleic acid ligands with lipophilic or non-immunogenic high molecular weight compounds in a diagnostic or therapeutic complex, as described, e.g., in U.S. Pat. No. 6,011,020, U.S. Pat. No. 6,051,698, and PCT Publication No. WO 98/18480. These patents and applications teach the combination of a broad array of shapes and other properties, with the efficient amplification and replication properties of oligonucleotides, and with the desirable properties of other molecules.

The identification of nucleic acid ligands to small, flexible peptides via the SELEX™ method has also been explored. Small peptides have flexible structures and usually exist in solution in an equilibrium of multiple conformers, and thus it was initially thought that binding affinities may be limited by the conformational entropy lost upon binding a flexible peptide. However, the feasibility of identifying nucleic acid ligands to small peptides in solution was demonstrated in U.S. Pat. No. 5,648,214. In this patent, high affinity RNA nucleic acid ligands to substance P, an 11 amino acid peptide, were identified.

The aptamers with specificity and binding affinity to the target(s) of the present invention are typically selected by the SELEX™ process as described herein. As part of the SELEX™ process, the sequences selected to bind to the target are then optionally minimized to determine the minimal sequence having the desired binding affinity. The selected sequences and/or the minimized sequences are optionally optimized by performing random or directed mutagenesis of the sequence to increase binding affinity or alternatively to determine which positions in the sequence are essential for binding activity. Additionally, selections can be performed with sequences incorporating modified nucleotides to stabilize the aptamer molecules against degradation in vivo.

2' Modified SELEX™

In order for an aptamer to be suitable for use as a therapeutic, it is preferably inexpensive to synthesize, safe and stable in vivo. Wild-type RNA and DNA aptamers are typically not stable in vivo because of their susceptibility to degradation by nucleases. Resistance to nuclease degradation can be greatly increased by the incorporation of modifying groups at the 2'-position.

Fluoro and amino groups have been successfully incorporated into oligonucleotide pools from which aptamers have been subsequently selected. However, these modifications greatly increase the cost of synthesis of the resultant aptamer, and may introduce safety concerns in some cases because of the possibility that the modified nucleotides could be recycled into host DNA by degradation of the modified oligonucleotides and subsequent use of the nucleotides as substrates for DNA synthesis.

Aptamers that contain 2'-O-methyl ("2"-OMe") nucleotides, as provided herein, overcome many of these drawbacks. Oligonucleotides containing 2'-OMe nucleotides are nuclease-resistant and inexpensive to synthesize. Although 2'-OMe nucleotides are ubiquitous in biological systems, natural polymerases do not accept 2'-OMe NTPs as substrates under physiological conditions, thus there are no safety concerns over the recycling of 2'-OMe nucleotides into host DNA. The SELEX™ method used to generate 2'-modified aptamers is described, e.g., in U.S. Provisional Patent Application Ser. No. 60/430,761, filed Dec. 3, 2002, U.S. Provisional Patent Application Ser. No. 60/487,474, filed Jul. 15, 2003, U.S. Provisional Patent Application Ser. No. 60/517,039, filed Nov. 4, 2003, U.S. patent application Ser. No. 10/729,581, filed Dec. 3, 2003, and U.S. patent application Ser. No. 10/873,856, filed Jun. 21, 2004, entitled "Method for in vitro Selection of 2'-O-methyl Substituted Nucleic Acids", each of which is herein incorporated by reference in its entirety.

The present invention includes aptamers that bind to PSMA which contain modified nucleotides (e.g., nucleotides which have a modification at the 2' position) to make the oligonucleotide more stable than the unmodified oligonucleotide to enzymatic and chemical degradation as well as thermal and physical degradation. Although there are several examples of 2'-OMe containing aptamers in the literature (see, e.g., Green et al., Current Biology 2, 683-695, 1995)

these were generated by the in vitro selection of libraries of modified transcripts in which the C and U residues were 2'-fluoro (2'-F) substituted and the A and G residues were 2'-OH. Once functional sequences were identified then each A and G residue was tested for tolerance to 2'-OMe substitution, and the aptamer was re-synthesized having all A and G residues which tolerated 2'-OMe substitution as 2'-OMe residues. Most of the A and G residues of aptamers generated in this two-step fashion tolerate substitution with 2'-OMe residues, although, on average, approximately 20% do not. Consequently, aptamers generated using this method tend to contain from two to four 2'-OH residues, and stability and cost of synthesis are compromised as a result. By incorporating modified nucleotides into the transcription reaction which generate stabilized oligonucleotides used in oligonucleotide pools from which aptamers are selected and enriched by SELEX™ (and/or any of its variations and improvements, including those described herein), the methods of the present invention eliminate the need for stabilizing the selected aptamer oligonucleotides (e.g., by resynthesizing the aptamer oligonucleotides with modified nucleotides).

In one embodiment, the present invention provides aptamers comprising combinations of 2'-OH, 2'-F, 2'-deoxy, and 2'-OMe modifications of the ATP, GTP, CTP, TTP, and UTP nucleotides. In another embodiment, the present invention provides aptamers comprising combinations of 2'-OH, 2'-F, 2'-deoxy, 2'-OMe, 2'-NH$_2$, and 2'-methoxyethyl modifications of the ATP, GTP, CTP, TTP, and UTP nucleotides. In another embodiment, the present invention provides aptamers comprising $5^6$ combinations of 2'-OH, 2'-F, 2'-deoxy, 2'-OMe, 2'-NH$_2$, and 2'-methoxyethyl modifications of the ATP, GTP, CTP, TTP, and UTP nucleotides.

2' modified aptamers of the invention are created using modified polymerases, e.g., a modified T7 polymerase, having a rate of incorporation of modified nucleotides having bulky substituents at the furanose 2' position that is higher than that of wild-type polymerases. For example, a mutant T7 polymerase (Y639F) in which the tyrosine residue at position 639 has been changed to phenylalanine readily utilizes 2'deoxy, 2'amino-, and 2'fluoro-nucleotide triphosphates (NTPs) as substrates and has been widely used to synthesize modified RNAs for a variety of applications. However, this mutant T7 polymerase reportedly can not readily utilize (i.e., incorporate) NTPs with bulky 2'-substituents such as 2'-OMe or 2'-azido (2'-N$_3$) substituents. For incorporation of bulky 2' substituents, a double T7 polymerase mutant (Y639F/H784A) having the histidine at position 784 changed to an alanine residue in addition to the Y639F mutation has been described and has been used in limited circumstances to incorporate modified pyrimidine NTPs. See Padilla, R. and Sousa, R., Nucleic Acids Res., 2002, 30(24): 138. A mutant T7 polymerase (H784A) having the histidine at position 784 changed to an alanine residue has also been described. Padilla et al., Nucleic Acids Research, 2002, 30: 138. In both the Y639F/H784A double mutant and H784A mutant T7 polymerases, the change to a smaller amino acid residue such as alanine allows for the incorporation of bulkier nucleotide substrates, e.g., 2'-OMe substituted nucleotides.

Generally, it has been found that under the conditions disclosed herein, the Y693F mutant can be used for the incorporation of all 2'-OMe substituted NTPs except GTP and the Y639F/H784A double mutant can be used for the incorporation of all 2'-OMe substituted NTPs including GTP. It is expected that the H784A mutant possesses properties similar to the Y639F and the Y639F/H784A mutants when used under the conditions disclosed herein.

2'-modified oligonucleotides may be synthesized entirely of modified nucleotides, or with a subset of modified nucleotides. The modifications can be the same or different. All nucleotides may be modified, and all may contain the same modification. All nucleotides may be modified, but contain different modifications, e.g., all nucleotides containing the same base may have one type of modification, while nucleotides containing other bases may have different types of modification. All purine nucleotides may have one type of modification (or are unmodified), while all pyrimidine nucleotides have another, different type of modification (or are unmodified). In this way, transcripts, or pools of transcripts are generated using any combination of modifications, including for example, ribonucleotides (2'-OH), deoxyribonucleotides (2'-deoxy), 2'-F, and 2'-OMe nucleotides. A transcription mixture containing 2'-OMe C and U and 2'-OH A and G is referred to as a "rRmY" mixture and aptamers selected therefrom are referred to as "rRmY" aptamers. A transcription mixture containing deoxy A and G and 2'-OMe U and C is referred to as a "dRmY" mixture and aptamers selected therefrom are referred to as "dRmY" aptamers. A transcription mixture containing 2'-OMe A, C, and U, and 2'-OH G is referred to as a "rGmH" mixture and aptamers selected therefrom are referred to as "rGmH" aptamers. A transcription mixture alternately containing 2'-OMe A, C, U and G and 2'-OMe A, U and C and 2'-F G is referred to as a "alternating" mixture and aptamers selected therefrom are referred to as "alternating mixture" aptamers. A transcription mixture containing 2'-OMe A, U, C, and G, where up to 10% of the G's are ribonucleotides is referred to as a "r/mGmH" mixture and aptamers selected therefrom are referred to as "r/mGmH" aptamers. A transcription mixture containing 2'-OMe A, U, and C, and 2'-F G is referred to as a "fGmH" mixture and aptamers selected therefrom are referred to as "fGmH" aptamers. A transcription mixture containing 2'-OMe A, U, and C, and deoxy G is referred to as a "dGmH" mixture and aptamers selected therefrom are referred to as "dGmH" aptamers. A transcription mixture containing deoxy A, and 2'-OMe C, G and U is referred to as a "dAmB" mixture and aptamers selected therefrom are referred to as "dAmB" aptamers, and a transcription mixture containing all 2'-OH nucleotides is referred to as a "rN" mixture and aptamers selected therefrom are referred to as "rN" or "rRrY" aptamers. A "mRmY" aptamer is one containing all 2'-O-methyl nucleotides and is usually derived from a r/mGmH oligonucleotide by post-SELEX™ replacement, when possible, of any 2'-OH Gs with 2'-OMe Gs.

A preferred embodiment includes any combination of 2'-OH, 2'-deoxy and 2'-OMe nucleotides. A more preferred embodiment includes any combination of 2'-deoxy and 2'-OMe nucleotides. An even more preferred embodiment is with any combination of 2'-deoxy and 2'-OMe nucleotides in which the pyrimidines are 2'-OMe (such as dRmY, mRmY or dGmH).

Incorporation of modified nucleotides into the aptamers of the invention is accomplished before (pre-) the selection process (e.g., a pre-SELEX™ process modification). Optionally, aptamers of the invention in which modified nucleotides have been incorporated by pre-SELEX™ process modification can be further modified by post-SELEX™ process modification (i.e., a post-SELEX™ process modification after a pre-SELEX™ modification). Pre-SELEX™ process modifications yield modified nucleic acid ligands with specificity for the SELEX™ target and also improved in vivo stability. Post-SELEX™ process modifications, i.e., modification (e.g., truncation, deletion, substitution or additional nucleotide modifications of previously identified ligands having nucleotides incorporated by pre-SELEX™ process modification) can result in a further improvement of in vivo stability without adversely affecting the binding capacity of the nucleic acid ligand having nucleotides incorporated by pre-SELEX™ process modification.

To generate pools of 2'-modified (e.g., 2'-OMe) RNA transcripts in conditions under which a polymerase accepts 2'-modified NTPs the preferred polymerase is the Y693F/H784A double mutant or the Y693F mutant. Other polymerases, particularly those that exhibit a high tolerance for bulky 2'-substituents, may also be used in the present invention. Such polymerases can be screened for this capability by assaying their ability to incorporate modified nucleotides under the transcription conditions disclosed herein.

A number of factors have been determined to be important for the transcription conditions useful in the methods disclosed herein. For example, increases in the yields of modified transcript are observed when a leader sequence is incorporated into the 5' end of a fixed sequence at the 5' end of the DNA transcription template, such that at least about the first 6 residues of the resultant transcript are all purines.

Another important factor in obtaining transcripts incorporating modified nucleotides is the presence or concentration of 2'-OH GTP. Transcription can be divided into two phases: the first phase is initiation, during which an NTP is added to the 3'-hydroxyl end of GTP (or another substituted guanosine) to yield a dinucleotide which is then extended by about 10-12 nucleotides; the second phase is elongation, during which transcription proceeds beyond the addition of the first about 10-12 nucleotides. It has been found that small amounts of 2'-OH GTP added to a transcription mixture containing an excess of 2'-OMe GTP are sufficient to enable the polymerase to initiate transcription using 2'-OH GTP, but once transcription enters the elongation phase the reduced discrimination between 2'-OMe and 2'-OH GTP, and the excess of 2'-OMe GTP over 2'-OH GTP allows the incorporation of principally the 2'-OMe GTP.

Another important factor in the incorporation of 2'-OMe substituted nucleotides into transcripts is the use of both divalent magnesium and manganese in the transcription mixture. Different combinations of concentrations of magnesium chloride and manganese chloride have been found to affect yields of 2'-O-methylated transcripts, the optimum concentration of the magnesium and manganese chloride being dependent on the concentration in the transcription reaction mixture of NTPs which complex divalent metal ions. To obtain the greatest yields of maximally 2' substituted O-methylated transcripts (i.e., all A, C, and U and about 90% of G nucleotides), concentrations of approximately 5 mM magnesium chloride and 1.5 mM manganese chloride are preferred when each NTP is present at a concentration of 0.5 mM. When the concentration of each NTP is 1.0 mM, concentrations of approximately 6.5 mM magnesium chloride and 2.0 mM manganese chloride are preferred. When the concentration of each NTP is 2.0 mM, concentrations of approximately 9.6 mM magnesium chloride and 2.9 mM manganese chloride are preferred. In any case, departures from these concentrations of up to two-fold still give significant amounts of modified transcripts.

Priming transcription with GMP or guanosine is also important. This effect results from the specificity of the polymerase for the initiating nucleotide. As a result, the 5'-terminal nucleotide of any transcript generated in this fashion is likely to be 2'-OH G. The preferred concentration of GMP (or guanosine) is 0.5 mM and even more preferably 1 mM. It has also been found that including PEG, preferably PEG-8000, in the transcription reaction is useful to maximize incorporation of modified nucleotides.

For maximum incorporation of 2'-OMe ATP (100%), UTP (100%), CTP (100%) and GTP (~90%) ("r/mGmH") into transcripts the following conditions are preferred: HEPES buffer 200 mM, DTT 40 mM, spermidine 2 mM, PEG-8000 10% (w/v), Triton X-100 0.01% (w/v), MgCl$_2$ 5 mM (6.5 mM where the concentration of each 2'-OMe NTP is 1.0 mM), MnCl$_2$ 1.5 mM (2.0 mM where the concentration of each 2'-OMe NTP is 1.0 mM), 2'-OMe NTP (each) 500 µM (more preferably, 1.0 mM), 2'-OH GTP 30 µM, 2'-OH GMP 500 µM, pH 7.5, Y639F/H784A T7 RNA Polymerase 15 units/ml, inorganic pyrophosphatase 5 units/ml, and an all-purine leader sequence of at least 8 nucleotides long. As used herein, one unit of the Y639F/H784A mutant T7 RNA polymerase (or any other mutant T7 RNA polymerase specified herein) is defined as the amount of enzyme required to incorporate 0.1 nmole of 2'-OMe NTPs into transcripts under the r/mGmH conditions. As used herein, one unit of inorganic pyrophosphatase is defined as the amount of enzyme that will liberate 1.0 mole of inorganic orthophosphate per minute at pH 7.2 and 25° C.

For maximum incorporation (100%) of 2'-OMe ATP, UTP and CTP ("rGmH") into transcripts the following conditions are preferred: HEPES buffer 200 mM, DTT 40 mM, spermidine 2 mM, PEG-8000 10% (w/v), Triton X-100 0.01% (w/v), MgCl$_2$ 5 mM (9.6 mM where the concentration of each 2'-OMe NTP is 2.0 mM), MnCl$_2$ 1.5 mM (2.9 mM where the concentration of each 2'-OMe NTP is 2.0 mM), 2'-OMe NTP (each) 500 µM (more preferably, 2.0 mM), pH 7.5, Y639F T7 RNA Polymerase 15 units/ml, inorganic pyrophosphatase 5 units/ml, and an all-purine leader sequence of at least 8 nucleotides long.

For maximum incorporation (100%) of 2'-OMe UTP and CTP ("rRmY") into transcripts the following conditions are preferred: HEPES buffer 200 mM, DTT 40 mM, spermidine 2 mM, PEG-8000 10% (w/v), Triton X-100 0.01% (w/v), MgCl$_2$ 5 mM (9.6 mM where the concentration of each 2'-OMe NTP is 2.0 mM), MnCl$_2$ 1.5 mM (2.9 mM where the concentration of each 2'-OMe NTP is 2.0 mM), 2'-OMe NTP (each) 500 µM (more preferably, 2.0 mM), pH 7.5, Y639F/H784A T7 RNA Polymerase 15 units/ml, inorganic pyrophosphatase 5 units/ml, and an all-purine leader sequence of at least 8 nucleotides long.

For maximum incorporation (100%) of deoxy ATP and GTP and 2'-OMe UTP and CTP ("dRmY") into transcripts the following conditions are preferred: HEPES buffer 200 mM, DTT 40 mM, spermine 2 mM, spermidine 2 mM, PEG-8000 10% (w/v), Triton X-100 0.01% (w/v), MgCl$_2$ 9.6 mM, MnCl$_2$ 2.9 mM, 2'-OMe NTP (each) 2.0 mM, pH 7.5, Y639F T7 RNA Polymerase 15 units/ml, inorganic pyrophosphatase 5 units/ml, and an all-purine leader sequence of at least 8 nucleotides long.

For maximum incorporation (100%) of 2'-OMe ATP, UTP and CTP and 2'-F GTP ("fGmH") into transcripts the following conditions are preferred: HEPES buffer 200 mM, DTT 40 mM, spermidine 2 mM, PEG-8000 10% (w/v), Triton X-100 0.01% (w/v), MgCl$_2$ 9.6 mM, MnCl$_2$ 2.9 mM, 2'-OMe NTP (each) 2.0 mM, pH 7.5, Y639F T7 RNA Polymerase 15 units/ml, inorganic pyrophosphatase 5 units/ml, and an all-purine leader sequence of at least 8 nucleotides long.

For maximum incorporation (100%) of deoxy ATP and 2'-OMe UTP, GTP and CTP ("dAmB") into transcripts the following conditions are preferred: HEPES buffer 200 mM, DTT 40 mM, spermidine 2 mM, PEG-8000 10% (w/v), Triton X-100 0.01% (w/v), MgCl$_2$ 9.6 mM, MnCl$_2$ 2.9 mM, 2'-OMe NTP (each) 2.0 mM, pH 7.5, Y639F T7 RNA Polymerase 15 units/ml, inorganic pyrophosphatase 5 units/ml, and an all-purine leader sequence of at least 8 nucleotides long.

For each of the above (a) transcription is preferably performed at a temperature of from about 20° C. to about 50° C., preferably from about 30° C. to 45° C., and more preferably at about 37° C. for a period of at least two hours and (b) 50-300 nM of a double stranded DNA transcription template is used (200 nM template is used in round 1 to increase diversity (300 nM template is used in dRmY transcriptions)), and for subsequent rounds approximately 50 nM, a 1/10 dilution of an optimized PCR reaction, using conditions described herein, is used). The preferred DNA transcription templates are described below (where ARC254 and ARC256 transcribe under all 2'-OMe conditions and ARC255 transcribes under rRmY conditions).

```
ARC254
5'-CATCGATGCTAGTCGTAACGATCCNNNNNNNNNNNN  SEQ ID NO 1
NNNNNNNNNNNNNNNNNNNCGAGAACGUCTCTCCTCTCCC
TATAGTGAGTCGTATTA-3'

ARC255
5'-CATGCATCGCGACTGACTAGCCGNNNNNNNNNNNNN  SEQ ID NO 2
NNNNNNNNNNNNNNNNNNGTAGAACGTTCTCTCCTCTCCC
TATAGTGAGTCGTATTA-3'

ARC256
5'-CATCGATCGATCGATCGACAGCGNNNNNNNNNNNNN  SEQ ID NO 3
NNNNNNNNNNNNNNNNNNGTAGAACGTTCTCTCCTCTCCC
TATAGTGAGTCGTATTA-3'
```

Under rN transcription conditions of the present invention, the transcription reaction mixture comprises 2'-OH adenosine triphosphates (ATP), 2'-OH guanosine triphosphates (GTP), 2'-OH cytidine triphosphates (CTP), and 2'-OH uridine triphosphates (UTP). The modified oligonucleotides produced using the rN transcription mixtures of the present invention comprise substantially all 2'-OH adenosine, 2'-OH guanosine, 2'-OH cytidine, and 2'-OH uridine. In a preferred embodiment of rN transcription, the resulting modified oligonucleotides comprise a sequence where at least 80% of all adenosine nucleotides are 2'-OH adenosine, at least 80% of all guanosine nucleotides are 2'-OH guanosine, at least 80% of all cytidine nucleotides are 2'-OH cytidine, and at least 80% of all uridine nucleotides are 2'-OH uridine. In a more preferred embodiment of rN transcription, the resulting modified oligonucleotides of the present invention comprise a sequence where at least 90% of all adenosine nucleotides are 2'-OH adenosine, at least 90% of all guanosine nucleotides are 2'-OH guanosine, at least 90% of all cytidine nucleotides are 2'-OH cytidine, and at least 90% of all uridine nucleotides are 2'-OH uridine. In a most preferred embodiment of rN transcription, the modified oligonucleotides of the present invention comprise a sequence where 100% of all adenosine nucleotides are 2'-OH adenosine, 100% of all guanosine nucleotides are 2'-OH guanosine, 100% of all cytidine nucleotides are 2'-OH cytidine, and 100% of all uridine nucleotides are 2'-OH uridine.

Under rRmY transcription conditions of the present invention, the transcription reaction mixture comprises 2'-OH adenosine triphosphates, 2'-OH guanosine triphosphates, 2'-O-methyl cytidine triphosphates, and 2'-O-methyl uridine triphosphates. The modified oligonucleotides produced using the rRmY transcription mixtures of the present invention comprise substantially all 2'-OH adenosine, 2'-OH guanosine, 2'-O-methyl cytidine and 2'-O-methyl uridine. In a preferred embodiment, the resulting modified oligonucleotides comprise a sequence where at least 80% of all adenosine nucleotides are 2'-OH adenosine, at least 80% of all guanosine nucleotides are 2'-OH guanosine, at least 80% of all cytidine nucleotides are 2'-O-methyl cytidine and at least 80% of all uridine nucleotides are 2'-O-methyl uridine. In a more preferred embodiment, the resulting modified oligonucleotides comprise a sequence where at least 90% of all adenosine nucleotides are 2'-OH adenosine, at least 90% of all guanosine nucleotides are 2'-OH guanosine, at least 90% of all cytidine nucleotides are 2'-O-methyl cytidine and at least 90% of all uridine nucleotides are 2'-O-methyl uridine In a most preferred embodiment, the resulting modified oligonucleotides comprise a sequence where 100% of all adenosine nucleotides are 2'-OH adenosine, 100% of all guanosine nucleotides are 2'-OH guanosine, 100% of all cytidine nucleotides are 2'-O-methyl cytidine and 100% of all uridine nucleotides are 2'-O-methyl uridine.

Under dRmY transcription conditions of the present invention, the transcription reaction mixture comprises 2'-deoxy adenosine triphosphates, 2'-deoxy guanosine triphosphates, 2'-O-methyl cytidine triphosphates, and 2'-O-methyl uridine triphosphates. The modified oligonucleotides produced using the dRmY transcription conditions of the present invention comprise substantially all 2'-deoxy adenosine, 2'-deoxy guanosine, 2'-O-methyl cytidine, and 2'-O-methyl uridine. In a preferred embodiment, the resulting modified oligonucleotides of the present invention comprise a sequence where at least 80% of all adenosine nucleotides are 2'-deoxy adenosine, at least 80% of all guanosine nucleotides are 2'-deoxy guanosine, at least 80% of all cytidine nucleotides are 2'-O-methyl cytidine, and at least 80% of all uridine nucleotides are 2'-O-methyl uridine. In a more preferred embodiment, the resulting modified oligonucleotides of the present invention comprise a sequence where at least 90% of all adenosine nucleotides are 2'-deoxy adenosine, at least 90% of all guanosine nucleotides are 2'-deoxy guanosine, at least 90% of all cytidine nucleotides are 2'-O-methyl cytidine, and at least 90% of all uridine nucleotides are 2'-O-methyl uridine. In a most preferred embodiment, the resulting modified oligonucleotides of the present invention comprise a sequence where 100% of all adenosine nucleotides are 2'-deoxy adenosine, 100% of all guanosine nucleotides are 2'-deoxy guanosine, 100% of all cytidine nucleotides are 2'-O-methyl cytidine, and 100% of all uridine nucleotides are 2'-O-methyl uridine.

Under rGmH transcription conditions of the present invention, the transcription reaction mixture comprises 2'-OH guanosine triphosphates, 2'-O-methyl cytidine triphosphates, 2'-O-methyl uridine triphosphates, and 2'-O-methyl adenosine triphosphates. The modified oligonucleotides produced using the rGmH transcription mixtures of the present invention comprise substantially all 2'-OH guanosine, 2'-O-methyl cytidine, 2'-O-methyl uridine, and 2'-O-methyl adenosine. In a preferred embodiment, the resulting modified oligonucleotides comprise a sequence where at least 80% of all guanosine nucleotides are 2'-OH guanosine, at least 80% of all cytidine nucleotides are 2'-O-methyl cytidine, at least 80% of all uridine nucleotides are 2'-O-methyl uridine, and at least 80% of all adenosine nucleotides are 2'-O-methyl adenosine. In a more preferred embodiment, the resulting modified oligonucleotides comprise a sequence where at least 90% of all guanosine nucleotides are 2'-OH guanosine, at least 90% of all cytidine nucleotides are 2'-O-methyl cytidine, at least 90% of all uridine nucleotides are 2'-O-methyl uridine, and at least 90% of all adenosine nucleotides are 2'-O-methyl adenosine. In a most preferred embodiment, the resulting modified oligonucleotides comprise a sequence where 100% of all guanosine nucleotides are 2'-OH guanosine, 100% of all cytidine nucleotides are 2'-O-methyl cytidine, 100% of all uridine nucleotides are 2'-O-methyl uridine, and 100% of all adenosine nucleotides are 2'-O-methyl adenosine.

Under r/mGmH transcription conditions of the present invention, the transcription reaction mixture comprises 2'-O-methyl adenosine triphosphate, 2'-O-methyl cytidine triphosphate, 2'-O-methyl guanosine triphosphate, 2'-O-methyl uridine triphosphate and 2'-OH guanosine triphosphate. The resulting modified oligonucleotides produced using the r/mGmH transcription mixtures of the present invention comprise substantially all 2'-O-methyl adenosine, 2'-O-methyl cytidine, 2'-O-methyl guanosine, and 2'-O-methyl uridine, wherein the population of guanosine nucleotides has a maximum of about 10% 2'-OH guanosine. In a preferred embodiment, the resulting r/mGmH modified oligonucleotides of the present invention comprise a sequence where at least 80% of all adenosine nucleotides are 2'-O-methyl adenosine, at least 80% of all cytidine nucleotides are 2'-O-methyl cytidine, at least 80% of all guanosine nucleotides are 2'-O-methyl guanosine, at least 80% of all uridine nucleotides are 2'-O-methyl uridine, and no more than about 10% of all guanosine nucleotides are 2'-OH guanosine. In a more preferred embodiment, the resulting modified oligonucleotides comprise a sequence where at least 90% of all adenosine nucleotides are 2'-O-methyl adenosine, at least 90% of all cytidine nucleotides are 2'-O-methyl cytidine, at least 90% of all guanosine nucleotides are 2'-O-methyl guanosine, at least 90% of all uridine nucleotides are 2'-O-methyl uridine, and no more than about 10% of all guanosine nucleotides are 2'-OH guanosine. In a most preferred embodiment, the resulting modified oligonucleotides comprise a sequence where 100% of all adenosine nucleotides are 2'-O-methyl adenosine, 100% of all cytidine nucleotides are 2'-O-methyl cytidine, 90% of all guanosine nucleotides are 2'-O-methyl guanosine, and 100% of all uridine nucleotides are 2'-O-methyl uridine, and no more than about 10% of all guanosine nucleotides are 2'-OH guanosine.

Under fGmH transcription conditions of the present invention, the transcription reaction mixture comprises 2'-O-methyl adenosine triphosphates, 2'-O-methyl uridine triphosphates, 2'-O-methyl cytidine triphosphates, and 2'-F guanosine triphosphates. The modified oligonucleotides produced using the fGmH transcription conditions of the present invention comprise substantially all 2'-O-methyl adenosine, 2'-O-methyl uridine, 2'-O-methyl cytidine, and 2'-F guanosine. In a preferred embodiment, the resulting modified oligonucleotides comprise a sequence where at least 80% of all adenosine nucleotides are 2'-O-methyl adenosine, at least 80% of all uridine nucleotides are 2'-O-methyl uridine, at least 80% of all cytidine nucleotides are 2'-O-methyl cytidine, and at least 80% of all guanosine nucleotides are 2'-F guanosine. In a more preferred embodiment, the resulting modified oligonucleotides comprise a sequence where at least 90% of all adenosine nucleotides are 2'-O-methyl adenosine, at least 90% of all uridine nucleotides are 2'-O-methyl uridine, at least 90% of all cytidine nucleotides are 2'-O-methyl cytidine, and at least 90% of all guanosine nucleotides are 2'-F guanosine. In a most preferred embodiment, the resulting modified oligonucleotides comprise a sequence where 100% of all adenosine nucleotides are 2'-O-methyl adenosine, 100% of all uridine nucleotides are 2'-O-methyl uridine, 100% of all cytidine nucleotides are 2'-O-methyl cytidine, and 100% of all guanosine nucleotides are 2'-F guanosine.

Under dAmB transcription conditions of the present invention, the transcription reaction mixture comprises 2'-deoxy adenosine triphosphates, 2'-O-methyl cytidine triphosphates, 2'-O-methyl guanosine triphosphates, and 2'-O-methyl uridine triphosphates. The modified oligonucleotides produced using the dAmB transcription mixtures of the present invention comprise substantially all 2'-deoxy adenosine, 2'-O-methyl cytidine, 2'-O-methyl guanosine, and 2'-O-methyl uridine. In a preferred embodiment, the resulting modified oligonucleotides comprise a sequence where at least 80% of all adenosine nucleotides are 2'-deoxy adenosine, at least 80% of all cytidine nucleotides are 2'-O-methyl cytidine, at least 80% of all guanosine nucleotides are 2'-O-methyl guanosine, and at least 80% of all uridine nucleotides are 2'-O-methyl uridine. In a more preferred embodiment, the resulting modified oligonucleotides comprise a sequence where at least 90% of all adenosine nucleotides are 2'-deoxy adenosine, at least 90% of all cytidine nucleotides are 2'-O-methyl cytidine, at least 90% of all guanosine nucleotides are 2'-O-methyl guanosine, and at least 90% of all uridine nucleotides are 2'-O-methyl uridine. In a most preferred embodiment, the resulting modified oligonucleotides of the present invention comprise a sequence where 100% of all adenosine nucleotides are 2'-deoxy adenosine, 100% of all cytidine nucleotides are 2'-O-methyl cytidine, 100% of all guanosine nucleotides are 2'-O-methyl guanosine, and 100% of all uridine nucleotides are 2'-O-methyl uridine.

In each case, the transcription products can then be used as the library in the SELEX™ process to identify aptamers and/or to determine a conserved motif of sequences that have binding specificity to a given target. The resulting sequences are already partially stabilized, eliminating this step from the process to arrive at an optimized aptamer sequence and giving a more highly stabilized aptamer as a result. Another advantage of the 2'-OMe SELEX™ process is that the resulting sequences are likely to have fewer 2'-OH nucleotides required in the sequence, possibly none. To the extent 2'OH nucleotides remain they can be removed by performing post-SELEX™ modifications.

As described below, lower but still useful yields of transcripts fully incorporating 2' substituted nucleotides can be obtained under conditions other than the optimized conditions described above. For example, variations to the above transcription conditions include:

The HEPES buffer concentration can range from 0 to 1 M. The present invention also contemplates the use of other buffering agents having a pKa between 5 and 10 including, for example, Tris-hydroxymethyl-aminomethane.

The DTT concentration can range from 0 to 400 mM. The methods of the present invention also provide for the use of other reducing agents including, for example, mercaptoethanol.

The spermidine and/or spermine concentration can range from 0 to 20 mM.

The PEG-8000 concentration can range from 0 to 50% (w/v). The methods of the present invention also provide for the use of other hydrophilic polymer including, for example, other molecular weight PEG or other polyalkylene glycols.

The Triton X-100 concentration can range from 0 to 0.1% (w/v). The methods of the present invention also provide for the use of other non-ionic detergents including, for example, other detergents, including other Triton-X detergents.

The $MgCl_2$ concentration can range from 0.5 mM to 50 mM. The $MnCl_2$ concentration can range from 0.15 mM to 15 mM. Both $MgCl_2$ and $MnCl_2$ must be present within the ranges described and in a preferred embodiment are present in about a 10 to about 3 ratio of $MgCl_2:MnCl_2$, preferably, the ratio is about 3-5:1, more preferably, the ratio is about 3-4:1.

The 2'-OMe NTP concentration (each NTP) can range from 5 µM to 5 mM.

The 2'-OH GTP concentration can range from 0 μM to 300 μM.

The 2'-OH GMP concentration can range from 0 to 5 mM.

The pH can range from pH 6 to pH 9. The methods of the present invention can be practiced within the pH range of activity of most polymerases that incorporate modified nucleotides. In addition, the methods of the present invention provide for the optional use of chelating agents in the transcription reaction condition including, for example, EDTA, EGTA, and DTT.

Optimization Through Medicinal Chemistry

Aptamer Medicinal Chemistry is an aptamer improvement technique in which sets of variant aptamers are chemically synthesized. These sets of variants typically differ from the parent aptamer by the introduction of a single substituent, and differ from each other by the location of this substituent. These variants are then compared to each other and to the parent. Improvements in characteristics may be profound enough that the inclusion of a single substituent may be all that is necessary to achieve a particular therapeutic criterion.

Alternatively the information gleaned from the set of single variants may be used to design further sets of variants in which more than one substituent is introduced simultaneously. In one design strategy, all of the single substituent variants are ranked, the top 4 are chosen and all possible double (6), triple (4) and quadruple (1) combinations of these 4 single substituent variants are synthesized and assayed. In a second design strategy, the best single substituent variant is considered to be the new parent and all possible double substituent variants that include this highest-ranked single substituent variant are synthesized and assayed. Other strategies may be used, and these strategies may be applied repeatedly such that the number of substituents is gradually increased while continuing to identify further-improved variants.

Aptamer Medicinal Chemistry is most valuable as a method to explore the local, rather than the global, introduction of substituents. Because aptamers are discovered within libraries that are generated by transcription, any substituents that are introduced during the SELEX™ process must be introduced globally. For example, if it is desired to introduce phosphorothioate linkages between nucleotides then they can only be introduced at every A (or every G, C, T, U etc.) (globally substituted). Aptamers which require phosphorothioates at some As (or some G, C, T, U etc.) (locally substituted) but cannot tolerate it at other As cannot be readily discovered by this process.

The kinds of substituent that can be utilized by the Aptamer Medicinal Chemistry process are only limited by the ability to generate them as solid-phase synthesis reagents and introduce them into an oligomer synthesis scheme. The process is certainly not limited to nucleotides alone. Aptamer Medicinal Chemistry schemes may include substituents that introduce steric bulk, hydrophobicity, hydrophilicity, lipophilicity, lipophobicity, positive charge, negative charge, neutral charge, zwitterions, polarizability, nuclease-resistance, conformational rigidity, conformational flexibility, protein-binding characteristics, mass etc. Aptamer Medicinal Chemistry schemes may include base-modifications, sugar-modifications or phosphodiester linkage-modifications.

When considering the kinds of substituents that are likely to be beneficial within the context of a therapeutic aptamer, it may be desirable to introduce substitutions that fall into one or more of the following categories:

(1) Substituents already present in the body, e.g., 2'-deoxy, 2'-ribo, 2'-O-methyl purines or pyrimidines or 5-methyl cytosine.
(2) Substituents already part of an approved therapeutic, e.g., phosphorothioate-linked oligonucleotides.
(3) Substituents that hydrolyze or degrade to one of the above two categories, e.g., methylphosphonate-linked oligonucleotides.

The PSMA aptamers of the invention include aptamers developed through aptamer medicinal chemistry as described herein.

Therapeutic Aptamer-Drug Conjugates

In some embodiments, the therapeutic aptamer-drug conjugates of the invention have the following general formula: $(aptamer)_n$-linker-$(drug)_m$, where n is between 1 and 10 and m is between 0 and 20, particularly where n is between 1 and 10 and m is between 1 and 20. In particular embodiments, the aptamer is selected from the group consisting of: SEQ ID NOs 11-13, 15-26, 30-90, 122-165, 167 and 168. In some embodiments, the linker is a polyalkylene glycol, particularly a polyethylene glycol. In some embodiments, the drug is encapsulated, e.g. in a nanoparticle. In some embodiments, the linker is a liposome, dendrimer or comb polymer. In some embodiments, the drug is a cytotoxin. A plurality of aptamer species and drug species may be combined to yield a therapeutic composition.

In one embodiment, the therapeutic aptamer-drug conjugates of the invention are used in the targeted killing of tumor cells through aptamer-mediated delivery of cytotoxins. The efficiency of cell killing is improved if the target tumor marker is a marker that readily internalizes or recycles into the tumor cell. Aptamer-toxin molecules have been described generally in U.S. patent application Ser. No. 10/826,077, filed on Apr. 15, 2004,f U.S. patent application Ser. No. 10/600, 007 filed Jun. 18, 2003, U.S. Provisional Patent Application No. 60/390,042 filed Jun. 18, 2002 each of which is herein incorporated by reference in its entirety.

Tumor Cell-Targeting Aptamers: In this particular embodiment of the invention, the aptamer used in the aptamer-drug conjugate is selected for the ability to specifically recognize a marker that is expressed preferentially on the surface of tumor cells, but is relatively deficient from all normal tissues. Suitable target tumor markers include, but are not limited to, those listed in the Table A below.

TABLE A

| Aptamer Targets for Cytotoxin Delivery to Tumor Cells |
| --- |
| PSMA |
| PSCA |
| E-selectin |
| EphB2 (and other representative ephrins) |
| Cripto-1 |
| TENB2 (also known as TEMFF2) |
| ERBB2 receptor (HER2) |
| MUC1 |
| CD44v6 |
| CD6 |
| CD19 |
| CD20 |
| CD22 |
| CD23 |
| CD25 |
| CD30 |
| CD33 |
| CD56 |
| IL-2 receptor |

TABLE A-continued

Aptamer Targets for Cytotoxin Delivery to Tumor Cells

HLA-DR10β subunit
EGFRvIII
MN antigen (also known as CA IX or G250 antigen)
Caveolin-1
Nucleolin Aptamers that are specific for a given tumor cell marker, such as those listed in Table A, are generated using the SELEX™ process, as described above. SELEX™ has been successfully used to generate aptamers both to isolated, purified tumor cell surface proteins (e.g. tenascin C, MUC1, PSMA) and to tumor cells cultured in vitro (e.g. U251 (glioblastoma cell line), YPEN-1 (transformed prostate endothelial cell line)). In most cases, the extracellular portion of an identified tumor marker protein is recombinantly expressed, purified, and treated as a soluble protein through the SELEX™ process. In those cases where soluble protein domains cannot readily be produced, direct selection for binding to transformed cells (optionally negatively selecting against normal cell binding) yields aptamers that bind to tumor-specific markers.

Aptamer sequences initially identified through application of the SELEX™ process are optimized for both large-scale synthesis and in vivo applications through a progressive set of modifications. These modifications include, for example, (1) 5'- and 3'-terminal and internal deletions to reduce the size of the aptamer, (2) doped reselection for sequence modifications that increase the affinity or efficiency of target binding, (3) introduction of stabilizing base-pair changes that increase the stability of helical elements in the aptamer, (4) site-specific modifications of the 2'-ribose (e.g. 2'-hydroxyl→2'-O-methyl substitutions) and phosphate (e.g. phosphodiester→phosphorothioate substitutions) positions to both increase thermodynamic stability and to block nuclease attack in vivo, and (5) the addition of 5'- and/or 3'-caps (e.g. inverted 3'-deoxythymidine) to block attack by exonucleases. Aptamers generated through this process are typically 15-40 nucleotides long and exhibit serum half-lives greater than 10 hours.

To facilitate synthesis of the aptamer conjugate, reactive nucleophilic or electrophilic attachment points are introduced, for example, by directed solid phase synthesis or by post-synthesis modifications. A free amine is introduced at either the 5'- or 3'-end of the aptamer by incorporating the appropriate amino-modifier phosphoramidite at the end or beginning of solid phase synthesis respectively (e.g. 5'-amino modifier C6, Glen Research, Va.; or 3'-PT-Amino-Modifier C6 CPG Glen Research, Va., respectively). This amine serves directly as a nucleophilic attachment point, or alternatively, this amine is further converted into an electrophilic attachment point. For example, reaction with bis(sulfosuccinimidyl) suberate (BS[3]) or related reagents (Pierce, Ill.) yields a NHS ester suitable for conjugation with amine containing molecules. Alternatively, carboxylic acid groups are introduced by using 5'-Carboxy Modifier C10 (Glen Research, Va.) at the end of aptamer solid phase synthesis. Such carboxylates are then activated in situ with, e.g., 1-Ethyl-3-[3-dimethylaminopropyl]carbodiimide (EDC) to further react with nucleophiles.

Figure 4:
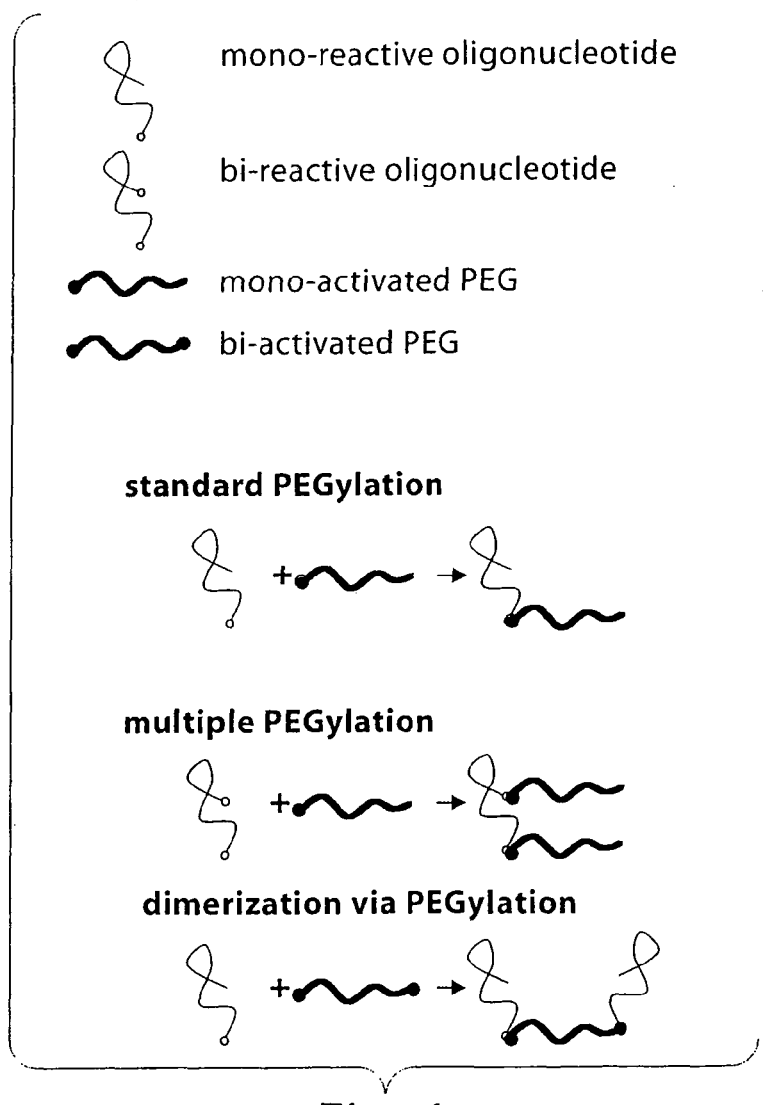
FIG. 4 is an illustration depicting various PEGylation strategies representing standard mono-PEGylation, multiple PEGylation, and oligomerization via PEGylation.

Multiple amines may be introduced at the 5'-end of the aptamer through solid phase synthesis in which a 5'-symmetric doubler is incorporated one or more times and followed with a terminal reaction with the 5'-amino modifier described above. Symmetric doubler phosphoramidites are commercially available (e.g. Glen Research, Va.). As shown in FIG. 4, two rounds of coupling with the symmetric doubler followed by amine capping yield an aptamer bearing four free reactive amines.

Cytotoxins: Drugs are attached to the linker such that their pharmacological activity is preserved in the conjugate or such that in vivo metabolism of the conjugate leads to release of pharmacologically active drug fragments. Table 2 lists potent cytotoxins which are suitable for conjugation. Previous efforts to synthesize antibody conjugates or to generate pharmacologically active variants of these cytotoxins has, in some cases, provided useful insights into which functional groups are amenable to modification. The following modified cytotoxics may be used to construct aptamer-linker-drug conjugates.

Calicheamicins: N-acetyl gamma calicheamicin dimethyl hydrazide (NAc-γ-DMH) presents a reactive hydrazide group that readily reacts with aldehydes to form the corresponding hydrazone. NAc-γ-DMH can be used directly to conjugate to aldehyde bearing linkers, or, alternatively, can be converted to an N-hydroxysuccinimide-bearing amine-reactive form (NAc-γ-NHS) as described by Hamann et al. (*Bioconjugate Chem.*, 13: 47-58 (2002)) to be conjugated to amine-bearing aptamers.

Maytansinoids: Conjugatable forms of maytansinoids are accessible through re-esterification of maytansinol which itself may be produced as described in U.S. Pat. Nos. 4,360,462 and 6,333,410 through reduction of maytansine or ansamitocin P-3 using one of several reducing agents (including lithium aluminum hydride, lithium trimethoxyaluminum hydride, lithium triethoxyaluminum hydride, lithium tripropoxyaluminum hydride, and the corresponding sodium salts). Maytansinol may subsequently be converted to an amine-reactive form as described in U.S. Pat. No. 5,208,020 by (1) reaction with a disulfide-containing carboxylic acid (e.g. the variety of linkers considered in U.S. Pat. No. 5,208,020) in the presence of carbodiimide (e.g. dicylcohexylcarbodiimide) and catalytic amounts of zinc chloride (as described in U.S. Pat. No. 4,137,230), (2) reduction of the disulfide using a thiol-specific reagent (e.g. dithiothreitol) followed by HPLC purification to yield a thiol-bearing maytansinoid, and (3) reaction with a bifunctional thiol- and amine-reactive crosslinking agent (e.g. N-succinimidyl 4-(2-pyridyldithio) pentanoate). A representative activated maytansinoid bearing an amine-reactive N-hydroxysuccinimide suitable for conjugate formation is shown in Table 2 (May-NHS).

Vinca alkaloids: Vinca alkaloids such as vinblastine can be conjugated directly to aldehyde-bearing linkers following conversion to a hydrazide form as described by Brady et al. (J. Med. Chem., 45:4706-4715, 2002). Briefly, vinblastine sulfate is dissolved in 1:1 hydrazine/ethanol and heated to 60° C.-65° C. for 22 hours to yield desacetylvinblastine 3-carboxhydrazide (Table 2, DAVCH). Alternatively, amine-reactive forms of vinblastine may be generated in situ as described by Trouet et al. (U.S. Pat. No. 4,870,162) by (1) initially converting vinblastine sulfate to the desacetyl form (e.g. as described by Brady et al., reacting with 1:3 hydrazine/methanol at 20° C. for 20 hours), (2) reacting the resulting free base with approximately 2-fold excess succinic anhydride to generate the hemisuccinate (Table 2, DAVS), and (3) reacting with isobutyl chloroformate to form the reactive mixed anhydride.

Cryptophycins: Cryptophycin is a naturally occurring, highly potent tubulin inhibitor. Extensive medicinal chemistry efforts to improve potency and manufacturability yielded cryptophycin-52 (LY355703). Most sites on the cyclic depsipeptide cannot be modified without significantly reducing biological activity. Modifications to the C3'-phenyl ring are readily tolerated, however, indicating this site is a handle for the formation of functional conjugates. Synthesis of an amine-bearing derivative of Cryptophycin-52 has been previously described (Eggen and Georg, Medicinal Research Reviews, 22(2):85-101, 2002). This derivative (Table 2, Cryp-NH2) is directly suitable for conjugation.

Tubulysins: Tubulysins are a recently discovered class of highly potent tubulin inhibitors. As linear peptides of modified amino acids, they are amenable to chemical synthesis and conjugation using relatively standard peptide chemistries (e.g. in situ carboxylate activation via carbodiimides). A representative tubulysin structure is shown in Table B below.

Others: A number of other highly potent cytotoxic agents have been identified and characterized, many of which may additionally be suitable for the formation of aptamer-linker-drug conjugates. These would include modified variants of dolastatin-10, dolastatin-15, auristatin E, rhizoxin, epothilone B, epothilone D, taxoids.

TABLE B

Cytotoxins For Use in Conjugation with Aptamers

Calicheamicins

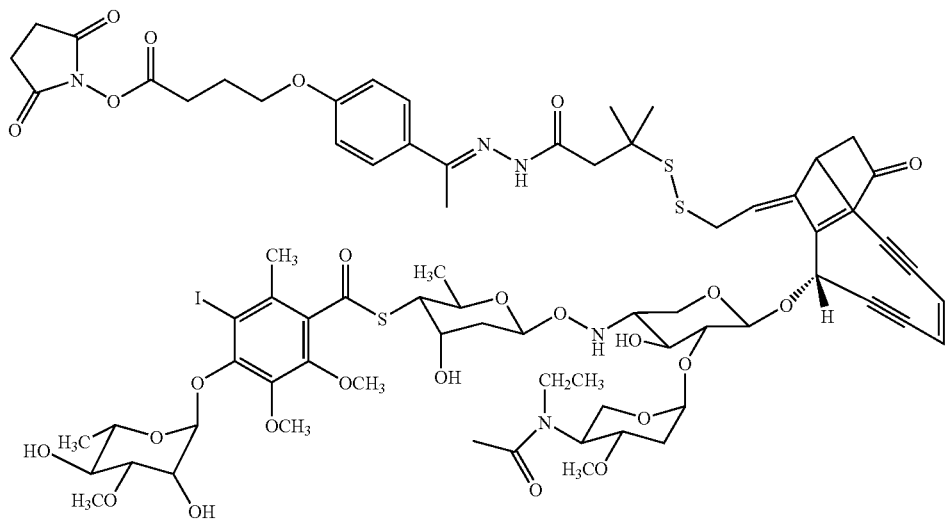

NAc-gamma calicheamicin dimethyl hydrazide
(NAc-γ-DMH)

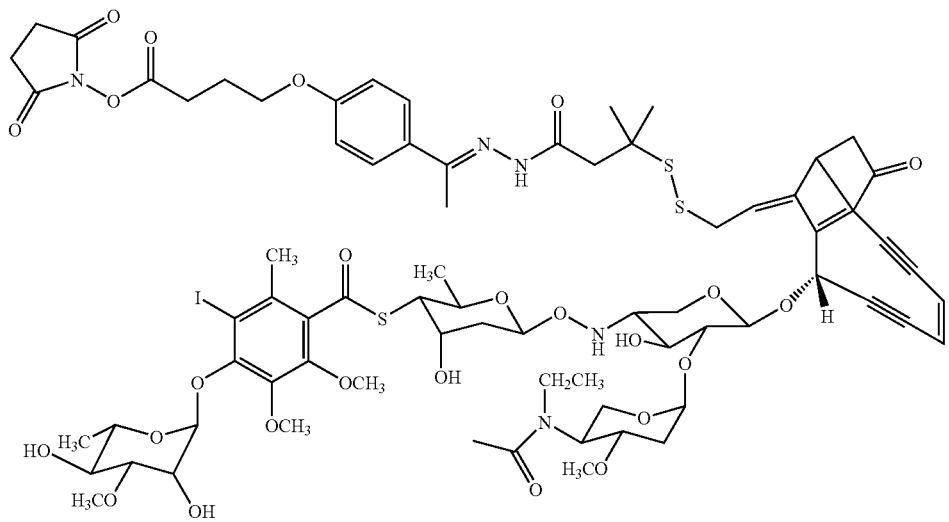

NAc-gamma calicheamicin-'AcBut'-N-hydroxysuccinimide
(NAc-γ-NHS)

TABLE B-continued
Cytotoxins For Use in Conjugation with Aptamers
Maytansinoids
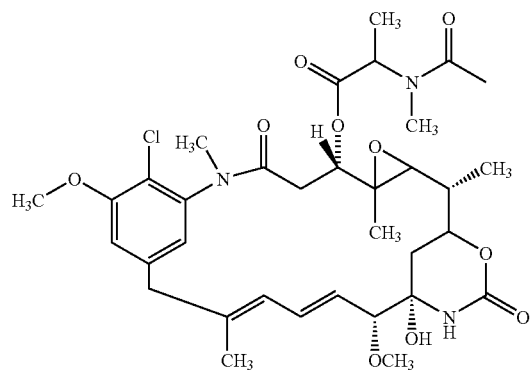
Maytansine
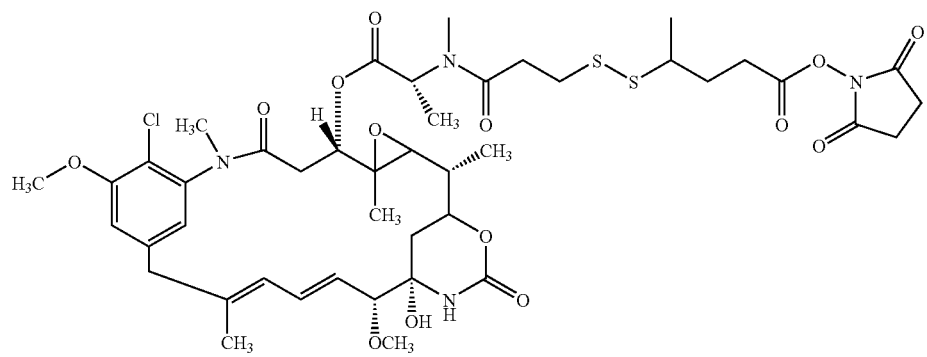
May-NHS
Vinca alkaloids
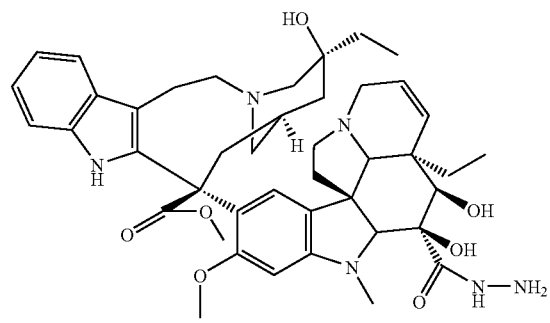
Desacetyl vinblastine 3-carboxyhydrazide (DAVCH)
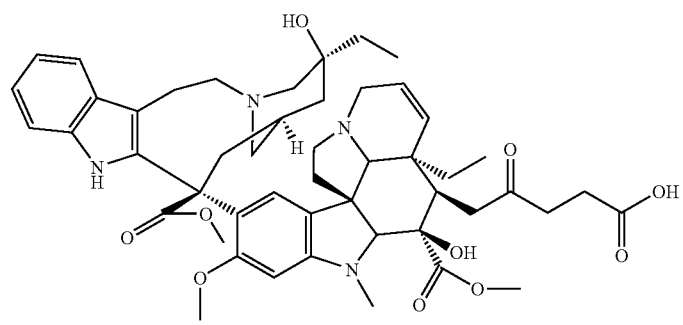
Desacetyl vinblastine 4-O-succinate (DAVS)

TABLE B-continued

Cytotoxins For Use in Conjugation with Aptamers

Cryptophycins

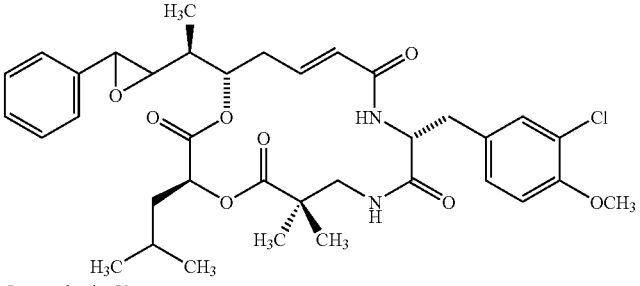

Cryptophycin-52

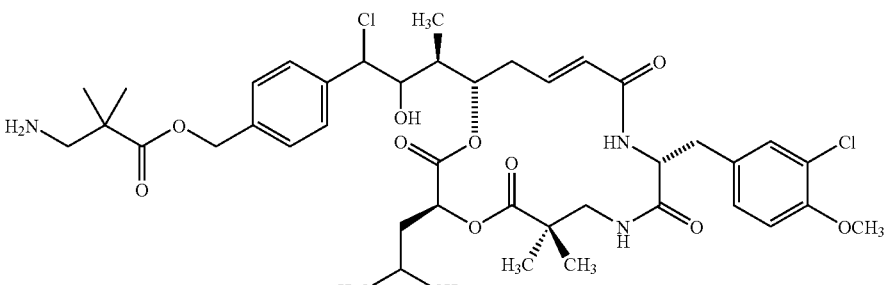

Cryptophycin-52-amine (Cryp-NH2)

Tubulysins

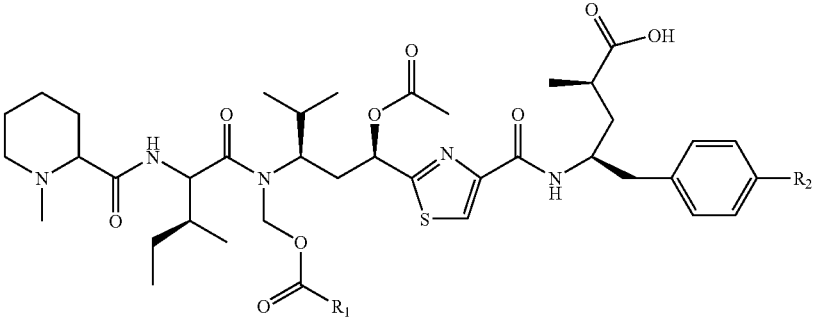

Representative tubulysin structure (TUB)

Linkers: The linker portion of the conjugate presents a plurality (i.e., 2 or more) of nucleophilic and/or electrophilic moieties that serve as the reactive attachment points for aptamers and drugs. Nucleophilic moieties include, for example, free amines, hydrazides, or thiols. Electrophilic moieties include, for example, activated carboxylates (e.g. activated esters or mixed anhydrides), activated thiols (e.g. thiopyridines), maleimides, or aldehydes.

To facilitate stepwise synthesis of the conjugate, the reactive attachment points is created or unblocked in situ. For example, a carboxylate-bearing linker is transiently activated by the addition of isobutyl chloroformate to generate a mixed anhydride and subsequently subjected to attack by amine-bearing aptamers and/or drugs. A Boc-protected amine on a heterobifunctional linker (e.g. Boc-amino-PEG-NHS) is deprotected following an initial coupling reaction that quenches its electrophilic moieties. NHS-containing linkers is converted into hydrazide-reactive aldehydes through reaction with mixed amine- and diol-bearing linkers (e.g. aminoglycosides) followed by periodate oxidation. As such, partial reaction of an NHS-containing dendrimer with an amine-bearing aptamer, followed by derivatization with aminoglycoside and oxidation generates a multivalent aldehyde for conjugation.

By using a high molecular weight linker, renal clearance of the conjugate can be minimized, even in the eventuality that aptamers connected to the conjugate are removed (e.g. as a result of nuclease degradation in vivo). Preventing renal elimination increases the in vivo half-life of the drug conjugate and also prevents toxic concentrations of drug from accumulating in the kidneys, a particular concern with high potency cytotoxin conjugates. In the preferred embodiment, the bulk of the linker is composed of one or more chains of polyethylene glycol. The overall molecular weight of the conjugate must be greater than 20,000 Da to effectively block renal clearance. While synthesis of relatively monodisperse, high molecular weight (20,000 Da) PEG chains is feasible, it is equally feasible to attach multiple medium (2,000 Da) molecular weight PEG chains to a central core entity (especially given that aptamers attached to the linker contribute substantially to the overall conjugate size). The reactive attachment points for the aptamers and drugs may be introduced either into the core used to anchor the PEG chains or introduced at the free ends of the PEG chains, i.e., well removed from the core.

Several different types of core molecules are used to anchor PEG chain attachment. Examples include simple small molecules bearing multiple nucleophiles or electrophiles (e.g. erythritol, sorbitol, lysine), linear oligomers or polymers (e.g. oligolysine, dextrans), or singly-reactive molecules with the capacity to self assemble into higher order structures (e.g. phospholipids with the capacity to form micelles or liposomes). Representative linkers are listed in the Table C below.

TABLE C

Linkers For Use in Conjugate Formation

| Linker | Structure |
|---|---|
| Boc-NH2-PEG-NHS | [structure] |
| Nucleophilic dendrimers (core = erythritol) | [structure]; X = —CH$_2$CH$_2$CH$_2$NH$_2$ or —CH$_2$CH$_2$SH |
| Electrophilic dendrimers (core = erythritol) | [structure]; X = [structure] or [structure] |
| Electrophilic dendrimers (core = octa-polyethylene glycol) | [structure]; X = [structure] or [structure] |
| Electrophilic comb polymers | [structure]; R$_1$ = H or CH$_3$; R$_2$ = CH$_3$ or other alkyl; AO = alkylene oxide |

Conjugate Synthesis: The table shown below lists examples specific combinations of aptamers, linkers, and drugs that are combined to generate therapeutic aptamer-drug conjugates. In one embodiment, the conjugate synthesis is a one-pot reaction in which aptamer, linker, and drug are combined at appropriate levels to yield the final conjugate. In other embodiments, as noted in Table D, the stepwise addition of aptamer and drug is required.

In Table D below, the term "NH2-aptamer" includes aptamers bearing single and multiple primary amines generated as described above. The term "COOH-aptamer" corresponds to an aptamer bearing a carboxylate at the 5'-terminus as described above. Abbreviations for linkers and drugs correspond to the trivial names provided in Tables B and C.

TABLE D

Methods for Generating Therapeutic Aptamer-Drug Conjugates

| Aptamer | Linker | Drug | Process |
|---|---|---|---|
| Amine | Boc-NH2-PEG-NHS | NAc-γ-NHS | Amine bearing aptamer is reacted with excess Boc-NH2-PEG-NHS at 4–20° C. at approximately neutral pH (7–8). The reaction is quenched by the addition of methylamine and the Boc group is removed by reaction with trifluoroacetic acid (TFA) to yield an aptamer-PEG-amine conjugate which is purified by SAX-HPLC. Slight excess of Drug (NAc-γ-NHS or May-NHS) is reacted with the aptamer-PEG-amine at 4–20° C. at approximately neutral pH (7–8). The aptamer-PEG-drug conjugate is isolated by HPLC. |
| Amine | Boc-NH2-PEG-NHS | May-NHS | |
| Amine | Boc-NH2-PEG-NHS | DAVS | Amine bearing aptamer is reacted with excess Boc-NH2-PEG-NHS at 4–20° C. at approximately neutral pH (7–8). The reaction is quenched by the addition of methylamine and the Boc group is removed by reaction with trifluoroacetic acid (TFA) to yield an aptamer-PEG-amine conjugate which is purified by SAX-HPLC. DAVS or TUB is activated in situ by the addition of triethylamine followed by isobutyl chloroformate to transiently generate the mixed anhydride form of the drug (reaction carried out in dioxane on ice for 1 hour). The pH of the aptamer-PEG conjugate is adjusted to 8.5 by the addition of 1 N NaOH and the conjugate cooled to 5° C. Activated DAVS or TUB is combined with the aptamer conjugate which is stirred at 5° C. for 14 hours, during which time the pH is maintained at 8.5 through addition of 1 N NaOH. |
| Amine | Boc-NH2-PEG-NHS | TUB | |
| Amine | NHS-PEG-erythritol | NAc-γ-NHS | Amine bearing aptamer is reacted with excess NHS-PEG-erythritol at 4–20° C. at approximately neutral pH (7–8). The reaction is quenched by the addition of a vast excess of diaminohexane and the aptamer-linker conjugate purified by SAX-HPLC. Slight excess of Drug (NAc-γ-NHS or May-NHS) is reacted with the aptamer-linker conjugate at 4–20° C. at approximately neutral pH (7–8). The resulting conjugate is isolated by HPLC. |
| Amine | NHS-PEG-erythritol | May-NHS | |
| Amine | NHS-PEG-erythritol | NAc-γ-DMH | Amine bearing aptamer is reacted with excess NHS-PEG-erythritol at 4–20° C. at approximately neutral pH (7–8). The reaction is quenched by the addition of excess Drug (Cryp-NH2, NAc-γ-DMH, DAVCH). The resulting conjugate is isolated by HPLC. |
| Amine | NHS-PEG-erythritol | DAVCH | |
| Amine | NHS-PEG-erythritol | Cryp-NH2 | |
| Amine | pNP-PEG-erythritol | NAc-γ-NHS | Amine bearing aptamer is reacted with excess pNP-PEG-erythritol at 4–20° C. at approximately neutral pH (7–8). The reaction is quenched by the addition of a vast excess of diaminohexane and the aptamer-linker conjugate purified by SAX-HPLC. Slight excess of Drug (NAc-γ-NHS or May-NHS) is reacted with the aptamer-linker conjugate at 4–20° C. at approximately neutral pH (7–8). The resulting conjugate is isolated by HPLC. |
| Amine | pNP-PEG-erythritol | May-NHS | |
| Amine | pNP-PEG-erythritol | NAc-γ-DMH | Amine bearing aptamer is reacted with excess pNP-PEG-erythritol at 4–20° C. at approximately neutral pH (7–8). The reaction is quenched by the addition of excess Drug (Cryp-NH2, NAc-γ-DMH, DAVCH). The resulting conjugate is isolated by HPLC. |
| Amine | pNP-PEG-erythritol | DAVCH | |
| Amine | pNP-PEG-erythritol | Cryp-NH2 | |
| Amine | NHS-PEG-erythritol | DAVS | Amine bearing aptamer is reacted with excess NHS-PEG-erythritol at 4–20° C. at approximately neutral pH (7–8). The reaction is quenched by the addition of a vast excess of diaminohexane and the aptamer-linker conjugate purified by SAX-HPLC. DAVS or TUB is activated in situ by the addition of triethylamine followed by isobutyl chloroformate to transiently generate the mixed anhydride form of the drug (reaction carried out in dioxane on ice for 1 hour). The pH of the aptamer-PEG conjugate is adjusted to 8.5 by the addition of 1 N NaOH and the conjugate cooled to 5° C. Activated DAVS or TUB is combined with the aptamer conjugate which is stirred at 5° C. for 14 hours, during which time the pH is maintained at 8.5 through addition of 1 N NaOH. |
| Amine | NHS-PEG-erythritol | TUB | |
| Amine | pNP-PEG-erythritol | DAVS | Amine bearing aptamer is reacted with excess pNP-PEG-erythritol at 4–20° C. at approximately neutral pH (7–8). The reaction is quenched by the addition of diaminohexane and the aptamer-linker conjugate purified by SAX-HPLC. DAVS or TUB is activated in situ by the addition of triethylamine followed by isobutyl chloroformate to transiently generate the mixed anhydride form of the drug (reaction carried out in dioxane on ice for 1 hour). The pH of the aptamer-PEG conjugate is adjusted to 8.5 by the addition of 1 N NaOH and the conjugate cooled to 5° C. Activated DAVS or TUB is combined with the aptamer conjugate which is stirred at 5° C. for 14 hours, during which time the pH is maintained at 8.5 through addition of 1 N NaOH. |
| Amine | pNP-PEG-erythritol | TUB | |
| Amine | pNP-PEG-octaPEG | NAc-γ-NHS | Amine bearing aptamer is reacted with excess NHS-PEG-octaPEG at 4–20° C. at approximately neutral pH (7–8). The reaction is quenched by the addition of a vast excess of diaminohexane and the aptamer-linker conjugate purified by SAX-HPLC. Slight excess of Drug (NAc-γ-NHS or May-NHS) is reacted with the aptamer-linker conjugate at 4–20° C. at approximately neutral pH (7–8). The resulting conjugate is isolated by HPLC. |
| Amine | NHS-PEG-octaPEG | May-NHS | |

TABLE D-continued

Methods for Generating Therapeutic Aptamer-Drug Conjugates

| Aptamer | Linker | Drug | Process |
|---|---|---|---|
| Amine | NHS-PEG-octaPEG | NAc-γ-DMH | Amine bearing aptamer is reacted with excess NHS-PEG-octaPEG at |
| Amine | NHS-PEG-octaPEG | DAVCH | 4–20° C. at approximately neutral pH (7–8). The reaction is quenched |
| Amine | NHS-PEG-octaPEG | Cryp-NH2 | by the addition of excess Drug (Cryp-NH2, NAc-γ-DMH, DAVCH). The resulting conjugate is isolated by HPLC. |
| Amine | pNP-PEG-octaPEG | NAc-γ-NHS | Amine bearing aptamer is reacted with excess pNP-PEG-octaPEG at |
| Amine | pNP-PEG-octaPEG | May-NHS | 4–20° C. at approximately neutral pH (7–8). The reaction is quenched by the addition of a vast excess of diaminohexane and the aptamer-linker conjugate purified by SAX-HPLC. Slight excess of Drug (NAc-γ-NHS or May-NHS) is reacted with the aptamer-linker conjugate at 4–20° C. at approximately neutral pH (7–8). The resulting conjugate is isolated by HPLC. |
| Amine | pNP-PEG-octaPEG | NAc-γ-DMH | Amine bearing aptamer is reacted with excess pNP-PEG-octaPEG at |
| Amine | pNP-PEG-octaPEG | DAVCH | 4–20° C. at approximately neutral pH (7–8). The reaction is quenched |
| Amine | pNP-PEG-octaPEG | Cryp-NH2 | by the addition of excess Drug (Cryp-NH2, NAc-γ-DMH, DAVCH). The resulting conjugate is isolated by HPLC. |
| Amine | NHS-PEG-octaPEG | DAVS | Amine bearing aptamer is reacted with excess NHS-PEG-octaPEG at |
| Amine | NHS-PEG-octaPEG | TUB | 4–20° C. at approximately neutral pH (7–8). The reaction is quenched by the addition of a vast excess of diaminohexane and the aptamer-linker conjugate purified by SAX-HPLC. DAVS or TUB is activated in situ by the addition of triethylamine followed by isobutyl chloroformate to transiently generate the mixed anhydride form of the drug (reaction carried out in dioxane on ice for 1 hour). The pH of the aptamer-PEG conjugate is adjusted to 8.5 by the addition of 1 N NaOH and the conjugate cooled to 5° C. Activated DAVS or TUB is combined with the aptamer conjugate which is stirred at 5° C. for 14 hours, during which time the pH is maintained at 8.5 through addition of 1 N NaOH. |
| Amine | pNP-PEG-octaPEG | DAVS | Amine bearing aptamer is reacted with excess pNP-PEG-octaPEG at |
| Amine | pNP-PEG-octaPEG | TUB | 4–20° C. at approximately neutral pH (7–8). The reaction is quenched by the addition of a vast excess of diaminohexane and the aptamer-linker conjugate purified by SAX-HPLC. DAVS or TUB is activated in situ by the addition of triethylamine followed by isobutyl chloroformate to transiently generate the mixed anhydride form of the drug (reaction carried out in dioxane on ice for 1 hour). The pH of the aptamer-PEG conjugate is adjusted to 8.5 by the addition of 1 N NaOH and the conjugate cooled to 5° C. Activated DAVS or TUB is combined with the aptamer conjugate which is stirred at 5° C. for 14 hours, during which time the pH is maintained at 8.5 through addition of 1 N NaOH |
| Amine | PEG-comb | NAc-γ-DMH | Amine bearing aptamer is reacted with excess PEG-comb at 4–20° C. |
| Amine | PEG-comb | Cryp-NH2 | at approximately neutral pH (7–8). Excess Drug (NAc-γ-DMH, |
| Amine | PEG-comb | DAVCH | Cryp-NH2, or DAVCH) is added to the aptamer-PEG-comb reaction at 4–20° C. at approximately neutral pH (7–8). The resulting conjugate is isolated by HPLC. |
| COOH | NH2-PEG-erythritol | NAc-γ-NHS | Carboxylate-bearing aptamer is reacted with a slight excess of NH2- |
| COOH | NH2-PEG-erythritol | May-NHS | PEG-erythritol in the presence of EDC at 4–20° C. at pH 4.5–6. The resulting aptamer-linker conjugate purified by SAX-HPLC and reacted with excess Drug (NAc-γ-NHS or May-NHS). The aptamer-linker-drug conjugate is purified by SAX-HPLC. |
| COOH | NH2-PEG-erythritol | DAVS | (1) Stepwise: Carboxylate-bearing aptamer is reacted with a |
| COOH | NH2-PEG-erythritol | TUB | slight excess of NH2-PEG-erythritol in the presence of EDC at 4–20° C. at pH 4.5–6. The resulting aptamer-linker conjugate purified by SAX-HPLC. Drug (DAVS or TUB) is activated in situ by the addition of triethylamine followed by isobutyl chloroformate to transiently generate the mixed anhydride form of the drug (reaction carried out in dioxane on ice for 1 hour). The pH of the aptamer-PEG conjugate is adjusted to 8.5 by the addition of 1 N NaOH and the conjugate cooled to 5° C. Activated DAVS or TUB is combined with the aptamer conjugate which is stirred at 5° C. for 14 hours, during which time the pH is maintained at 8.5 through addition of 1 N NaOH. The aptamer-linker-drug conjugate is purified by SAX-HPLC. One-pot: Carboxylate-bearing aptamer and Drug (DAVS or TUB) at a suitable ratio to achieve the desired loading is reacted with limiting NH2-PEG-erythritol in the presence of EDC at 4–20° C. at pH 4.5–6. The resulting aptamer-linker conjugate purified by SAX-HPLC. |
| Amine | NHS-PEG-erythritol | NAc-γ-DMH | Amine bearing aptamer is reacted with excess NHS-PEG-erythritol |
| Amine | NHS-PEG-erythritol | DAVCH | at 4–20° C. at approximately neutral pH (7–8). The reaction is quenched by the addition of a vast excess of a suitable aminoglycoside and the aptamer-linker conjugate purified by SAX-HPLC. Further reaction with an excess of sodium metaperiodate at 4–20° C. and pH 5.5–6 yields a multivalent aldehyde which can be isolated by size-exclusion chromatography. Excess Drug (NAc-γ- |

TABLE D-continued

Methods for Generating Therapeutic Aptamer-Drug Conjugates

| Aptamer | Linker | Drug | Process |
|---|---|---|---|
| | | | DMH or DAVCH) is added and reacted at 4–20° C. at pH 5.5–7. The resulting conjugate is isolated by HPLC. |
| Amine | NHS-PEG-octaPEG | NAc-γ-DMH | Amine bearing aptamer is reacted with excess NHS-PEG-octaPEG |
| Amine | NHS-PEG-octaPEG | DAVCH | at 4–20° C. at approximately neutral pH (7–8). The reaction is quenched by the addition of a vast excess of a suitable aminoglycoside and the aptamer-linker conjugate purified by SAX-HPLC. Further reaction with an excess of sodium metaperiodate at 4–20° C. and pH 5.5–6 yields a multivalent aldehyde which can be isolated by size-exclusion chromatography. Excess Drug (NAc-γ-DMH or DAVCH) is added and reacted at 4–20° C. at pH 5.5–7. The resulting conjugate is isolated by HPLC. |

PSMA Specific Aptamers

The materials of the present invention comprise a series of novel nucleic acid aptamers of 48-74 nucleotides in length which bind specifically to PSMA, and which in some embodiments, functionally modulate, e.g., block, the activity of PSMA in in vivo and/or cell-based assays, while in other embodiments, are conjugated to a cytotoxic moiety for delivery of a toxic payload, particularly a cytotoxin, to PSMA expressing cells. In some embodiments, the cytotoxin is delivered in vitro. In some embodiments, the cytotoxin is delivered in vivo.

Aptamers capable of specifically binding and modulating PSMA are set forth herein. These aptamers also provide a low-toxicity, safe, and effective modality for the delivery of cytotoxic moieties to diseases or disorders such as prostate cancer, and other solid non-prostate tumors, which are known to be associated with an upregulation of PSMA expression.

Examples of PSMA specific binding aptamers for use as aptamer-toxin conjugate therapeutics and/or diagnostics include the sequences listed below. The following nucleic acid sequences listed are in the 5' to 3' direction, and all nucleotides are 2'-OH, except where lower case letters "m" and "f" and "d", preceding A, C, G, or U, refer to 2'-O-methyl, 2'-fluoro, and 2'deoxy modified nucleotides respectively. "3T" denotes an inverted 3' deoxy thymidine, "s" denotes a phosphorothioate internucleotide linkage, and NH2 denotes an amine modification, a hexylamine terminal group, to facilitate chemical coupling.

ARC1091
mAGmAGGmAGmAGmAmAmCGmUmUmCmUmAmCmUmAm  SEQ ID NO 17
UGGGmUGGmCmUGGGmAGGGG

ARC1142
NH2-mAGmAGGmAGmAGmAmAmCGmUmUmCmUmAmCm  SEQ ID NO 18
UmAmUGGGmUGGmCmUGGGmAGGGG

ARC1786
NH2-mAGmAGGmAGmAGmAmAmCGmUmUmCmUmAmCm  SEQ ID NO 19
UmAmUGGGmUGGmCmUGGGmAGGGG-3T

ARC591
GGAGGAGAAAAAGAfCfCfUGAfCfUfUfCfUAfUAf  SEQ ID NO 22
CfUAAGfUfCfUAfCGfUfUfCfCfUfCfCA

ARC2038
NH2-GGAGGACGAAAAAAfCfCfUGAfCfUfUfCfUA  SEQ ID NO 23
fUAfCfUAAGfUfCfUAfCGfUfUfCfCfUUfCfCA

ARC2039
NH2-GGAGGACGAAAAAGAfCfCfUGAfCfUfUfCfU  SEQ ID NO 24
AfUAfCfUAAGfUfCfUAfCGfUfUfCfCfUfCfC-3T

ARC 1113
NH2-mCmGmGmAfCfCmGAAfCAmAmGmGmCfCfUGA  SEQ ID NO 88
fCfUfUfCfUAfUAfCfUAAmGmCmCmUAfCmGfUmU
mCmCmGU

ARC2035
NH2-mCmGmGmACmGAAfCAmAmGmGmCfCfUGAfCf  SEQ ID NO 89
UfUfCfUAfUAfCfUAAmGmCmCmUAfCmGfUmUmCm
CmGU

ARC2036
mCmGmGmAfCfCmGAAfCAmAmGmGmCfCfUGAfCfU  SEQ ID NO 90
fUfCfUAfUAfCfUAAmGmCmCmUAfCmGfUmUmCmC
mG-3T

ARC942
mCmGmGmACmGAAAAmGmAmCfCfUGAfCfUfUfC  SEQ ID NO 128
fUAfUAfCfUAAmGmUmCmUAfCmGfUmUmCmCmG-
3T

ARC2037
NH2-mCmGmGmAfCfCmGAAAAmAmGmAmCfCfUGAf  SEQ ID NO 129
CfUfUfCfUAfUAfCfUAAmGmUmCmUAfCmGfUmUm
CmCmG-3T

ARC1026
mCmGmGmAfCfCmGAAAAmAmGmAmCfCfUGAfCfUf  SEQ ID NO 130
UfCfUAfUAfCfUAAmGmUmCmUAfCmGfUmUmCmCm

ARC1721
mCmGmGmAfCfCmGAAfCAmAmGmGmCfCfUGAfCfU  SEQ ID NO 156
fUfCfUmAfUAfCfUAmGmCmCmUAfCmGfUmUm
CmCmG-3T

ARC2033
NH2-mCmGmGmAfCfCmGAAfCAmAmGmGmCfCfUGA  SEQ ID NO 157
fCfUfUfCfUmAfUAfCfUAAmGmCmCmUAfCmGf
UmUmCmCmG

ARC2034
NH2-mCmGmGmAfCfCmGAAfCAmAmGmGmCfCfUGA  SEQ ID NO 158
fCfUfUfCfUmAfUAfCfUAAmGmCmCmUAfCmGf
UmUmCmCmG-3T

ARC1725
mCmGmGmAfCfCmGdAdAfCmAmAmGmGmCfCfU-s-  SEQ ID NO 162
dGmAfCfUfUfCfUmAfUAfCfUdAmAmGmCmCmUm
AfCmGfUmUmCmCmG-3T

ARC2032
NH2-mCmGmGmAfCfCmGdAdAfCmAmAmGmGmCfCf  SEQ ID NO 163
U-s-dGmAfCfUfUfCfUmAfUmAfCfUdAmAmGmCm
UmAfCmGfUmUmCmCmGU

Other aptamers that bind PSMA are described below in Examples 1-4. While other PSMA binding aptamers are described in U.S. patent application Ser. No. 09/978,969 filed Oct. 16, 2001, U.S. Provisional Patent Application No. 60/660,514 filed Mar. 7, 2005, and U.S. Provisional Patent Application No. 60/670,518 filed Apr. 11, 2005; each of which is incorporated by reference herein.

These aptamers may include modifications as described herein including, e.g., conjugation to lipophilic or high molecular weight compounds (e.g., PEG, incorporation of a CpG motif, incorporation of a capping moiety, incorporation of modified nucleotides, and incorporation of phosphorothioate linkages in the phosphate backbone.

In one embodiment of the invention an isolated, non-naturally occurring aptamer that binds to PSMA is provided. In some embodiments, the isolated, non-naturally occurring aptamer has a $K_D$ for PSMA of less than 100 nM, less than 50 nM, less than 10 nM, or less than 500 pM. In another embodiment, the aptamer of the invention modulates a function of PSMA. In another embodiment, the aptamer of the invention inhibits a function of PSMA while in another embodiment the aptamer stimulates a function of the target. In another embodiment of the invention, the aptamer binds to and/or modulates a function of a PSMA variant. A PSMA variant as used herein encompasses variants that perform essentially the same function as a PSMA function, preferably comprises substantially the same structure and in some embodiments comprises at least 70% sequence identity, preferably at least 80% sequence identity, more preferably at least 90% sequence identity, and more preferably at least 95% sequence identity to the amino acid sequence of the ECD of PSMA. In some embodiments of the invention, the sequence identity of target variants is determined using BLAST as described below.

The terms "sequence identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity is the algorithm used in the basic local alignment search tool (hereinafter "BLAST"), see, e.g. Altschul et al., J. Mol. Biol. 215: 403-410 (1990) and Altschul et al., Nucleic Acids Res., 15: 3389-3402 (1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al., Nucleic Acids Res., 32: W20-W25 (2004).

In another embodiment of the invention, the aptamer has substantially the same ability to bind PSMA as that of an aptamer comprising any one of SEQ ID NOS 11-13, 15-26, 30-90, 122-165, 167. In another embodiment of the invention, the aptamer has substantially the same structure and ability to bind PSMA as that of an aptamer comprising any one of SEQ ID NOS 11-13, 15-26, 30-90, 122-165, 167. In another embodiment, the aptamers of the invention have a sequence according to any one of 11-13, 15-26, 30-90, 122-165, 167. In another embodiment, the aptamers of the invention are used as an active ingredient in pharmaceutical compositions. In another embodiment, the aptamers or compositions comprising the aptamers of the invention are used to treat prostate cancer, and non-prostate solid tumors.

In one embodiment, the aptamer of the present invention is conjugated to a cytotoxic moiety for the treatment of prostate cancer and non-solid prostate tumors which are associated with PSMA expression. In some embodiments, the cytotoxic moiety is conjugated to the 3'-end of the aptamer, while in other embodiments, the cytotoxic moiety is conjugated to the 5'-end. In some embodiments, the cytotoxic moiety is encapsulated in nanoparticle forms such as liposomes, dendrimers, or comb polymers. In one embodiment, the cytotoxic moiety to which the aptamer is conjugated is a small molecule selected from the consisting of vinblastine hydrazide, calicheamicin, vinca alkaloid, a cryptophycin, a tubulysin, dolastatin-10, dolastatin-15, auristatin E, rhizoxin, epothilone B, epithilone D, taxoids, maytansinoids and any variants and derivatives thereof. In another embodiment, the cytotoxic moiety to which the aptamer is conjugated is a radioisotope selected from the group consisting of yttrium-90, indium-11, iodine-131, lutetium-177, copper-67, rhenium-186, rhenium-188, bismuth-212, bismuth-213, astatine-211, and actinium-225. In yet another embodiment, the cytotoxic moiety to which the aptamer is conjugated is a protein toxin selected from the group consisting of diphtheria toxin, ricin, abrin, gelonin, and Pseudomonas exotoxin A.

In some embodiments the aptamer therapeutics of the present invention have great affinity and specificity to their targets while reducing the deleterious side effects from non-naturally occurring nucleotide substitutions if the aptamer therapeutics break down in the body of patients or subjects. In some embodiments, the therapeutic compositions containing the aptamer therapeutics of the present invention are free of or have a reduced amount of fluorinated nucleotides.

The aptamers of the present invention can be synthesized using any oligonucleotide synthesis techniques known in the art including solid phase oligonucleotide synthesis techniques well known in the art (see, e.g., Froehler et al., Nucl. Acid Res. 14:5399-5467 (1986) and Froehler et al., Tet. Lett. 27:5575-5578 (1986)) and solution phase methods such as triester synthesis methods (see, e.g., Sood et al., Nucl. Acid Res. 4:2557 (1977) and Hirose et al., Tet. Lett., 28:2449 (1978)).

Aptamers Having Immunostimulatory Motifs

The present invention provides aptamers that bind to specifically to PSMA, and useful for delivering targeted payloads e.g., a cytotoxic moiety, to cells which express PSMA, e.g., prostate cancer cells. The targeted payload function of PSMA specific aptamers can be further enhanced by selecting for aptamers which bind to PSMA and contain immunostimulatory motifs, or by treating with aptamers which bind to PSMA in conjunction with aptamers to a target known to bind immunostimulatory sequences.

Recognition of bacterial DNA by the vertebrate immune system is based on the recognition of unmethylated CG dinucleotides in particular sequence contexts ("CpG motifs"). One receptor that recognizes such a motif is Toll-like receptor 9 ("TLR 9"), a member of a family of Toll-like receptors (~10 members) that participate in the innate immune response by recognizing distinct microbial components. TLR 9 binds unmethylated oligodeoxynucleotide ("ODN") CpG sequences in a sequence-specific manner. The recognition of CpG motifs triggers defense mechanisms leading to innate and ultimately acquired immune responses. For example, activation of TLR 9 in mice induces activation of antigen presenting cells, up regulation of MHC class I and II molecules and expression of important co-stimulatory molecules and cytokines including IL-12 and IL-23. This activation both directly and indirectly enhances B and T cell responses, including robust up regulation of the TH1 cytokine IFN-gamma. Collectively, the response to CpG sequences leads to: protection against infectious diseases, improved immune response to vaccines, an effective response against asthma, and improved antibody-dependent cell-mediated cytotoxicity. Thus, CpG ODNs can provide protection against infectious diseases, function as immuno-adjuvants or cancer therapeutics (monotherapy or in combination with a mAb or other therapies), and can decrease asthma and allergic response.

Aptamers of the present invention comprising one or more CpG or other immunostimulatory sequences can be identified or generated by a variety of strategies using, e.g., the SELEX™ process described herein. The incorporated immunostimulatory sequences can be DNA, RNA and/or a combination DNA/RNA. In general the strategies can be divided into two groups. In group one, the strategies are directed to identifying or generating aptamers comprising both a CpG motif or other immunostimulatory sequence as well as a binding site for a target, where the target (hereinafter "non-CpG target") is a target other than one known to recognize CpG motifs or other immunostimulatory sequences and known to stimulates an immune response upon binding to a CpG motif. In some embodiments of the invention the non-CpG target is PSMA. The first strategy of this group comprises performing SELEX™ to obtain an aptamer to a specific non-CpG target, preferably a target, e.g., PSMA, where a repressed immune response is relevant to disease development, using an oligonucleotide pool wherein a CpG motif has been incorporated into each member of the pool as, or as part of, a fixed region, e.g., in some embodiments the randomized region of the pool members comprises a fixed region having a CpG motif incorporated therein, and identifying an aptamer comprising a CpG motif. The second strategy of this group comprises performing SELEX™ to obtain an aptamer to a specific non-CpG target preferably a target, e.g., PSMA, where a repressed immune response is relevant to disease development, and following selection appending a CpG motif to the 5' and/or 3' end or engineering a CpG motif into a region, preferably a non-essential region, of the aptamer. The third strategy of this group comprises performing SELEX™ to obtain an aptamer to a specific non-CpG target, preferably a target, e.g., PSMA, where a repressed immune response is relevant to disease development, wherein during synthesis of the pool the molar ratio of the various nucleotides is biased in one or more nucleotide addition steps so that the randomized region of each member of the pool is enriched in CpG motifs, and identifying an aptamer comprising a CpG motif. The fourth strategy of this group comprises performing SELEX™ to obtain an aptamer to a specific non-CpG target, preferably a target, e.g., PSMA, where a repressed immune response is relevant to disease development, and identifying an aptamer comprising a CpG motif. The fifth strategy of this group comprises performing SELEX™ to obtain an aptamer to a specific non-CpG target, preferably a target, e.g., PSMA, where a repressed immune response is relevant to disease development, and identifying an aptamer which, upon binding, stimulates an immune response but which does not comprise a CpG motif.

In group two, the strategies are directed to identifying or generating aptamers comprising a CpG motif and/or other sequences that are bound by the receptors for the CpG motifs (e.g., TLR9 or the other toll-like receptors) and upon binding stimulate an immune response. The first strategy of this group comprises performing SELEX™ to obtain an aptamer to a target known to bind to CpG motifs or other immunostimulatory sequences and upon binding stimulate an immune response using an oligonucleotide pool wherein a CpG motif has been incorporated into each member of the pool as, or as part of, a fixed region, e.g., in some embodiments the randomized region of the pool members comprise a fixed region having a CpG motif incorporated therein, and identifying an aptamer comprising a CpG motif. The second strategy of this group comprises performing SELEX™ to obtain an aptamer to a target known to bind to CpG motifs or other immunostimulatory sequences and upon binding stimulate an immune response and then appending a CpG motif to the 5' and/or 3' end or engineering a CpG motif into a region, preferably a non-essential region, of the aptamer. The third strategy of this group comprises performing SELEX™ to obtain an aptamer to a target known to bind to CpG motifs or other immunostimulatory sequences and upon binding stimulate an immune response wherein during synthesis of the pool, the molar ratio of the various nucleotides is biased in one or more nucleotide addition steps so that the randomized region of each member of the pool is enriched in CpG motifs, and identifying an aptamer comprising a CpG motif. The fourth strategy of this group comprises performing SELEX™ to obtain an aptamer to a target known to bind to CpG motifs or other immunostimulatory sequences and upon binding stimulate an immune response and identifying an aptamer comprising a CpG motif. The fifth strategy of this group comprises performing SELEX™ to obtain an aptamer to a target known to bind to CpG motifs or other immunostimulatory sequences, and identifying an aptamer which upon binding, stimulate an immune response but which does not comprise a CpG motif.

A variety of different classes of CpG motifs have been identified, each resulting upon recognition in a different cascade of events, release of cytokines and other molecules, and activation of certain cell types. See, e.g., CpG Motifs in Bacterial DNA and Their Immune Effects, Annu. Rev. Immunol. 2002, 20:709-760, incorporated herein by reference. Additional immunostimulatory motifs are disclosed in the following U.S. patents, each of which is incorporated herein by reference: U.S. Pat. No. 6,207,646; U.S. Pat. No. 6,239,116; U.S. Pat. No. 6,429,199; U.S. Pat. No. 6,214,806; U.S. Pat. No. 6,653,292; U.S. Pat. No. 6,426,434; U.S. Pat. No. 6,514,948 and U.S. Pat. No. 6,498,148. Any of these CpG or other immunostimulatory motifs can be incorporated into an aptamer. The choice of aptamers is dependent on the disease or disorder to be treated. Preferred immunostimulatory motifs are as follows (shown 5' to 3' left to right) wherein "r"

designates a purine, "y" designates a pyrimidine, and "X" designates any nucleotide: AACGTTCGAG (SEQ ID NO 4; AACGTT; ACGT, rCGy; rrCGyy, XCGX, XXCGXX, and $X_1X_2CGY_1Y_2$ wherein $X_1$ is G or A, $X_2$ is not C, $Y_1$ is not G and $Y_2$ is preferably T.

In those instances where a CpG motif is incorporated into an aptamer that binds to a specific target other than a target known to bind to CpG motifs and upon binding stimulate an immune response (a "non-CpG target"), the CpG is preferably located in a non-essential region of the aptamer. Non-essential regions of aptamers can be identified by site-directed mutagenesis, deletion analyses and/or substitution analyses. However, any location that does not significantly interfere with the ability of the aptamer to bind to the non-CpG target may be used. In addition to being embedded within the aptamer sequence, the CpG motif may be appended to either or both of the 5' and 3' ends or otherwise attached to the aptamer. Any location or means of attachment may be used so long as the ability of the aptamer to bind to the non-CpG target is not significantly interfered with.

As used herein, "stimulation of an immune response" can mean either (1) the induction of a specific response (e.g., induction of a Th1 response) or of the production of certain molecules or (2) the inhibition or suppression of a specific response (e.g., inhibition or suppression of the Th2 response) or of certain molecules.

Pharmaceutical Compositions

The invention also includes pharmaceutical compositions containing aptamer molecules that bind to PSMA and/or aptamer molecules that bind to PSMA conjugated to a cytotoxic moiety. In some embodiments, the compositions are suitable for internal use and include an effective amount of a pharmacologically active compound of the invention, alone or in combination, with one or more pharmaceutically acceptable carriers. The compounds are especially useful in that they have very low, if any toxicity.

Compositions of the invention can be used to treat or prevent a pathology, such as a disease or disorder, or alleviate the symptoms of such disease or disorder in a patient. For example, compositions of the present invention can be used to treat or prevent a pathology associated with prostate cancer, and other types of cancer which express PSMA in the neovasculature of solid tumors.

Compositions of the invention are useful for administration to a subject suffering from, or predisposed to, a disease or disorder which is related to or derived from a target to which the aptamers of the invention specifically bind. Compositions of the invention can be used in a method for treating a patient or subject having a pathology. The method involves administering to the patient or subject a composition comprising aptamers, and/or aptamer-toxin conjugates that bind to a specific cell surface component (e.g., an integral membrane protein) associated with the pathology, so that upon binding of the aptamer or aptamer-toxin conjugate to the cell surface component (and delivery of a toxic payload to the cells on which the component is expressed occurs), treatment of the pathology is achieved. In some embodiments, binding of the aptamer or aptamer-toxin conjugate results in the stabilization or reduction in size of a PSMA expressing tumor in vivo.

The patient or subject having a pathology, i.e., the patient or subject treated by the methods of this invention, can be a vertebrate, more particularly a mammal, or more particularly a human.

In practice, the aptamers and/or the aptamer-toxin conjugates or their pharmaceutically acceptable salts, are administered in amounts which will be sufficient to exert their desired biological activity, e.g., the binding of the aptamer to PSMA and delivery of a toxic payload to a specific cell type.

One aspect of the invention comprises an aptamer composition of the invention in combination with other treatments for cancer related disorders. The aptamer composition of the invention may contain, for example, more than one aptamer. In some examples, an aptamer composition of the invention, containing one or more compounds of the invention, is administered in combination with another useful composition such as a cytotoxic, cytostatic, or chemotherapeutic agent such as an alkylating agent, anti-metabolite, mitotic inhibitor or cytotoxic antibiotic. In general, the currently available dosage forms of the known therapeutic agents for use in such combinations will be suitable.

"Combination therapy" (or "co-therapy") includes the administration of an aptamer composition of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Therapeutic or pharmacological compositions of the present invention will generally comprise an effective amount of the active component(s) of the therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals.

For instance, for oral administration in the form of a tablet or capsule (e.g., a gelatin capsule), the active drug component can be combined with an oral, non-toxic, pharmaceutically acceptable inert carrier such as ethanol, glycerol, water and the like. Moreover, when desired or necessary, suitable binders, lubricants, disintegrating agents, and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes, and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol, and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The compounds of the invention can also be administered in such oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

The compounds of the present invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795, incorporated herein by reference.

Furthermore, preferred compounds for the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would typically range from 0.01% to 15%, w/w or w/v.

For solid compositions, excipients include pharmaceutical grades of mannitol, lactose, starch, magnesium stearate, sodium saccharin, talcum, cellulose, glucose, sucrose, magnesium carbonate, and the like. The active compound defined above, may be also formulated as suppositories, using for example, polyalkylene glycols, for example, propylene glycol, as the carrier. In some embodiments, suppositories are advantageously prepared from fatty emulsions or suspensions.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564. For example, the aptamer molecules described herein can be provided as a complex with a lipophilic compound or non-immunogenic, high molecular weight compound constructed using methods known in the art. Additionally, liposomes may bear aptamers on their surface for targeting and carrying cytotoxic agents internally to mediate cell killing. An example of nucleic-acid associated complexes is provided in U.S. Pat. No. 6,011,020.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as for example, sodium acetate, and triethanolamine oleate.

The dosage regimen utilizing the aptamers is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.05 to 7500 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Infused dosages, intranasal dosages and transdermal dosages will range between 0.05 to 7500 mg/day. Subcutaneous, intravenous and intraperitoneal dosages will range between 0.05 to 3800 mg/day.

Effective plasma levels of the compounds of the present invention range from 0.002 mg/mL to 50 mg/mL. Indications of mass with regards to amount of aptamer in the indicated dosages and/or effective plasma concentrations refer to oligo weight only and do not include the weight of a conjugate such as a toxin or PEG moiety.

Compounds of the present invention may be administered in a single daily dose, or the total daily dosage may be administered in divided doses of two, three or four times daily.

Modulation of Pharmacokinetics and Biodistribution of Aptamer Therapeutics

It is important that the pharmacokinetic properties for all oligonucleotide-based therapeutics, including aptamers, be tailored to match the desired pharmaceutical application. While aptamers directed against extracellular targets do not suffer from difficulties associated with intracellular delivery (as is the case with antisense and RNAi-based therapeutics), such aptamers must still be able to be distributed to target organs and tissues, and remain in the body (unmodified) for a period of time consistent with the desired dosing regimen.

Thus, the present invention provides materials and methods to affect the pharmacokinetics of aptamer compositions, and, in particular, the ability to tune aptamer pharmacokinetics. The tunability of (i.e., the ability to modulate) aptamer pharmacokinetics is achieved through conjugation of modifying moieties (e.g., PEG polymers) to the aptamer and/or the incorporation of modified nucleotides (e.g., 2'-fluoro or 2'-O-methyl) to alter the chemical composition of the nucleic acid. The ability to tune aptamer pharmacokinetics is used in the improvement of existing therapeutic applications, or alternatively, in the development of new therapeutic applications. For example, in some therapeutic applications, e.g., in antineoplastic or acute care settings where rapid drug clearance or turn-off may be desired, it is desirable to decrease the residence times of aptamers in the circulation. Alternatively, in other therapeutic applications, e.g., maintenance therapies where systemic circulation of a therapeutic is desired, it may be desirable to increase the residence times of aptamers in circulation.

In addition, the tunability of aptamer pharmacokinetics is used to modify the biodistribution of an aptamer therapeutic in a subject. For example, in some therapeutic applications, it may be desirable to alter the biodistribution of an aptamer therapeutic in an effort to target a particular type of tissue or a specific organ (or set of organs). In these applications, the aptamer therapeutic preferentially accumulates in a specific tissue or organ(s). In other therapeutic applications, it may be desirable to target tissues displaying a cellular marker or a symptom associated with a given disease, cellular injury or other abnormal pathology, such that the aptamer therapeutic preferentially accumulates in the affected tissue. For example, as described in provisional application U.S. Ser. No. 60/550,790, filed on Mar. 5, 2004, and entitled "Controlled Modulation of the Pharmacokinetics and Biodistribution of Aptamer Therapeutics", and in the non-provisional application U.S. Ser. No. 11/075,648, filed on Mar. 7, 2005, and entitled "Controlled Modulation of the Pharmacokinetics and Biodistribution of Aptamer Therapeutics", PEGylation of an aptamer therapeutic (e.g., PEGylation with a 20 kDa PEG polymer) is used to target inflamed tissues, such that the PEGylated aptamer therapeutic preferentially accumulates in inflamed tissue.

To determine the pharmacokinetic and biodistribution profiles of aptamer therapeutics (e.g., aptamer conjugates or aptamers having altered chemistries, such as modified nucleotides) a variety of parameters are monitored. Such parameters include, for example, the half-life ($t_{1/2}$), the plasma clearance (Cl), the volume of distribution (Vss), the area under the concentration-time curve (AUC), maximum observed serum or plasma concentration ($C_{max}$), and the mean residence time (MRT) of an aptamer composition. As used herein, the term "AUC" refers to the area under the plot of the plasma concentration of an aptamer therapeutic versus the time after aptamer administration. The AUC value is used to estimate the bioavailability (i.e., the percentage of administered aptamer therapeutic in the circulation after aptamer administration) and/or total clearance (Cl) (i.e., the rate at which the aptamer therapeutic is removed from circulation) of a given aptamer therapeutic. The volume of distribution relates the plasma concentration of an aptamer therapeutic to the amount of aptamer present in the body. The larger the Vss, the more an aptamer is found outside of the plasma (i.e., the more extravasation).

The present invention provides materials and methods to modulate, in a controlled manner, the pharmacokinetics and biodistribution of stabilized aptamer compositions in vivo by conjugating an aptamer to a modulating moiety such as a small molecule, peptide, or polymer terminal group, or by incorporating modified nucleotides into an aptamer. As described herein, conjugation of a modifying moiety and/or altering nucleotide(s) chemical composition alters fundamental aspects of aptamer residence time in circulation and distribution to tissues.

In addition to clearance by nucleases, oligonucleotide therapeutics are subject to elimination via renal filtration. As such, a nuclease-resistant oligonucleotide administered intravenously typically exhibits an in vivo half-life of <10 min, unless filtration can be blocked. This can be accomplished by either facilitating rapid distribution out of the blood stream into tissues or by increasing the apparent molecular weight of the oligonucleotide above the effective size cut-off for the glomerulus. Conjugation of small therapeutics to a PEG polymer (PEGylation), described below, can dramatically lengthen residence times of aptamers in circulation, thereby decreasing dosing frequency and enhancing effectiveness against vascular targets.

Aptamers can be conjugated to a variety of modifying moieties, such as high molecular weight polymers, e.g., PEG; peptides, e.g., Tat (a 13-amino acid fragment of the HIV Tat protein (Vives, et al. (1997), J. Biol. Chem. 272(25): 16010-7)), Ant (a 16-amino acid sequence derived from the third helix of the *Drosophila antennapedia* homeotic protein (Pietersz, et al. (2001), Vaccine 19(11-12): 1397-405)) and $Arg_7$ (a short, positively charged cell-permeating peptides composed of polyarginine ($Arg_7$) (Rothbard, et al. (2000), Nat. Med. 6(11): 1253-7; Rothbard, J et al. (2002), J. Med. Chem. 45(17): 3612-8)); and small molecules, e.g., lipophilic compounds such as cholesterol. Among the various conjugates described herein, in vivo properties of aptamers are altered most profoundly by complexation with PEG groups. For example, complexation of a mixed 2° F. and 2'-OMe modified aptamer therapeutic with a 20 kDa PEG polymer hinders renal filtration and promotes aptamer distribution to both healthy and inflamed tissues. Furthermore, the 20 kDa PEG polymer-aptamer conjugate proves nearly as effective as a 40 kDa PEG polymer in preventing renal filtration of aptamers. While one effect of PEGylation is on aptamer clearance, the prolonged systemic exposure afforded by presence of the 20 kDa moiety also facilitates distribution of aptamer to tissues, particularly those of highly perfused organs and those at the site of inflammation. The aptamer-20 kDa PEG polymer conjugate directs aptamer distribution to the site of inflammation, such that the PEGylated aptamer preferentially accumulates in inflamed tissue. In some instances, the 20 kDa PEGylated aptamer conjugate is able to access the interior of cells, such as, for example, kidney cells.

Modified nucleotides can also be used to modulate the plasma clearance of aptamers. For example, an unconjugated aptamer which incorporates both 2'-F and 2'-OMe stabilizing chemistries, which is typical of current generation aptamers as it exhibits a high degree of nuclease stability in vitro and in vivo, displays rapid loss from plasma (i.e., rapid plasma clearance) and a rapid distribution into tissues, primarily into the kidney, when compared to unmodified aptamer.

PEG-Derivatized Nucleic Acids

As described above, derivatization of nucleic acids with high molecular weight non-immunogenic polymers has the potential to alter the pharmacokinetic and pharmacodynamic properties of nucleic acids making them more effective therapeutic agents. Favorable changes in activity can include increased resistance to degradation by nucleases, decreased filtration through the kidneys, decreased exposure to the immune system, and altered distribution of the therapeutic through the body.

The aptamer compositions of the invention may be derivatized with polyalkylene glycol ("PAG") moieties. Examples of PAG-derivatized nucleic acids are found in U.S. patent application Ser. No. 10/718,833, filed on Nov. 21, 2003, which is herein incorporated by reference in its entirety. Typical polymers used in the invention include polyethylene glycol ("PEG"), also known as polyethylene oxide ("PEO") and polypropylene glycol (including poly isopropylene glycol). Additionally, random or block copolymers of different alkylene oxides (e.g., ethylene oxide and propylene oxide) can be used in many applications. In its most common form, a polyalkylene glycol, such as PEG, is a linear polymer terminated at each end with hydroxyl groups: $HO-CH_2CH_2O-(CH_2CH_2O)_n-CH_2CH_2-OH$. This polymer, alpha-, omega-dihydroxylpolyethylene glycol, can also be represented as HO-PEG-OH, where it is understood that the -PEG- symbol represents the following structural unit: $-CH_2CH_2O-(CH_2CH_2O)_n-CH_2CH_2-$ where n typically ranges from about 4 to about 10,000.

As shown, the PEG molecule is di-functional and is sometimes referred to as "PEG diol." The terminal portions of the PEG molecule are relatively non-reactive hydroxyl moieties, the —OH groups, that can be activated, or converted to functional moieties, for attachment of the PEG to other compounds at reactive sites on the compound. Such activated PEG diols are referred to herein as bi-activated PEGs. For example, the terminal moieties of PEG diol have been functionalized as active carbonate ester for selective reaction with amino moieties by substitution of the relatively nonreactive hydroxyl moieties, —OH, with succinimidyl active ester moieties from N-hydroxy succinimide.

In many applications, it is desirable to cap the PEG molecule on one end with an essentially non-reactive moiety so that the PEG molecule is mono-functional (or mono-activated). In the case of protein therapeutics which generally display multiple reaction sites for activated PEGs, bi-functional activated PEGs lead to extensive cross-linking, yielding poorly functional aggregates. To generate mono-activated PEGs, one hydroxyl moiety on the terminus of the PEG diol molecule typically is substituted with non-reactive methoxy end moiety, $-OCH_3$. The other, un-capped terminus of the PEG molecule typically is converted to a reactive end moiety that can be activated for attachment at a reactive site on a surface or a molecule such as a protein.

PAGs are polymers which typically have the properties of solubility in water and in many organic solvents, lack of toxicity, and lack of immunogenicity. One use of PAGs is to covalently attach the polymer to insoluble molecules to make the resulting PAG-molecule "conjugate" soluble. For example, it has been shown that the water-insoluble drug paclitaxel, when coupled to PEG, becomes water-soluble. Greenwald, et al., *J. Org. Chem.*, 60:331-336 (1995). PAG conjugates are often used not only to enhance solubility and stability but also to prolong the blood circulation half-life of molecules.

Figure 2:
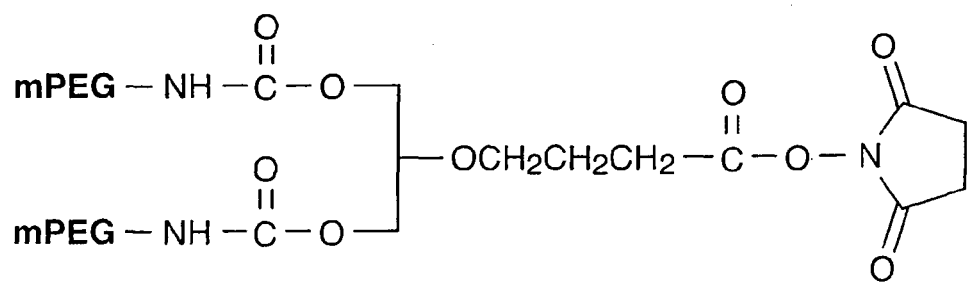
FIG. 2 is an illustration of a 40 kDa branched PEG.
Figure 3:
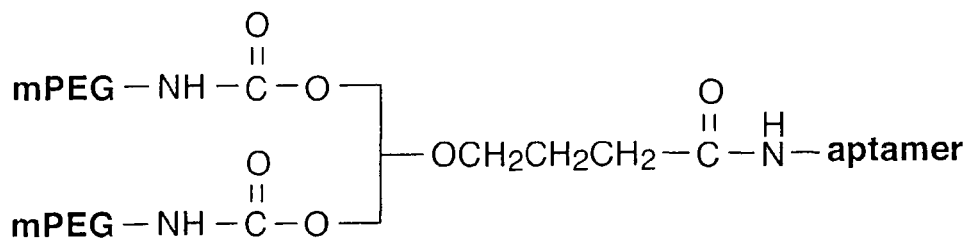
FIG. 3 is an illustration of a 40 kDa branched PEG attached to the 5'end of an aptamer.

Polyalkylated compounds of the invention are typically between 5 and 80 kDa in size however any size can be used, the choice dependent on the aptamer and application. Other PAG compounds of the invention are between 10 and 80 kDa in size. Still other PAG compounds of the invention are between 10 and 60 kDa in size. For example, a PAG polymer may be at least 10, 20, 30, 40, 50, 60, or 80 kDa in size. Such polymers can be linear or branched. In some embodiments the polymers are PEG. In some embodiments, the polymers are branched PEG. In still other embodiments, the polymers are 40 kDa branched PEG as depicted in FIG. 2. In some embodiments the 40 kDa branched PEG is attached to the 5' end of the aptamer as depicted in FIG. 3.

In contrast to biologically-expressed protein therapeutics, nucleic acid therapeutics are typically chemically synthesized from activated monomer nucleotides. PEG-nucleic acid conjugates may be prepared by incorporating the PEG using the same iterative monomer synthesis. For example, PEGs activated by conversion to a phosphoramidite form can be incorporated into solid-phase oligonucleotide synthesis. Alternatively, oligonucleotide synthesis can be completed with site-specific incorporation of a reactive PEG attachment site. Most commonly this has been accomplished by addition of a free primary amine at the 5'-terminus (incorporated using a modifier phosphoramidite in the last coupling step of solid phase synthesis). Using this approach, a reactive PEG (e.g., one which is activated so that it will react and form a bond with an amine) is combined with the purified oligonucleotide and the coupling reaction is carried out in solution.

The ability of PEG conjugation to alter the biodistribution of a therapeutic is related to a number of factors including the apparent size (e.g., as measured in terms of hydrodynamic radius) of the conjugate. Larger conjugates (>10 kDa) are known to more effectively block filtration via the kidney and to consequently increase the serum half-life of small macromolecules (e.g., peptides, antisense oligonucleotides). The ability of PEG conjugates to block filtration has been shown to increase with PEG size up to approximately 50 kDa (further increases have minimal beneficial effect as half life becomes defined by macrophage-mediated metabolism rather than elimination via the kidneys).

Production of high molecular weight PEGs (>10 kDa) can be difficult, inefficient, and expensive. As a route towards the synthesis of high molecular weight PEG-nucleic acid conjugates, previous work has been focused towards the generation of higher molecular weight activated PEGs. One method for generating such molecules involves the formation of a branched activated PEG in which two or more PEGs are attached to a central core carrying the activated group. The terminal portions of these higher molecular weight PEG molecules, i.e., the relatively non-reactive hydroxyl (—OH) moieties, can be activated, or converted to functional moieties, for attachment of one or more of the PEGs to other compounds at reactive sites on the compound. Branched activated PEGs will have more than two termini, and in cases where two or more termini have been activated, such activated higher molecular weight PEG molecules are referred to herein as, multi-activated PEGs. In some cases, not all termini in a branch PEG molecule are activated. In cases where any two termini of a branch PEG molecule are activated, such PEG molecules are referred to as bi-activated PEGs. In some cases where only one terminus in a branch PEG molecule is activated, such PEG molecules are referred to as mono-activated. As an example of this approach, activated PEG prepared by the attachment of two monomethoxy PEGs to a lysine core which is subsequently activated for reaction has been described (Harris et al., Nature, vol. 2: 214-221, 2003).

The present invention provides another cost effective route to the synthesis of high molecular weight PEG-nucleic acid (preferably, aptamer) conjugates including multiply PEGylated nucleic acids. The present invention also encompasses PEG-linked multimeric oligonucleotides, e.g., dimerized aptamers. The present invention also relates to high molecular weight compositions where a PEG stabilizing moiety is a linker which separates different portions of an aptamer, e.g., the PEG is conjugated within a single aptamer sequence, such that the linear arrangement of the high molecular weight aptamer composition is, e.g., nucleic acid-PEG-nucleic acid (-PEG-nucleic acid)$_n$ where n is greater than or equal to 1.

High molecular weight compositions of the invention include those having a molecular weight of at least 10 kDa. Compositions typically have a molecular weight between 10 and 80 kDa in size. High molecular weight compositions of the invention are at least 10, 20, 30, 40, 50, 60, or 80 kDa in size.

A stabilizing moiety is a molecule, or portion of a molecule, which improves pharmacokinetic and pharmacodynamic properties of the high molecular weight aptamer compositions of the invention. In some cases, a stabilizing moiety is a molecule or portion of a molecule which brings two or more aptamers, or aptamer domains, into proximity, or provides decreased overall rotational freedom of the high molecular weight aptamer compositions of the invention. A stabilizing moiety can be a polyalkylene glycol, such a polyethylene glycol, which can be linear or branched, a homopolymer or a heteropolymer. Other stabilizing moieties include polymers such as peptide nucleic acids (PNA). Oligonucleotides can also be stabilizing moieties; such oligonucleotides can include modified nucleotides, and/or modified linkages, such as phosphorothioates. A stabilizing moiety can be an integral part of an aptamer composition, i.e., it is covalently bonded to the aptamer.

Compositions of the invention include high molecular weight aptamer compositions in which two or more nucleic acid moieties are covalently conjugated to at least one polyalkylene glycol moiety. The polyalkylene glycol moieties serve as stabilizing moieties. In compositions where a polyalkylene glycol moiety is covalently bound at either end to an aptamer, such that the polyalkylene glycol joins the nucleic acid moieties together in one molecule, the polyalkylene glycol is said to be a linking moiety. In such compositions, the primary structure of the covalent molecule includes the linear arrangement nucleic acid-PAG-nucleic acid. One example is a composition having the primary structure nucleic acid-PEG-nucleic acid. Another example is a linear arrangement of: nucleic acid-PEG-nucleic acid-PEG-nucleic acid.

To produce the nucleic acid-PEG-nucleic acid conjugate, the nucleic acid is originally synthesized such that it bears a single reactive site (e.g., it is mono-activated). In a preferred embodiment, this reactive site is an amino group introduced at the 5'-terminus by addition of a modifier phosphoramidite as the last step in solid phase synthesis of the oligonucleotide. Following deprotection and purification of the modified oligonucleotide, it is reconstituted at high concentration in a solution that minimizes spontaneous hydrolysis of the activated PEG. In a preferred embodiment, the concentration of oligonucleotide is 1 mM and the reconstituted solution contains 200 mM NaHCO$_3$-buffer, pH 8.3. Synthesis of the conjugate is initiated by slow, step-wise addition of highly purified bi-functional PEG. In a preferred embodiment, the PEG diol is activated at both ends (bi-activated) by derivatization with succinimidyl propionate. Following reaction, the PEG-nucleic acid conjugate is purified by gel electrophoresis or liquid chromatography to separate fully-, partially-, and un-conjugated species. Multiple PAG molecules concatenated (e.g., as random or block copolymers) or smaller PAG chains can be linked to achieve various lengths (or molecular weights). Non-PAG linkers can be used between PAG chains of varying lengths.

The 2'-O-methyl, 2'-fluoro and other modified nucleotide modifications stabilize the aptamer against nucleases and increase its half life in vivo. The 3'-3'-dT cap also increases exonuclease resistance. See, e.g., U.S. Pat. Nos. 5,674,685;

5,668,264; 6,207,816; and 6,229,002, each of which is incorporated by reference herein in its entirety.

PAG-Derivatization of a Reactive Nucleic Acid

High molecular weight PAG-nucleic acid-PAG conjugates can be prepared by reaction of a mono-functional activated PEG with a nucleic acid containing more than one reactive site. In one embodiment, the nucleic acid is bi-reactive, or bi-activated, and contains two reactive sites: a 5'-amino group and a 3'-amino group introduced into the oligonucleotide through conventional phosphoramidite synthesis, for example: 3'-5'-di-PEGylation as illustrated in FIG. 4. In alternative embodiments, reactive sites can be introduced at internal positions, using for example, the 5-position of pyrimidines, the 8-position of purines, or the 2'-position of ribose as sites for attachment of primary amines. In such embodiments, the nucleic acid can have several activated or reactive sites and is said to be multiply activated. Following synthesis and purification, the modified oligonucleotide is combined with the mono-activated PEG under conditions that promote selective reaction with the oligonucleotide reactive sites while minimizing spontaneous hydrolysis. In the preferred embodiment, monomethoxy-PEG is activated with succinimidyl propionate and the coupled reaction is carried out at pH 8.3. To drive synthesis of the bi-substituted PEG, stoichiometric excess PEG is provided relative to the oligonucleotide. Following reaction, the PEG-nucleic acid conjugate is purified by gel electrophoresis or liquid chromatography to separate fully, partially, and un-conjugated species.

The linking domains can also have one or more polyalkylene glycol moieties attached thereto. Such PAGs can be of varying lengths and may be used in appropriate combinations to achieve the desired molecular weight of the composition.

The effect of a particular linker can be influenced by both its chemical composition and length. A linker that is too long, too short, or forms unfavorable steric and/or ionic interactions with PSMA will preclude the formation of complex between aptamer and PSMA. A linker, which is longer than necessary to span the distance between nucleic acids, may reduce binding stability by diminishing the effective concentration of the ligand. Thus, it is often necessary to optimize linker compositions and lengths in order to maximize the affinity of an aptamer to a target.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

Example 1

Aptamer Selection and Sequences

Example 1A

De Novo Selections for Anti-PSMA Aptamers of rGmH Composition

De novo selections were initiated against an N-terminally 6-His tagged version of the extracellular domain of human PSMA using the Ni-NTA agarose bead pull down selection method described below. A selection using the rGmH pool composition (2'-OH G, 2'O-Me A, C, and U) was initiated. Two aptamers of moderate to high affinity, ARC955 (G2) and ARC956 (G8), were obtained. The sequences and binding data for these two clones are described below.

Protein Purification of ECD of PSMA: An I.M.A.G.E. clone (5202715) encoding full length recombinant human PSMA was purchased from Open Biosystems (Clone EHS1001-18533, Huntsville, Ala.). PCR was used to amplify the extracellular portion of the full length clone. An oligo with an N-terminal histidine tag was designed to engineer a construct which lacks the transmembrane domain residues 1-44. The his-tagged extracellular domain (ECD) was subcloned into the pSecTag2B expression vector (Invitrogen, Carlsbad, Calif.). The ECD of PSMA was purified in house from transfected 293 Freestyle cells (ATCC, Manassas, Va.). The amino acid sequence of the expressed protein comprising an N-terminal linker sequence of DAAQPARRARRTKL followed by eight Histidines is listed below:

```
DAAQPARRARRTKLHHHHHHHHSSNEATNITPKHNMK  (SEQ ID NO 5)
AFLDELKAENIKKFLYNFTQIPHLAGTEQNFQLAKQI
QSQWKEFGLDSVELAHYDVLLSYPNKTHPNYISIINE
DGNEIFNTSLFEPPPPGYENVSDIVPPFSAFSPQGMP
EGDLVYVNYARTEDFFKLERDMKINCSGKIVLARYGK
VFRGNKVKNAQLAGAKGVILYSDPADYFAPGVKSYPD
GWNLPGGGVQRGNILNLNGAGDPLTPGYPANEYAYRR
GLAEAVGLPSIPVHPIGYYDAQKLLEKMGGSAPPDSS
WRGSLKVPYNVGPGFTGNFSTQKVKMHIIHSTNEVTR
IYNVIGTLRGAVEPDRYVILGGHRDSWVFGGIDPQSG
AAVVHEIVRSFGTLKKEGWRPRRTILFASWDAEEFGL
LGSTEWAEENSRLLQERGVAYINADSSIEGNYTLRVD
CTPLMYSLVHNLTKELKSPDEGFEGKSLYESWTKKSP
SPEFSGMPRISKLGSGNDFEVFFQRLGIASGRARYTK
NWETNKFSGYPLYHSVYETYELVEKFYDPMFKYHLTV
AQVRGGMVFELANSIVLPFDCRDYAVVLRKYADKIYS
ISMKHPQEMKTYSVSFDSLFSAVKNFTELASKFSERL
QDFDKSNPWLRMMNDQLMFLERAHDPLGLPDRPFYRH
VIYAPSSHNKYAGESFPGIYDALFDIESKVDPSKAWG
EVKRQIYVAAFTVQAAAETLSEVA
```

Pool Preparation. A DNA template with the sequence 5'-TAATACGACTCACTATAGGGAGAG-GAGAGAACGTTCTAC(N30)GGTCGATCGATCGA TCATCGATG-3' (ARC356) (SEQ ID NO 6) was synthesized using an ABI EXPEDITE™ DNA synthesizer, and deprotected by standard methods. The templates were amplified with the primers 5'-TAATACGACTCACTATAGGGAGAG-GAGAGAACGTTCTAC-3' (SEQ ID NO 7) and 5'-CATC-GATGATCGATCGATCGACC-3' (SEQ ID NO 8) and then used as a template for in vitro transcription with T7 RNA polymerase (Y639F). Transcriptions were done using 200 mM HEPES, 40 mM DTT, 2 mM spermidine, 0.01% TritonX-100, 10% PEG-8000, 9.6 mM $MgCl_2$, 2.9 mM $MnCl_2$, 2 mM 2'-OMe-CTP, 2 mM 2'-OMe-UTP, 2 mM 2'-OH GTP, 3 mM 2'-OMe-ATP, 0.01 units/μL inorganic pyrophosphatase, and T7 polymerase (Y639F), and approximately 1 μM template DNA.

SELEX™. The selection was initiated by incubating of $2 \times 10^{14}$ molecules of 2'-OH G, 2'-OMe A, C, U modified ARC356 pool (rGmH composition) with 20 pmoles of ECD PSMA protein in a final volume of 100 μl selection buffer (1×SHMCK buffer: 20 mM Hepes, 120 mM NaCl, 5 mM KCl, 1 mM $MgCl_2$, 1 mM $CaCl_2$, pH 7.4) with trace amounts of α-$^{32}$P rGTP labeled RNA for 1 hour at room temperature. RNA-protein complexes and unbound RNA molecules were separated using 100 μl of Ni-NTA (Qiagen, Valencia, Calif.) bead slurry that was pre-washed and equilibrated with 3×300 μl of SHMCK buffer. The RNA/protein solution was then added to the beads and bound for 1 hour at room temperature. The beads were then washed with 2×500 µl of 1×SCHMK buffer, which was removed by filtering beads/wash solution through a 0.2 µM filter (Millipore, Billerica, Mass.) The RNA was eluted from the beads by addition of 2×100 µL of 1×SCHMK buffer additionally containing 250 mM Imidazole pH 7.4.

Eluted protein was extracted from the RNA mixture with phenol:choloroform, and the pool RNA was precipitated (1 µL glycogen, 1.5 volume isopropanol). The RNA was reverse transcribed with the ThermoScript RT-PCR™ system (Invitrogen, Carlsbad, Calif.) according to the manufacturer's instructions, using the 3' primer according to SEQ ID NO 8. The cDNA was amplified by PCR (20 mM Tris pH 8.4, 50 mM KCl, 2 mM MgCl2, 0.5 µM 5' primer SEQ ID NO 7, 0.5 µM 3' primer SEQ ID NO 8, 0.5 mM each dNTP, 0.05 units/µL Taq polymerase (New England Biolabs, Beverly, Mass.). Templates were transcribed using $^{32}$P GTP body labeling overnight at 37° C. The reactions were desalted using Centrisep Spin columns (Princeton Separations, Princeton, N.J.) according to the manufacturer's instructions and purified on a denaturing polyacrylamide gel.

Subsequent rounds were repeated using the same method as for Round 1, but with the addition of a negative selection step. Prior to incubation with protein target, the pool RNA was incubated for 15 minutes with 100 µl of Ni-NTA beads and 1×SCHMK to select against non-specific binding. After incubation, the RNA was removed from the beads and brought forward to the positive selection step.

The pool RNA was gel purified every round. Transcription reactions were quenched with 50 mM EDTA and ethanol precipitated then purified on a 1.5 mm denaturing polyacrylamide gels (8 M urea, 10% acrylamide; 19:1 acrylamide:bisacrylamide). Pool RNA was removed from the gel by passively eluting gel fragments in 300 mM NaAc and 20 mM EDTA overnight. The eluted material was precipitated by adding 2.5 volumes of ethanol and 1 µl of glycogen.

The protein concentration was kept at 200 nM throughout the selection. The pool concentration was not quantified each round, but half of the previous round's yield was carried forward to the next round, ensuring that the RNA pool is in excess over the 200 nM ECD PSMA. Competitor tRNA was added to the binding reactions at 0.1 mg/mL beginning at Round 2. After 9 rounds of selection were completed, the pool was sequenced and screened for clones. The progress of the selection, outlined in Table 1 below, was monitored via measuring the percentage of input pool RNA eluted from the Ni-NTA beads during the positive selection step. In Table 1 below, PCR Threshold is defined as the number of PCR amplification cycles it takes such that the intensity of the PCR band on a 4% agarose E-Gel (Invitrogen, Carlsbad, Calif.) is equal to the 100 bp marker lane (Invitrogen).

TABLE 1 rGmH Selection Summary

| Round # | protein type | protein conc (nM) | tRNA conc (mg/mL) | Negative Selection | % elution | PCR Threshold |
|---|---|---|---|---|---|---|
| 1 | ECD PSMA | 200 | 0 | none | 4.20 | 18 |
| 2 | ECD PSMA | 200 | 0.1 | Ni-NTA beads | 6.90 | 15 |
| 3 | ECD PSMA | 200 | 0.1 | Ni-NTA beads | 4.04 | 16 |
| 4 | ECD PSMA | 200 | 0.1 | Ni-NTA beads | 3.12 | 15 |
| 5 | ECD PSMA | 200 | 0.1 | Ni-NTA beads | 6.68 | 15 |
| 6 | ECD PSMA | 200 | 0.1 | Ni-NTA beads | 2.55 | 15 |
| 7 | ECD PSMA | 200 | 0.1 | Ni-NTA beads | 1.77 | 15 |
| 8 | ECD PSMA | 200 | 0.1 | Ni-NTA beads | 0.62 | 15 |
| 9 | ECD PSMA | 200 | 0.1 | Ni-NTA beads | .40 | 15 |

Dot Blot Binding Analysis. Dot blot binding assays were performed throughout the selections to monitor the protein binding affinity of the pools. For initial pool screening, trace $^{32}$P-labeled pool RNA was combined with PSMA and incubated at room temperature for 30 min in 1×SHMCK buffer pH 7.4 (20 mM Hepes pH 7.4, 120 mM NaCl, 5 mM KCl, 1 mM MgCl$_2$, 1 nM CaCl$_2$) plus 0.1 mg/mL tRNA in a final volume of 30 µl. The mixture was applied to a dot blot apparatus (Schleicher and Schuell Minifold-1 Dot Blot, Acrylic, Keene, N.H.), assembled (from top to bottom) with nitrocellulose, nylon, and gel blot membranes. RNA that is bound to protein is captured on the nitrocellulose filter; whereas the non-protein bound RNA is captured on the nylon filter. The selection pool was assayed at Round 9, which showed negligible binding over background. The Round 9 pool was cloned and screened in a single point dot blot assay using 100 nM PSMA (0 nM PSMA was used as a negative control). Clone transcripts were 5'end labeled with $^{32}$-P ATP. Likely binders were than assayed for $K_D$ determination by the blot assay conditions described directly above, but without tRNA, using an 8 point PSMA titration with a constant RNA concentration. Assay results for the 2 best clones, ARC955 (G2) and ARC956 (G8), out of a total of 25 clones tested are shown in Table 2 ($K_D$ values reported were generated without tRNA. Including tRNA may increase $K_D$ measurements if it competes for binding). Both of the clones screened were unique sequences in the Round 9 selection pool.

The nucleic acid sequences of the rGmH aptamers are listed in Table 3 below. The unique sequence of each aptamer begins at nucleotide 19 immediately following the 5' fixed sequence 5'-UAAUACGACUCACUAUAG-3' (SEQ ID NO 9), and runs until it meets the 3'fixed nucleic acid sequence 5'-GGUCGAUCGAUCGAUCAUCGAUG-3' (SEQ ID NO 10). Unless noted otherwise, individual sequences listed below in Table 3 are represented in the 5' to 3' orientation and were selected under rGmH SELEX™ conditions wherein adenosine triphosphate, cytidine triphosphate and uridine triphosphate are 2'-OMe and guanosine triphosphate is 2'-OH. In some embodiments, the invention comprises an aptamer with a nucleic acid sequences as described in Table 2 below. In other embodiments, the nucleic acid sequence of the aptamers described in Table 2 below additionally comprises a 3' cap (e.g., an inverted dT cap (3T)), and/or a 5' amine (NH$_2$) modification to facilitate chemical coupling, and/or conjugation to a high molecular weight, non-immunogenic compound (e.g., PEG).

TABLE 2

Binding Data for Round 9 PSMA rGmH Clones

| SEQ ID NO | Clone | $K_D$ (nM) |
|---|---|---|
| 11 | ARC955 | 9 |
| 12 | ARC956 | 16 |

TABLE 3

Sequences from Round 9 PSMA rGmH Selection:

```
ARC955 (G2)
UAAUACGACUCACUAUAGGGAGAGGAGAGAACGUUCU   SEQ ID NO 11
ACUAUGGGUGGCUGGGAGGGGAAGAGGGAGUAGGUCG
AUCGAUCGAUCAUCGAUG

ARC956
UAAUACGACUCACUAUAGGGAGAGGAGAGAACGUUC    SEQ ID NO 12
UACACAUGGGUCGGGUGAGUGGCAAAGGAAUAGGUCG
AUCGAUCGAUCAUCGAUG
```

Example 2

Composition and Sequence Optimization

In Example 2A, the PSMA specific aptamer designated ARC955 (G2) that was derived from the rGmH selection described in Example 1 was further optimized via synthetic truncations. The work in Example 2B-Example 2E describes the results of efforts to improve clone A9, an existing PSMA specific aptamer of rRfY composition (2'-OH purines (A and G) and 2'-fluoro pyrimidines (C and U)), denoted as the A9 clone herein, with the following sequence consisting of: 5'GGGAGGACGAUGCGGACCGAAAAAGAC-CUGAfCfUfUfCfUAfUAfCfUAAGfUfCfUAf CGfU-fUfCfCfCAGAfCGAfCfUfCGfCfCfCGA3' (SEQ ID NO 168) through post-SELEX™ optimization. The A9 clone was described in a patent application having U.S. Ser. No. 09/978,969 filed Oct. 16, 2001 herein incorporated by reference in its entirety. The A9 clone (SEQ ID NO 168) was extensively optimized via synthetic truncations (Example 2B), cell-surface doped SELEX™ (Example 2C), engineered mutations (Example 2D), and engineered backbone modifications (Example 2E).

Example 2A

Minimization and Optimization of ARC955 (G2) Aptamer

Figure 5A:
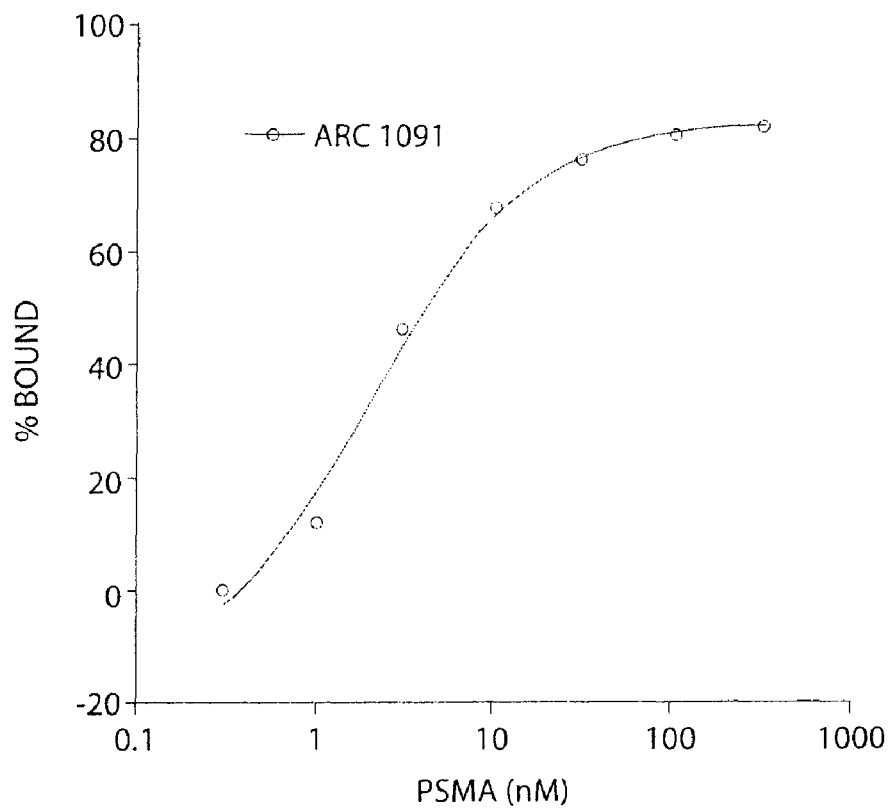
FIG. 5A is a PSMA binding curve for ARC1091 in a dot blot binding assay. PSMA concentration is shown on the X-axis versus % aptamer bound on the Y-axis.
Figure 5B:
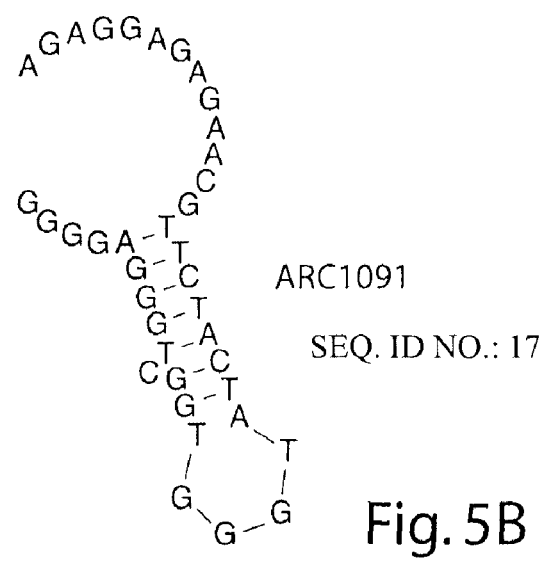
FIG. 5B is an illustration of the predicted minimum free energy structure of ARC1091.

In order to identify the core structural elements required for ARC955 binding to PSMA, the 3'-boundaries of the clone was determined through alkaline hydrolysis. The parent RNA transcript was labeled at the 5'-end with $\gamma$-$^{32}$P ATP and T4 polynucleotide kinase. Radiolabeled ligands were subjected to partial alkaline hydrolysis and then selectively bound in solution to ECD PSMA (purified in house) at 100 nM before being passed through nitrocellulose filters (Centrex MF 1.5 mL, 0.45 µm, Schleicher & Schuell, Keene N.H.). Retained oligonucleotides were resolved on 8% denaturing polyacrylamide gels. The smallest oligonucleotide bound to PSMA defined the 3'-boundary. On the basis of the boundary experiments as well as visual inspection of predicted folds, truncated constructs were synthesized. Clones were then assayed by dot blot as previously described to determine their $K_D$. ARC1091 represents the smallest minimer tested that maintains the full binding capacity of the aptamer. The binding curve for ARC1091 in the dot blot assay is depicted in FIG. 5A, and the predicted secondary structure of ARC1091 is depicted in FIG. 5B. The $K_D$ and maximum % bound for the 3 minimized constructs with the overall highest PSMA affinity, as determined by a dot blot binding assay, are listed in Table 4. For the minimized rGmH aptamers described in Table 5 below, the guanosine triphosphates are 2'-OH and the adenosines triphosphates, cytidine triphosphates and uridine triphosphates are 2'-OMe. Unless noted otherwise, the individual sequences are represented in the 5' to 3' orientation. In some embodiments, the invention comprises aptamers with a nucleic acid sequence as described in Table 4 below. In some embodiments, the nucleic acid sequence of an aptamer described in Table 4 below additionally comprises a 3' cap (e.g., an inverted dT cap), and/or 5' amine ($NH_2$) modification to facilitate chemical coupling, and/or conjugation to a high molecular weight, non-immunogenic compound (e.g., PEG). In other embodiments, the nucleic acid sequence described in Table 4 lacks the indicated 3' cap (e.g., an inverted dT cap (3T)) and/or 5' amine ($NH_2$) modification to facilitate chemical coupling.

TABLE 4 rGmH Minimer Binding Data:

| SEQ ID NO | Minimer | Length (nt) | $K_D$ (nM) | Max % bound |
|---|---|---|---|---|
| 14 | ARC725 | 40 | no binding | no binding |
| 15 | ARC1088 | 23 | 2.1 | 33 |
| 16 | ARC1089 | 33 | 9.3 | 22 |
| 17 | ARC1091 | 38 | 3.1 | 52 |

Max % Bound refers to the highest % of minimer bound to target protein, as assayed by Dot Blot.

TABLE 5

Sequences of rGmH minimers

```
ARC723
CUACUAUGGGUGGCUGGGAGGGGAAGAGGGAGUAG      SEQ ID NO 13

ARC725
CUACUACACAUGGGUCGGGUGAGUGGCAAAGGAAUAG    SEQ ID NO 14
UAG

ARC1088
GGGUGGCUGGGAGGGGAAGAGGG                  SEQ ID NO 15

ARC1089
CUACUGGGUGGCUGGGAGGGGAAGAGGGAGUAG        SEQ ID NO 16

ARC1091
AGAGGAGAGAACGUUCUACUAUGGGUGGCUGGGAGGG    SEQ ID NO 17
G

ARC1142 (ARC1091 incorporating a
5'-amine linker)
NH2-AGAGGAGAGAACGUUCUACUAUGGGUGGCUGGG    SEQ ID NO 18
AGGGG ARC1786 (ARC1091 incorporating
5'-amine linker and 3' inverted dT)
NH2-AGAGGAGAGAACGUUCUACUAUGGGUGGCUGGG    SEQ ID NO 19
AGGGG-3T
```

Example 2B

Truncation of the A9 Aptamer

The parent A9 aptamer sequence (SEQ ID NO 168) is predicted by the MFOLD algorithm implemented in the RNAStructure program v. 4.11 to fold into a partially mismatched hairpin that encompasses almost the entire molecule. A series of truncated constructs were designed, in which self-pairing nucleotides from the 5'- and 3'-ends were simultaneously removed, chemically synthesized using conventional solid-phase phosphoramidite-based synthesis, and tested. In the design of some of the truncated A9 aptamers, see e.g. ARC591, additional bases were added to the 3' and 5' ends of the truncate, where the bases added to the 5' end were capable of forming Watson-Crick base pairs with those added to the 3' end thereby increasing the length of stem structure. Truncated aptamers were 5'-labeled with fluorescein and tested for binding in to LNCaP cells (PSMA+) in the FACS assay described below. PC-3 cells (PSMA−) were used as a control cell line. The sequences of the truncated A9 aptamers designed are listed below in Table 6 below.

To accomplish 5'-fluorescein labeling, aptamers were synthesized with a 5'-amine and then modified post-solid phase synthesis. The required aptamer was dissolved to a concentration of ~10-50 mg/mL in 25 mM phosphate buffer, pH 7.4. The small molecule, NHS ester of fluorescein, was dissolved to a concentration of 10 mg/mL in DMSO. 1.5 Molar equivalents were added to the aptamer and the solution vortexed for ~15 seconds. The reaction was allowed to proceed in the dark at room temperature for 1 hour and then a 5 µL aliquot was withdrawn, diluted with water and analyzed by HPLC. Additional equivalents of the small molecule were added until the reaction was complete by HPLC. Excess small molecules were removed by gel filtration.

To prepare aptamers for the FACS assay, PSMA aptamers were serially diluted (0-1 uM) in FACS buffer (1×DPBS w/Ca$^{++}$/Mg$^{++}$ (Gibco, Carlsbad, Calif.) supplemented with 10 mg/mL salmon sperm DNA & 0.2% Na Azide), in a V-bottom 96 well plate, at the concentrations to be tested. LNCaP and PC-3 cells (ATCC, Manassas, Va.) were harvested with trypsin, and 200,000 cells/well were counted, washed once with 1×DPBS (with Ca$^{++}$ and Mg$^{++}$) and resuspended in 200 µl of FACS Buffer. The 200 µl of cells in FACS buffer were added to individual wells of a new 96 well plate, pelleted by centrifugation (1300 rpm for 5 minutes), and resuspended in 100 µl of the appropriate concentration of diluted aptamer. FACS buffer, c-PSMA antibody (3C6) (Northwest Biotherapeutics, Bothell, Wash., Cat #: 60-5002) and an irrelevant fluorescein isothiocyanate ("FITC") mouse IgG1 isotype control antibody (BD Pharmingen, San Diego, Calif., Cat#: 554679) were used as controls. The wells of aptamer/cell mixture were incubated at room temperature for 20-30 minutes.

After incubation, 180 µl of FACS buffer (plus 10 mg/mL ssDNA, and 0.2% Na Azide) was added to each well to quench the reaction and cells were pelleted by centrifugation. Anti-fluorescein/Oregon Green®, rabbit IgG fraction, Alexa Fluor® 488 conjugate (Molecular Probes, Eugene, Oreg., Cat#: A11090) was diluted 1:100 in FACS buffer (100 µl/well) as the secondary antibody for the aptamer-FITC conjugates and FITC-mouse IgG isotype control. FITC Rat anti-mouse IgG1 (A85-1) (BD Pharmingen, San Diego, Calif., Cat#: 553443) was diluted in 1:100 in FACS Buffer as the secondary for the α-PSMA antibody. After centrifugation, the cell pellets were resuspended in 100 µl of the appropriate diluted secondary antibody, and incubated 10 minutes at room temperature. After incubation, 180 µl of FACS buffer was added to each well to quench the reaction, and cells were pelleted by centrifugation.

A tertiary antibody which recognizes the Alexa Fluor® 488 goat anti-rabbit IgG was prepared to further amplify the Alexa Fluor signal. Alexa Fluor® 488 goat anti-rabbit IgG (H+L) (Molecular Probes, Eugene, Oreg., Cat#: A 11034) was diluted 1:100 in FACS buffer, and the pelleted cells were resuspended in 100 µl of the tertiary antibody and incubated for 10 minutes at room temperature. After incubation, 180 µl of FACS buffer was added to each well to quench the reaction, and cells were pelleted by centrifugation, and resuspended in 200 µl of FACS buffer with 1 µl/mL of propidium iodide ("PI") to allow for live/dead cell staining.

Figure 6:
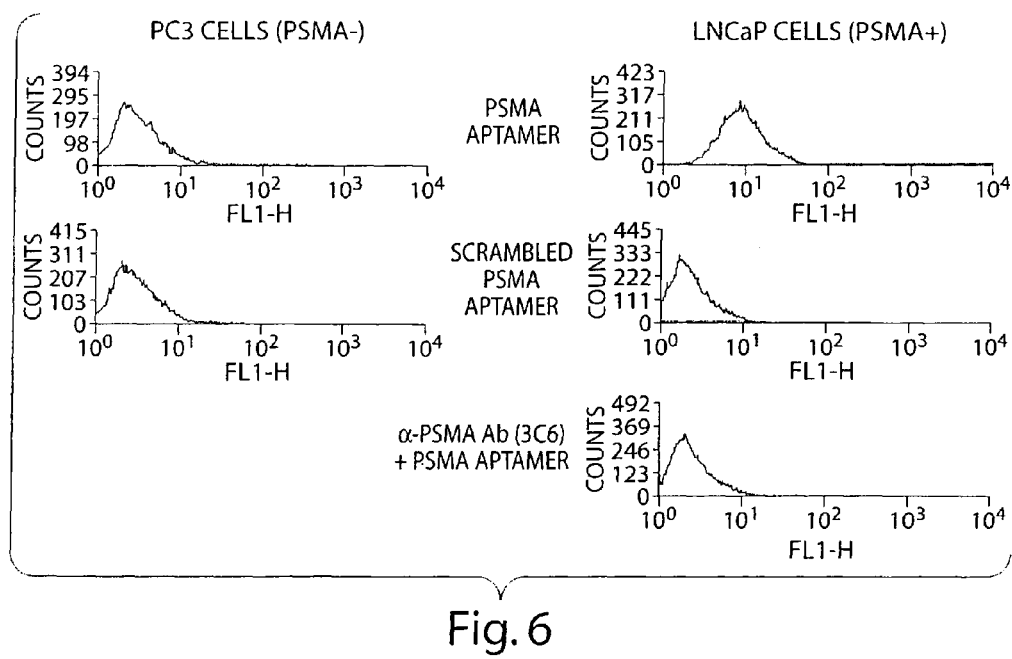
FIG. 6 shows the histogram plots of fluorescently labeled PSMA aptamer binding to LNCaP (PSMA+) cells and not PC-3 (PSMA-) cells by FACS analysis (scrambled PSMA aptamer is a negative control). Competition of the PSMA aptamer fluorescent signal by αPSMA antibody demonstrates that the clones bind via a specific interaction with PSMA

Cell samples were analyzed on a FACS Scan machine (Becton Dickinson, San Jose, Calif.) under the following parameters: FSC/SSC, FL-1/FSC, FL-3/FSC. The unstained and/or isotype controls were used to establish gating parameters, and the data was analyzed using Cell Quest Pro software version 5.1.1 (Becton Dickinson Immunocytometry Systems, San Jose, Calif.). FIG. 6 is an example of the typical results for PSMA specific aptamers in the LNCaP FACS assay, which depicts by histogram plot the A9 aptamer (SEQ ID NO 168) binding to LNCaP (PSMA+) cells, but not to PC-3 (PSMA−) cells, using a scrambled A9 aptamer as a negative control. In addition, FIG. 8 shows that competition of the A9 fluorescent signal by the αPSMA antibody demonstrates that the clones bind via a specific interaction with PSMA rather than with any other cell surface component.

Figure 7A:
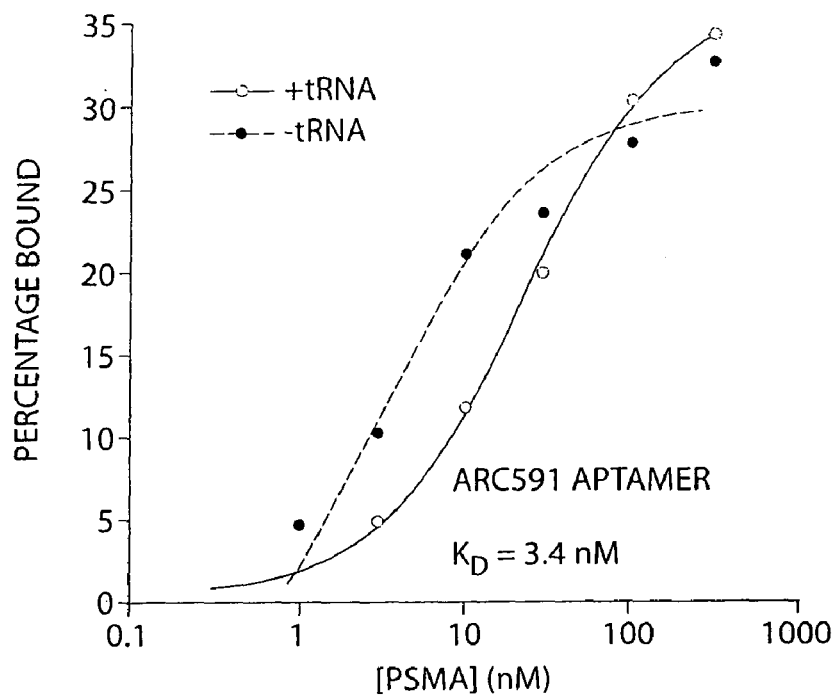
FIG. 7A is a PSMA binding curve for ARC591 in a dot blot binding assay (+/−tRNA), showing that ARC591 has a $K_D$ of 3.4 nM (without tRNA)
Figure 7B:
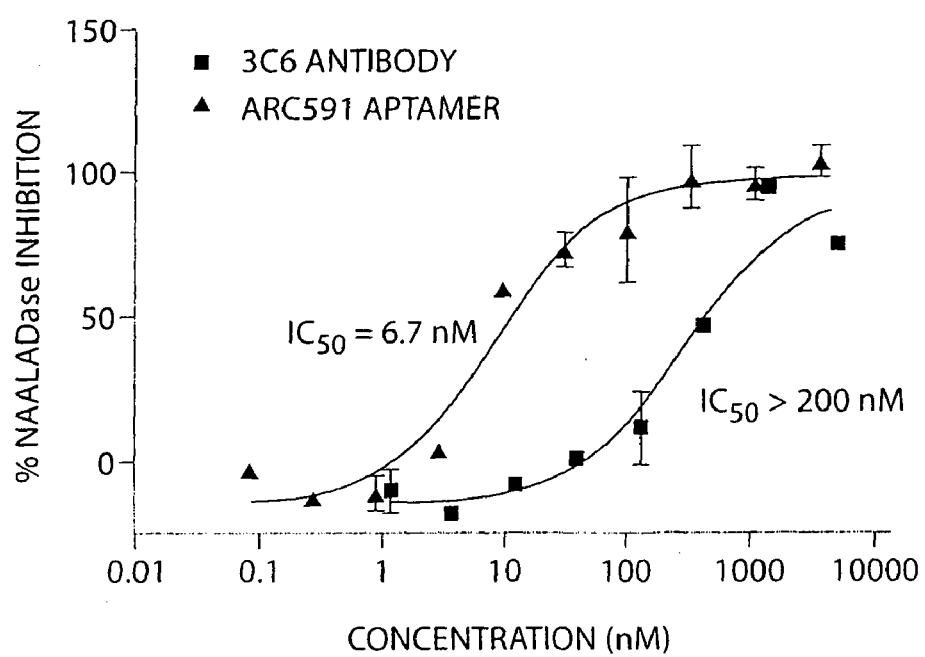
FIG. 7B is a graph showing ARC591 inhibits NAALADase activity better than an anti-PSMA antibody (3C6), with an apparent $IC_{50}$ of 6.7 nM.
Figure 7C:
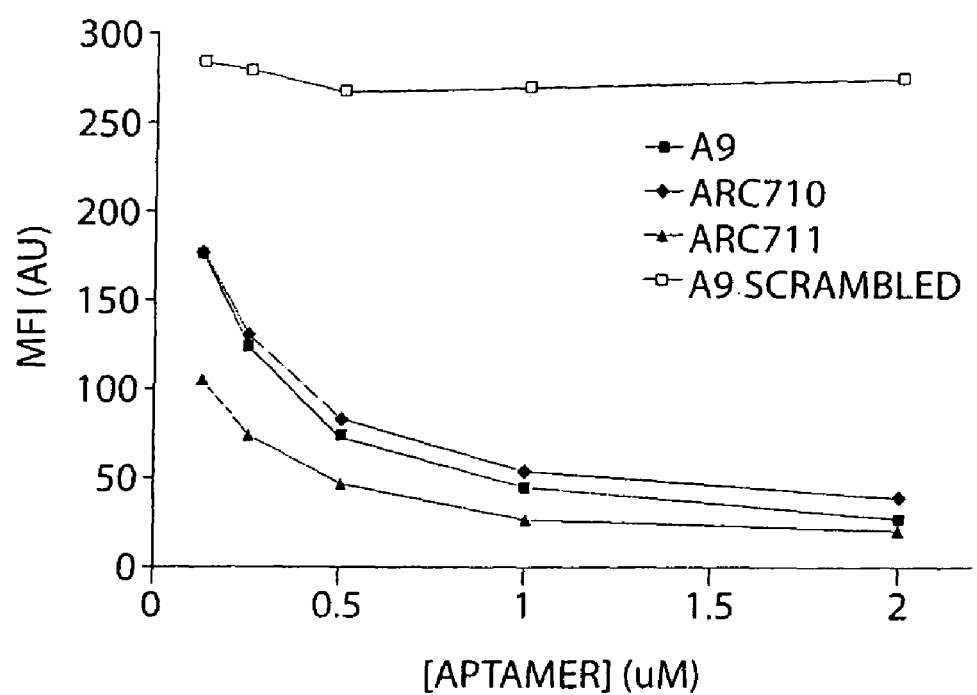
FIG. 7C is a graph showing that fluorescently labeled A9 minimers, ARC710 and ARC711, effectively competes with fluorescently labeled anti-PSMA antibody for binding to the surface of LNCaP cells as assessed by FACS analysis (scrambled A9 is a negative control).

From these studies, a 48-nt. 'minimer' ARC591 was identified that retained full functional activity in the LNCaP FACS assay described above, and a NAALADase inhibition assay (described below in Example 2D), and was shown to bind PSMA by the dot blot assay previously described, with a K$_D$ of 3.4 nM, as shown in FIG. 7.

Unless noted otherwise, the individual sequences listed below in Table 6 are represented in the 5' to 3' orientation and were derived from aptamers wherein all adenosine triphosphate and guanosine triphosphate are 2'-OH, and cytidine triphosphate and uridine triphosphate are 2'-fluoro. In some embodiments, the invention comprises aptamers with a nucleic acid sequences as described in Table 6 below. In some embodiments, the nucleic acid sequences of the aptamers described in Table 6 below additionally comprise a 3' cap (e.g., an inverted dT cap (3T)), and/or 5' amine (NH$_2$) modification to facilitate chemical coupling, and/or conjugation to a high molecular weight, non-immunogenic compound (e.g., PEG). In other embodiments, the nucleic acid sequences described in Table 6 lack the indicated 3' cap (e.g., an inverted dT cap) and/or 5' amine (NH$_2$) modification to facilitate chemical coupling.

Lower case letters "f" and "m" preceding A, C, G, or U in ARC711 (SEQ ID NO 26) denote 2'-fluoro and 2-O-methyl substitutions respectively, C6-FAM denotes 5'-fluoroscein.

TABLE 6

Sequences of truncated A9 aptamers:

ARC533
CGGACCGAAAAAGACCUGACUUCUAUACUAAGUCUAC   SEQ ID NO 20
GUUCCG-3T

ARC536
CGGACCGAAAAAGACCUGACUUCUAUACUAAGUCUAC   SEQ ID NO 21
GUUCCG

TABLE 6-continued

Sequences of truncated A9 aptamers:

ARC591
GGAGGACCGAAAAAGACCUGACUUCUAUACUAAGUCU SEQ ID NO 22
ACGUUCCUCCA

ARC2038
NH2-GGAGGACCGAAAAAGACCUGACUUCUAUACUAA SEQ ID NO 23
GUCUACGUUCCUCCA

ARC2039
NH2-GGAGGACCGAAAAAGACCUGACUUCUAUACUAA SEQ ID NO 24
GUCUACGUUCCUCC-3T

ARC710
C6 FAM-GGAGGACCGAAAAAGACCUGACUUCUAUAC SEQ ID NO 25
UAAGUCUACGUUCCUCC-3T

ARC711
c6 fam-mCmGmGmAfCfCmGAAAAmAmGmAmCfCfU SEQ ID NO 26
GAfCfUfUfCfUAfUAfCfUAAmGmUmCmUAfCmGfU
mUmCmCmG-3T

Example 2C

Cell-Surface Doped SELEX™

In this example, a doped reselection was used to explore the sequence requirements within an active clone or minimer. Doped selections are carried out with a synthetic, degenerate pool that has been designed based on a single sequence (here, ARC591). The level of degeneracy usually varies from 70% to 85% wild type nucleotide. In general, neutral mutations are observed but in some cases sequence changes can result in improvements in affinity. The composite sequence information can then be used to identify the minimal binding motif and aid in optimization efforts.

Using the doped reselection strategy based on the sequence of ARC591, sequence variants were identified that (1) improved PSMA-directed binding to cells expressing the protein, (2) minimized non-specific cell binding, and (3) provide information relating to the secondary and tertiary structural requirements of the aptamer to guide further optimization.

Pool Preparation. A DNA template consisting of the sequence of ARC591, flanked by arbitrary constant primer sequences shown separately not to interfere with PSMA binding, was synthesized using an ABI EXPEDITE™ DNA synthesizer, and deprotected by standard methods. 5'-CGCAAG-GACGAAGGGAGGACGATGCGGACCGAAAAAGACC-TGACTTCTATACTA AGTCTACGTTCCCAGACGACTC-GCCCGAGGTCGATTCC-3' (ARC292) (SEQ ID NO 27)

The nucleotides in bold had an 85% chance of being the indicated residue and a 5% chance of being one of the other 3 nucleotides (see also FIG. 6B). The DNA template was amplified using the primers 5'TAATACGACTCACTATAG-GCAAGGACGAAGGGAGG3' (SEQ ID NO 28,) and 5'-TGGAATCGACCTCGGGCG-3' (SEQ ID NO 29) and then used as a template for in vitro transcription using Y639F mutant T7 RNA polymerase. Transcriptions were done using $\alpha^{32}$P ATP body labeling overnight at 37° C. (4% PEG-8000, 40 mM Tris pH 8.0, 12 mM MgCl$_2$, 1 mM spermidine, 0.002% Triton X-100, 3 mM 2'OH purines, 3 mM 2° F. pyrimidines, 25 mM DTT, 0.01 units/µl inorganic pyrophosphatase, T7 Y639F mutant RNA polymerase, 5 µCi $\alpha^{32}$P ATP). The reactions were desalted using Bio Spin columns (Bio-Rad, Hercules, Calif.) according to the manufacturer's instructions.

Figure 8A:
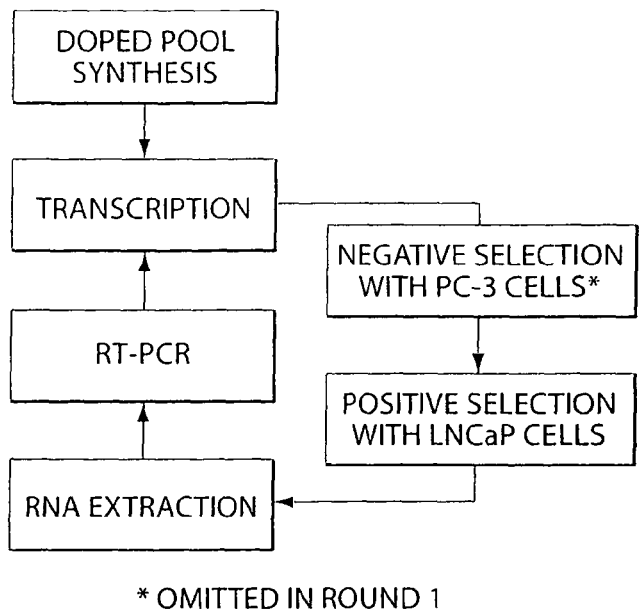
FIG. 8A is a flow chart of cell surface SELEX™.

This doped pool was iteratively enriched using cell surface SELEX™ as described in detail below for preferential binding to LNCaP cells and minimal binding to PC-3 cells. An outline of the doped re-selection process is shown in FIG. 8A. To specifically drive the enrichment of aptamer variants capable of binding to PSMA endogenously expressed in tumor cells, the SELEX™ pool was partitioned using PSMA (+) LNCaP cells (positive selection) and PSMA(−) PC-3 cells (negative selection). In each round, cells were harvested for partitioning as follows. Cells grown in tissue culture flasks were washed with PBS, combined with trypsin-EDTA, and incubated at 37° C. for typically less than 1 minute until cells started to dissociate from their plates. The cells were subsequently diluted with an approximately equivalent volume of media (RPMI1640+fetal calf serum) and collected by centrifugation at 1,500 rpm for 1.5 min. Following removal of the supernatant, cells were washed once with media and twice with 1×PBS (plus Mg$^{++}$Ca$^{++}$)(Gibco #14040-133). Following cell harvesting, cells were prepared prior to exposure to the SELEX™ pool. Each round of cell SELEX™ typically used 2.3×10$^7$ LNCaP cells for the positive selection and 1.1× 10$^7$ PC-3 cells for the negative selection. Harvested cells were concentrated by centrifugation, gently resuspended in cell binding buffer at a concentration of 1-2×10$^6$ cells/mL (cell binding buffer=0.1% BSA, 0.2 mg/mL salmon sperm DNA, 0.2 mg/mL yeast tRNA in 0.9×PBS), and rotated slowly at 4° C. for 20 min. Following this incubation, 1 U/µl SUPERase (Ambion, Austin, Tex., #2696) and 0.01% NaN$_3$ were added to the cells and rotating continued for an additional 10 min at 4° C.

Negative SELEX™. In cell surface SELEX™ rounds in which negative selective pressure was applied (rounds 2-6), the SELEX™ pool was exposed initially to PC-3 cells prepared as described above in a pre-clearing step. The PC-3 cells were split into two equal fractions, diluted to 600 µl with CBBA (CBBA=cell binding buffer+additives=10 ml cell binding buffer, 100 µl 1% NaN$_3$, and 250 µl 20 U/µl SUPERase), combined with the SELEX™ pool in a minimal volume, and incubated at 4° C. for 30 minutes. Cells were spun down (1,500 rpm, 2 minutes) and the supernatant collected for the positive selection step.

Positive SELEX™. Supernatant from the negative SELEX™ step (approximately 550 µl) was combined with pre-blocked, pelleted LNCaP cells prepared as described above. Cells were washed twice with CBBA to remove the unbound fraction of the SELEX™ pool and then incubated at 4° C. for 30 min. In later rounds (rounds 5 and 6), the stringency of selection was increased by the inclusion of an additional non-amplifiable competitor (ARC591) that could competitively displace molecules transiently dissociated from cells (driving the selection of molecules with intrinsically slow off-rates). Feasibility studies showed that a significant fraction of the SELEX™ pool associated with LNCaP cells after this binding and wash treatment could be attributed to non-specific uptake by cells killed during the preparation phase. To specifically enrich PSMA-associated molecules, FACS was used to sort live and dead cells on the basis of propidium iodide staining (10 µg/ml), specifically collecting 1.5-2×10$^6$ cells with mean fluorescence intensity below an established threshold for dead cells. Collected cells were pelleted by centrifugation and associated SELEX™ pool molecules amplified as described below.

Extraction and amplification. Cell pellets isolated by FACS were resuspended with 500 μl elution buffer (5 M urea, 300 mM NaOAc, 50 mM EDTA, pH 7.4) and RNA was subsequently extracted with 500 μl acid phenol (pH ~5), back extracted with 400 μl Tris-EDTA buffer, and 800 μl chloroform. The supernatant was transferred to a new tube and precipitated with 3 M Na Acetate, 2.5 volumes ethanol, and 1 μl glycogen. The isolated pellet was resuspended with 100 μl water, desalted twice using G25 spin columns (GE, Piscataway, N.J.) and used as subsequent input for a reverse transcription reaction cocktail containing the following: 120 μl extracted RNA, 2.5 μl 100 μM reverse primer 5'-TGGAATC-GACCTCGGGCG-3' (SEQ ID NO 29), 5 μl 10 mM dNTPs. The reaction mixture was incubated at 65° C. for 3 min, followed by addition of the following: 50 μl 5x reverse transcription buffer, 25 μl 0.1 M DTT, 12.5 μl RNAseOUT, 10 μl Thermoscript™ reverse transcriptase (Invitrogen, Carlsbad, Calif. #11146-024), 25 μl H$_2$O. The complete reaction mix was incubated at 65° C. for 60 minutes and heat killed by incubation at 85° C. for 10 minutes.

The cDNA was subsequently amplified by PCR using 1 μl in 25 μl of PCR mix (20 mM Tris pH 8.4, 50 mM KCl, 2 mM MgCl$_2$, 0.5 μM primer check primer sequences 5'TAATAC-GACTCACTATAGGCAAGGACGAAGGGAGG3' (SEQ ID NO 28), 0.5 μM primer 5'TGGAATCGACCTCGGGCG-3' (SEQ ID NO 29), 0.5 mM each dNTP, 0.05 units/μL Taq polymerase (New England Biolabs, Beverly, Mass.)). Standard PCR conditions with an annealing temperature of 52° C. were used. The cycles were repeated until a sufficient amount of PCR product was generated, determined by running an aliquot of the PCR product on a 4% E-Gel (Invitrogen, Carlsbad, Calif.). When the intensity of the band was equal to the 100 bp marker lane, the template was used to prime the next round of transcription. The reactions were desalted using Centricep spin columns (Princeton Separations, Princeton, N.J.) according to manufacturer's instructions and purified on a denaturing polyacrylamide gel in some rounds, as indicated in Table 7.

Figure 8B:
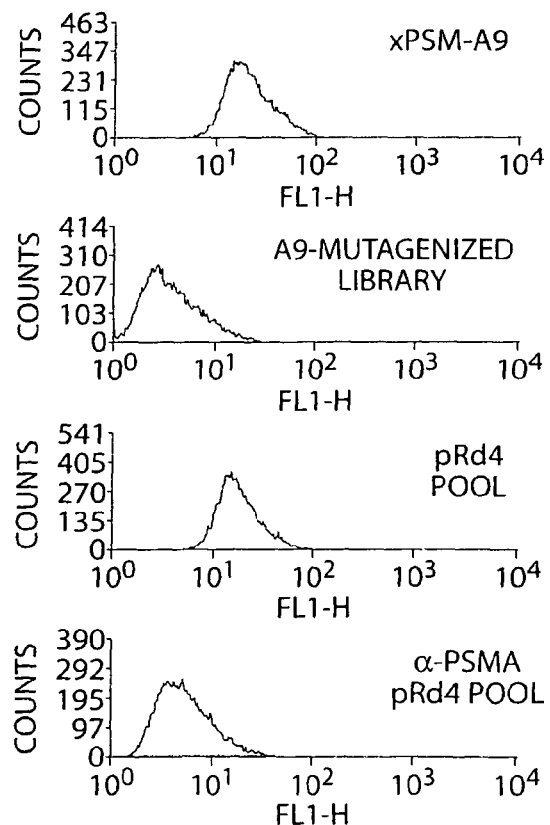
FIG. 8B shows (top to bottom) the histograms plots from FACS analysis of fluorescently labeled A9 aptamer (xPSM-A9), doped pool used to initiate LNCaP cell SELEX™ (A9 mutagenized library), doped pool after four rounds of cell SELEX™ (pRd4), and the effects of competition with an anti-PSMA antibody. After 4 rounds of cell SELEX, the pool is enriched and specific for PSMA specific binding.
Figure 9:
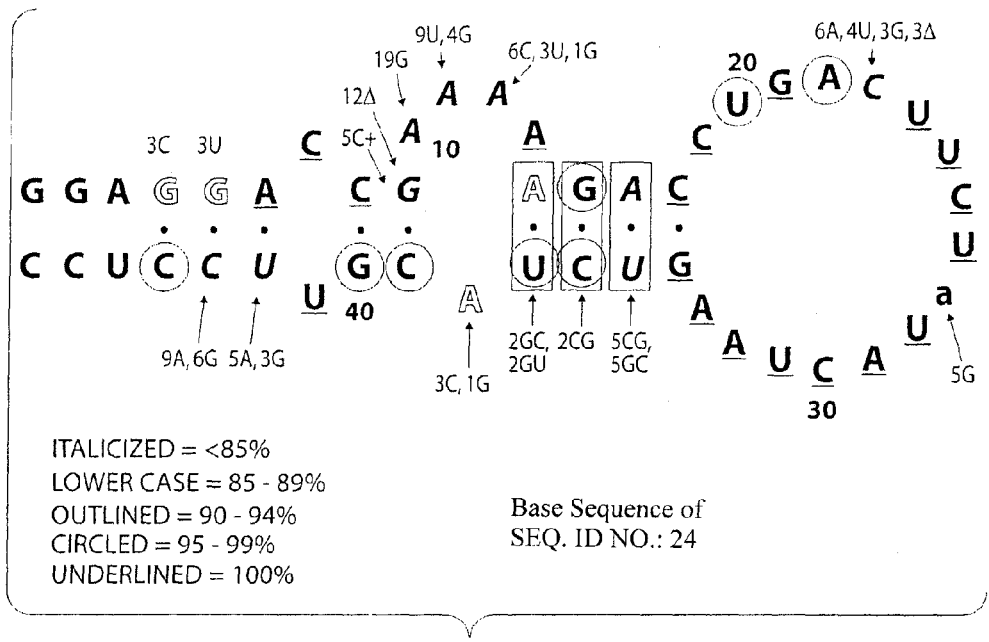
FIG. 9 depicts an analysis of LNCaP binding aptamer sequences identified from Round 6 of the doped cell SELEX™; the indicated coding (italicized, underlined, lower case, circled, or underlined letters) corresponds to nucleotide conservation at each position across each sequenced clone. Nucleotide covariation at pairs of positions consistent with Watson-Crick base pairing are indicated with open boxes. Preferred mutations and their frequency within the set of sequenced clones are indicated alphanumerically for each position where significant sequences biases were observed (e.g., "9A" indicates that 9 of the sequenced clones contained an A instead of the indicated nucleotide in the composite secondary structure).

Table 7 summarizes specific information on the conditions for each round of SELEX™. As shown in FIG. 8B, the starting doped library (A9 mutagenized pool, FIG. 10B) showed no significant LNCaP binding as assessed using fluorescently-labeled transcripts in the LNCaP FACS assay previously described. After 4 rounds of re-selection for LNCaP binding (pRd4, FIG. 10B), the level of binding had returned to levels observed with the original A9 clone (xPSM-A9, FIG. 10B). Competition of the fluorescent signal by an anti-PSMA antibody (αPSMA pRd pool, FIG. 10B) demonstrates that the clones bind via a specific interaction with PSMA rather than with any other cell surface component. Two additional rounds of SELEX™ were carried out under increased stringency conditions to yield aptamers with potentially higher affinity binding to PSMA. The increased stringency conditions followed the standard wash steps which entailed incubating the post-binding cells for 30 minutes with 500 nM non-amplifiable A9 aptamer to block rebinding by aptamer variants that dissociated from PSMA during that time. After a total of 6 rounds of SELEX™, aptamers were subcloned and sequenced. 47 independent clone sequences were obtained and are listed in Table 8. Sequence conservation and Watson-Crick covariation between pairs of nucleotides defined a specific hairpin structure with a highly conserved 16-nt hairpin loop, a less well conserved asymmetric loop, and a highly conserved C:T mismatch (FIG. 9).

TABLE 7

Doped Cell SELEX ™ Summary

| Round | Aptamer gel purified | Aptamer Concentration | Selection Conditions | # of cells sorted | Negative selection/ # PC3 cells |
|---|---|---|---|---|---|
| Rd1 | Yes | 250 nM | Sorted for live cells | 5 × 10$^6$ | No |
| Rd2 | Yes | 50 nM | Sorted for live cells | 2.5 × 10$^6$ | Yes/ 10 × 10$^6$ cells |
| Rd3 | Yes | 50 nM | Sorted for live cells | 2.4 × 10$^6$ | Yes/ 2.4 × 10$^6$ |
| Rd4 | No | 50 nM | Sorted for live cells | 1.5 × 10$^6$ | Yes/ 2.7 × 10$^6$ |
| Rd5 | Yes | 100 nM | Koff selection/ 500 nM A9 | 1.5 × 10$^6$ | Yes/ 1.15 × 10$^7$ |
| Rd6 | No | 50 nM | Koff selection/ 500 nM A9 | 1.5 × 10$^6$ | Yes/ 5.5 × 10$^6$ |

Unless noted otherwise, the individual sequences listed below in Table 8 are represented in the 5' to 3' orientation and were derived from aptamers wherein all adenosine triphosphate and guanosine triphosphate are 2'-OH, and cytidine triphosphate and uridine triphosphate are 2'-fluoro. In some embodiments, the invention comprises aptamers with a nucleic acid sequences as described in Table 8 below. In other embodiments, the nucleic acid sequences of the aptamers described in Table 8 below additionally comprise a 3' cap (e.g., an inverted dT cap (3T)), and/or 5' amine (NH$_2$) modification to facilitate chemical coupling, and/or conjugation to a high molecular weight, non-immunogenic compound (e.g., PEG).

TABLE 8

Sequences from Round 6 Doped Cell SELEX ™:

GGACCGGAAAAGACCUGACUUCUAUACUAAGUCUACG UUCC  SEQ ID NO 30

GGACCGAAAAGACCUGACUUCUAUACUAAGUCUACG UUAC  SEQ ID NO 31

GGACCGAAAAGACCUGACUUCUAUACUAAGUCUACG UUGC  SEQ ID NO 32

GGACCGAAAAGACCUGAAUUCUAUACUAAGUCUACG UUCC  SEQ ID NO 33

GGACCGAACAAGACCUGACUUCUAUACUAAGUCUACG UUCC  SEQ ID NO 34

GGACCGGAAAAGACCUGAUUCUAUACUAAGUCUACGU UCC  SEQ ID NO 35

GGACCGUAAAGACCUGACUUCUAUACUAAGUCUACG UUGC  SEQ ID NO 36

GGACCGAAAAGACCUGACUUCUAUACUAAGGCUACG UUGC  SEQ ID NO 37

GGACCGAACAAGACCUGAUUUCUAUACUAAGUCUACG UUCC  SEQ ID NO 38

GGACCGAAAAGGCGUGACUUCUAUACUAAGCCUACG UUCC  SEQ ID NO 39

TABLE 8-continued

Sequences from Round 6 Doped Cell SELEX ™:

GGACCGUAAAGACCUGACUUCUAUACUAAGUCUACGU UCC  SEQ ID NO 40

GGACCCGAAAAGACCUGACUUCUAUACUAAGUCUACG UUAC  SEQ ID NO 41

GGACCGAACAAGACCUGACUUCUGUACUAAGUCUACG UUCC  SEQ ID NO 42

GGACCGAAUAAGACCUGACUUCUGUACUAAGUCUACG UUCC  SEQ ID NO 43

GGACCGGAAAGGACCUGAUUCUAUACUAAGUCUACGU UCC  SEQ ID NO 44

CGACCGAAAAAGACCUGACUUCUAUACUAAGUCUACG UUA  SEQ ID NO 45

GGACCGGAAAAGACCUGAAUUCUAUACUAAGUCUACG UACC  SEQ ID NO 46

GGACCGAAAAGGACCUGACUUCUAUACUAAGUCCACG UUCC  SEQ ID NO 47

GGACCGAACAAGCCCUGACUUCUAUACUAAGGCUACG UUCC  SEQ ID NO 48

GGACCGGAAAGACCUGACUUCUAUACUAAGUCUACGU UCC  SEQ ID NO 49

GGACCGAGAAAGACCUGAAUUCUAUACUAAGUCUACG UUAC  SEQ ID NO 50

GGACCGUAAAGACCUGACUUCUAUACUAAGUCUACGU GCC  SEQ ID NO 51

GGACCGGAAAAGCCCUGACUUCUAUACUAAGGCUCCG UUCC  SEQ ID NO 52

CGACCGAAAAAGACCUGAAUUCUAUACUAAGUCUACG UUAC  SEQ ID NO 53

GGACCGUAAAGACCUGAUUUCUAUACUAAGUCUACGU UCC  SEQ ID NO 54

GGACCGUAAAGACCUGAUUCUAUACUAAGUCUACGUU CC  SEQ ID NO 55

GGACCCGAAAAAGACCUGAGUUCUAUACUAAGUCUAC GUUCC  SEQ ID NO 56

GGACCGAACAAGCCCUGACUUCUAUACUAAGGCUACG UGCC  SEQ ID NO 57

GGACCGGAAAGACCUGAUUUCUAUACUAAGUCUACGU UAC  SEQ ID NO 58

GGACCCGAAAAAGACCUGACUUCUAUACUAAGUCUAC GUACC  SEQ ID NO 59

GGACCGAAAAACACCUGAAUUCUAUACUAAGUGUACG UUCC  SEQ ID NO 60

GGACCGAACAAGACCUGACUUCUGUACUAAGACUACG UUGC  SEQ ID NO 61

GGACCGUAAAGACCUGAUUUCUAUACUAAGUCUACGU UAC  SEQ ID NO 62

GGACCGAAAAACACCUGACUUCUAUACUAAGGCUACG UAUG  SEQ ID NO 63

GGACCGAAUAAGGCCUGACUUCUAUACUAAGCCUGCG UUCC  SEQ ID NO 64

GGACCGUAAAGGCCUGACUUCUAUACUAAGCCUACGU UCC  SEQ ID NO 65

GGACCGAAUAAGACCUGAGUUCUGUACUAAGUCUCCG UUCC  SEQ ID NO 66

GGACCCAAAAAGGCCUGACUUCUAUACUAAGCCUAUG UUCC  SEQ ID NO 67

GUACCGGAAAGGCCCUGACUUCUAUACUAAGGCUACG UUGC  SEQ ID NO 68

CGACCGAAAAAGGCCUGACUUCUAUACUAAGCCUACG UACC  SEQ ID NO 69

GGACCGUAAAGACCUGAUUCUAUACUAAGUCUACGUA CC  SEQ ID NO 70

GGACCCGAAAAAGACCUGAGUUCUAUACUAAGUCUCC GUUCC  SEQ ID NO 71

GUACCGAGGAAGACCUGACUUCUGUACUAAGUCUACG UUAC  SEQ ID NO 72

GUACCGGAAAGGCCCUGACUUCUAUACUAAGGCCACG UUGC  SEQ ID NO 73

GGACCUGUAAAGACCUGAAUUCUAUACUAAGUCUACA UGCC  SEQ ID NO 74

GAACCGAAGAAAGACCUGAACUUCUAUACUAAGGCUA CGUUUG  SEQ ID NO 75

GGACCGUAAAGACCGGAUUCUAUACUAAGUCUACGUU AC  SEQ ID NO 76

Example 2D

Engineered Mutations in the Minimized A9 Aptamer ARC591

Mutations relative to the original ARC591 sequence were observed at several sites in the reselected clones with a frequency higher than expected based on the nucleotide proportions used in the doped pool synthesis. Several point mutants were constructed and tested based on these mutations to see whether their prevalence in the reselected clones was due to their ability to confer a selective binding advantage.

For the point mutant constructs described below, the purines comprise a 2'-OH and the pyrimidines comprise a 2'-fluoro modification, while, the templates and primers comprise unmodified deoxyribonucleotides.

For the point mutant aptamer SEQ ID NO 77) 5'-GGAG-GACCCGAAAAAGACCUGACUUCUAUAC-UAAGUCUACGUUCCUC-3', the 5' PCR primer SEQ ID NO 91) 5'-CCGTACGAGAGTGCGTAA-3' and 3' PCR primer (SEQ ID NO 92) 5'-GGAGGAACGTAGACTTAG-3' were used to amplify template (SEQ ID NO 93) 5'-CGTAC-GAGAGTGCGTAATACGACTCACTATAG-GAGGACCCGAAAAAGACCTGACTT CTATAC-TAAGTCTACGTTCCTCC-3'.

For the point mutant aptamer SEQ ID NO 78) 5'-GGAG-GACCGGAAAAGACCUGACUUCUAUAC-UAAGUCUACGUUCCUCC-3', the 5' PCR primer (SEQ ID NO 94) 5'-CCGTACGAGAGTGCGTAA-3' and 3' PCR primer (SEQ ID NO 95) 5'-GGAGGAACGTAGACTTAG-3' were used to amplify template (SEQ ID NO 96) 5'-CCGTAC-GAGAGTGCGTAATACGACTCACTATAG-GAGGACCGGAAAAGACCTGACTT CTATACTAAGTC-TACGTTCCTCC-3'.

For the point mutant aptamer (SEQ ID NO 79) 5'-GGAG-GACCGAACAAGACCUGACUUCUAUAC-UAAGUCUACGUUCCUCC-3', the 5' PCR primer (SEQ ID NO 97) 5'-CCGTACGAGAGTGCGTAA-3' and 3' PCR primer (SEQ ID NO 98) 5'-GGAGGAACGTAGACTTAG-3' were used to amplify template SEQ ID NO 99) 5'-CCGTAC-GAGAGTGCGTAATACGACTCACTATAG-GAGGACCGAACAAGACCTGACTT CTATACTAAGTC-TACGTTCCTCC-3'.

For the point mutant aptamer (SEQ ID NO 80) 5'-GGAG-GACCGAAAAGGACCUGACUUCUAUAC-UAAGUCCACGUUCCUCC-3', the 5' PCR primer (SEQ ID NO 100) 5'-CCGTACGAGAGTGCGTAA-3' and 3' PCR primer (SEQ ID NO 101) 5'-GGAGGAACGTGGACTTAG-3' were used to amplify template (SEQ ID NO 102) 5'-CCG-TACGAGAGTGCGTAATACGACTCACTAT-AGGAGGACCGAAAAGGACCTGACTT CTATACTAAGTCCACGTTCCTCC-3'.

For the point mutant aptamer (SEQ ID NO 81) 5'-GGAG-GACCGAAAAACACCUGACUUCUAUAC-UAAGUGUACGUUCCUCC-3', the 5' PCR primer (SEQ ID NO 103) 5'-CCGTACGAGAGTGCGTAA-3', and 3' PCR primer (SEQ ID NO 104) 5'-GGAGGAACGTAGCCTTAG-3' were used to amplify template (SEQ ID NO 105) 5'-CCG-TACGAGAGTGCGTAATACGACTCACTAT-AGGAGGACCGAAAAACACCTGACTT CTATACTAAGTGTACGTTCCTCC-3'.

For the point mutant aptamer (SEQ ID NO 82) 5'-GGAG-GACCGAAAAAGCCCUGACUUCUAUAC-UAAGGCUACGUUCCUCC-3', the 5' PCR primer (SEQ ID NO 106) 5'-CCGTACGAGAGTGCGTAA-3', and 3' PCR primer (SEQ ID NO 107) 5'-GGAGGAACGTAGCCTTAG-3' were used to amplify template (SEQ ID NO 108) 5'-CCG-TACGAGAGTGCGTAATACGACTCACTAT-AGGAGGACCGAAAAAGCCCTGACTT CTATACTAAGGCTACGTTCCTCC-3'.

For the point mutant aptamer (SEQ ID NO 83) 5'-GGAG-GACCGAAAAAGGCCUGACUUCUAUAC-UAAGCCUACGUUCCUCC-3', the 5' PCR primer (SEQ ID NO 109) 5'-CCGTACGAGAGTGCGTAA-3', and 3' PCR primer (SEQ ID NO 110) 5'-GGAGGAACGTAGGCTTAG-3' were used to amplify template (SEQ ID NO 111) 5'-CCG-TACGAGAGTGCGTAATACGACTCACTAT-AGGAGGACCGAAAAAGGCCTGACTT CTATACTAAGCCTACGTTCCTCC-3'.

For the point mutant aptamer (SEQ ID NO 84) 5'-GGAG-GACCGAAAAAGACCUGACUUCUGUAC-UAAGUCUACGUUCCUCC-3', the 5' PCR primer (SEQ ID NO 112) 5'-CCGTACGAGAGTGCGTAA-3' and 3' PCR primer j (SEQ ID NO 113) 5'-GGAGGAACGTAGACTTAG-3' were used to amplify template (SEQ ID NO 114) 5'-CCG-TACGAGAGTGCGTAATACGACTCACTAT-AGGAGGACCGAAAAAGACCTGACTT CTGTACTAAGTCTACGTTCCTCC-3'.

For the point mutant aptamer (SEQ ID NO 85) 5'-GGAG-GACCGAAAAAGACCUGACUUCUAUAC-UAAGUCUACGUACCUCC-3', the 5' PCR primer (SEQ ID NO 115) 5'-CCGTACGAGAGTGCGTAA-3' and 3' PCR primer (SEQ ID NO 116) 5'-GGAGGTACGTAGACTTAG-3' were used to amplify template (SEQ ID NO 117) 5'-CCG-TACGAGAGTGCGTAATACGACTCACTAT-AGGAGGACCGAAAAAGACCTGACTT CTATAC-TAAGTCTACGTACCTCC-3'.

For the point mutant aptamer (SEQ ID NO 86) 5'-GGAG-GACCGAAAAAGACCUGACUUCUAUAC-UAAGUCUACGUUACUCC-3', the 5' PCR primer (SEQ ID NO 118) 5'-CCGTACGAGAGTGCGTAA-3' and 3' PCR primer (SEQ ID NO 119) 5'-GGAGTAACGTAGACTTAG-3' were used to amplify template (SEQ ID NO 120) 5'-CCG-TACGAGAGTGCGTAATACGACTCACTAT-AGGAGGACCGAAAAAGACCTGACTT CTATAC-TAAGTCTACGTTACTCC-3'.

These point mutant constructs were assessed for activity in terms of inhibition of PSMA NAALADase activity. The NAALADase assay was performed in 96 well format. PSMA aptamers were serially diluted in 1× reaction buffer (40 mM Tris-HCl, pH 7.4, 0.1 mM ZnSO$_4$, 0.1 mg/mL BSA) in a standard 96 well plate to be tested at a final concentration range from 30 pM to 1 µM. The enzyme was prepared by diluting 30 µL of 100 nM PSMA into 8 mL of reaction buffer, and kept cool on ice. The substrate was prepared by adding 19 µl of NAAG [Glutamate-3,4-$^3$H], 50.8 Ci/mmol, 19.7 µM (Perkin-Elmer, Wellesley, Mass., NET1082) into 2.2 mL of reaction buffer.

Following preparation of all reagents, 4 µl of each serially diluted aptamer was added to a separate 96 well plate (the reaction plate). 76 µl of diluted enzyme was added to the corresponding wells containing aptamer. 80 µl of reaction buffer was added to one column of wells to serve as a background control. The diluted substrate and reaction plate were then moved to a room at 37° C. and allowed to equilibrate for 10 minutes. After temperature equilibration, 20 µl of the prepared substrate was added to each well using a 12 channel pipet for a final volume of 100 µl/well, and a final concentration of 0.3 nM enzyme and 30 nM substrate per well. A column of wells containing enzyme and substrate only was used as a high control. The aptamer/enzyme/substrate reaction was incubated at 37° C. for 15 minutes, and stopped by the addition of 100 µl of quench buffer (100 mM sodium phosphate, pH 7.4, 2 mM EDTA).

To separate the cleavage products, NAAG and Glutamate, from the substrate, an AG 1-×8, 200-400 mesh, formate resin (BioRad, Hercules, Calif., # 140-1454) was used. The resin was prepared by forming a 1:1 slurry in H$_2$O, and adding 140 µl per 96 well using a Multiscreen filter plate (Multiscreen, 1.2 µm filter plates (Millipore, Billerica, Mass., # MABVN1250)). The filter plate was centrifuged at 2000 rpm for 2 minutes to pack the resin (forming a 70 µl resin bed) and for subsequent elutions. 100 µl of reaction was added to the resin columns, centrifuged, and the flow through was collected and discarded using a standard 96 well plate as a catch plate, assembled with the filter plate by using a Multiscreen centrifuge alignment frame (Millipore, # MACF09604). The columns were washed with 2×50 µl of H$_2$O, and the flow through was collected in the catch plate and discarded. The columns were then washed with 3×50 µl of 1 M Formate, pH 1.8. For each wash with Formate the eluent was collected and saved in the catch plate. Subsequently, 50 µl of the collected eluent was transferred to a Deepwell Luma plate (Perkin Elmer, Wellesley, Mass.) and dried thoroughly using a speed vac centrifuge for 1 hr on medium heat. The plate was sealed and read using a Packard Topcount Microplate Scintillation Counter. A table comparing the positional mutations for each point mutant construct made, and the respective IC$_{50}$'s for each in the NAALADase assay is shown in FIG. 10.

Through these experiments, three base changes relative to the original sequence were identified that marginally improved the apparent affinity of the aptamer for PSMA. Replacement of position A12 in the A-rich bulge with C (observed in 13% of reselected clones) improved the NAALADase IC$_{50}$ by approximately 20%. Similar improvement was observed when the covarying A16:U35 base pair was replaced by a G:C pairing. A composite molecule with all three of these mutations was generated, known as ARC1113 (SEQ ID NO 88).

Surprisingly a number of statistically favored mutations had either no or negative effects on NAALADase inhibition activity. It is possible that the mutations are uniquely favored in the context of the doped pool (i.e. where the aptamer is flanked by long primer sequences that might impact the proper folding of the functional domain). Alternatively, the mutations may impact binding properties to favor enrichment selection without changing its intrinsic affinity for PSMA (e.g. by slowing the kinetics of association/dissociation).

Table 9 lists the sequences for all the point mutant constructs generated. All sequences are listed in the 5' to 3' direction, and unless otherwise indicated all purines are 2'-OH and the pyrimidines comprise a 2'-fluoro modification. In some embodiments, the invention comprises aptamers with a nucleic acid sequences as described in Table 9 below. In some embodiments, the nucleic acid sequences of the aptamers described in Table 9 below additionally comprise a 3' cap (e.g., an inverted dT cap), and/or 5' amine (NH$_2$) modification to facilitate chemical coupling, and/or conjugation to a high molecular weight, non-immunogenic compound (e.g., PEG). In other embodiments, the nucleic acid sequences described in Table 9 lack the indicated 3' cap (e.g., an inverted dT cap (3T)) and/or 5' amine (NH$_2$) modification to facilitate chemical coupling.

Lower case letters "m" and "f" preceding A, C, G, or U in ARC834 (SEQ ID NO 87), ARC1113 (SEQ ID NO 88), ARC2035 (SEQ ID NO 89) and ARC2036 (SEQ ID NO 90) denote 2'-O-methyl and 2'-fluoro substitutions respectively.

TABLE 9

Sequences of point mutant constructs

GGAGGACCCGAAAAAGACCUGACUUCUAUACUAAGUC SEQ ID NO 77
UACGUUCCUCC,

GGAGGACCGGAAAAGACCUGACUUCUAUACUAAGUCU SEQ ID NO 78
ACGUUCCUCC

GGAGGACCGAACAAGACCUGACUUCUAUACUAAGUCU SEQ ID NO 79
ACGUUCCUCC

GGAGGACCGAAAAGGACCUGACUUCUAUACUAAGUCC SEQ ID NO 80
ACGUUCCUCC

GGAGGACCGAAAAACACCUGACUUCUAUACUAAGUGU SEQ ID NO 81
ACGUUCCUCC

GGAGGACCGAAAAAGCCCUGACUUCUAUACUAAGGCU SEQ ID NO 82
ACGUUCCUCC

GGAGGACCGAAAAAGGCCUGACUUCUAUACUAAGCCU SEQ ID NO 83
ACGUUCCUCC

GGAGGACCGAAAAAGACCUGACUUCUGUACUAAGUCU SEQ ID NO 84
ACGUUCCUCC

GGAGGACCGAAAAAGACCUGACUUCUAUACUAAGUCU SEQ ID NO 85
ACGUACCUCC

GGAGGACCGAAAAAGACCUGACUUCUAUACUAAGUCU SEQ ID NO 86
ACGUUACUCC

ARC834
mGmGmmGmGmAGAAAAAGAGAfCfCfUGAfCfUfUfC SEQ ID NO 87
fUAfUAfCfUAAGfUfCfUAfCGfUmUmCmCmUmCmC
A

TABLE 9-continued

Sequences of point mutant constructs

ARC 1113
NH2-mCmGmGmAfCfCmGAACAmAmGmGmCfCfUGAf SEQ ID NO 88
CfUfUfCfUAfUAfCfUAAmGmCmCmUAfCmGfUmUm
CmCmG-3T

ARC2035
NH2-mCmGmGmAmGAAfCAmAmGmGmCfCfUGAfCfU SEQ ID NO 89
fUfCfUAfUAfCfUAAmGmCmCmUAfCmGfUmUmCmC
mGU

ARC2036
mCmGmGmAfCfCmGAAfCAmAmGmGmCfCfUGAfCfU SEQ ID NO 90
fUfCfUAfUAfCfUAAmGmCmCmUAfCmGfUmUmCmC
mG-3T

Example 2E

Engineered Backbone Modifications in the A9 Aptamer

To improve stability and manufacturability, constructs containing 2'-O-methyl modifications at individual and blocks of positions of ARC591 were chemically synthesized and evaluated for their impact on aptamer inhibition of NAALADase activity, in the assay previously described. A table comparing the positional block substitutions for the various constructs generated (ARC834-ARC839), and ARC941-ARC944) is shown in FIG. 11, along with the respective IC$_{50}$'s for each in the NAALADase assay. The sequences for these constructs are listed in Table 10 below. In summary, the vast majority of both ribo- and 2'-fluoronucleotides in the helical stems could be replaced with 2'-O-methyl nucleotides without compromising functional activity, measured using the NAALADase inhibition assay previously described.

Additionally, through three phases of optimization of ARC1113 (ARC591 with 3 base modifications as described above), it was further discovered that a significant fraction of nucleotides in the conserved hairpin loop and A-rich bulge can be replaced with 2'-O-methyl, 2'-deoxy-, or 2'-deoxy phosphorothioate modifications. In Phase 1 optimization of ARC1113, block 2'-O-methyl modifications that were found to be well tolerated from the optimization of ARC591 were combined with additional single 2'-O-methyl modifications to ARC1113, to yield ARC1508-ARC1517. In Phase 2, the additional 2'-O-methyl modifications that were well tolerated from Phase 1 were combined with 2'-deoxy modifications, to yield ARC1574-ARC1586.

In Phase 3 optimization, the 2'-O-methyl, 2'-deoxy modifications from the first two phases were combined with 2'-deoxy phosphorothioate modifications to yield ARC1721-ARC1722. From this third phase of optimization, an aptamer was identified, ARC1725, which retained full activity as assessed in the NAALADase inhibition assay relative to the unmodified ARC591. A table comparing the positional backbone modifications for each construct generated during all three phases of optimization and the corresponding IC$_{50}$'s for each in the NAALADase assay are summarized in FIG. 11. The sequences for these constructs are listed in Table 10 below.

Plasma stability of each construct was measured using a plasma stability time course assay over 0, 1, 3, 10, 30, and 100 hours. A reaction was set up for each aptamer tested in an eppendorf tube using 95% human plasma (20 μl per time point), an appropriate concentration of aptamer (determined by the highest predicted dosing level ($C_{Max}$)), and a sufficient amount of spiked 5'-end labeled aptamer such that a 1:10 dilution of the reaction will be over 1000 cpm, brought to total volume with 1×PBS. When assembling the reaction, the plasma was added last, and the reactions were immediately added to a 37° C. heat block. A reaction for each aptamer tested containing 1×PBS instead of plasma was used as a 0 hour time point. At each designated time point, 20 µl was withdrawn from each reaction and added to an appropriately labeled eppendorf tube containing 200 µl of formamide loading dye, and was immediately snap frozen in liquid nitrogen and stored at −20° C. After all the samples were collected, 20 µl of each plasma sample/loading dye was aliquoted into separate tubes, and 2 µl of 1% SDS was added to each tube (final SDS concentration 0.1%). The samples containing 0.1% SDS were heated at 90° C. for 10-15 minutes. Subsequently, 15 µl of each of the heated samples were loaded on a 15% PAGE gel, leaving an empty lane in between each aptamers' time course. The PAGE gel was run at 12 W for 35 minutes in order to keep all of the labeled material on the gel. When the gel was finished running, it was exposed to a phosphor-imaging screen and scanned on a Storm860 phosphorimaging machine (Molecular Dynamics, Sunnyvale, Calif.).

The percentage of the parent aptamer remaining for each time-point was determined by quantifying the parent aptamer band and dividing by the total counts in the lane. This value was normalized each time-point to the percentage parent aptamer of the 0 hour time-point. The normalized percentage values were graphed as a measure of time, and the data was fit to the following equation: m1*e^(−m2*m0); where m1 is the maximum % parent aptamer (m1=100); and m2 is the rate of degradation. The half life of the aptamer ($T_{1/2}$) is equal to the (ln 2)/m2.

The modifications from Phase 1 through Phase 3 were combined to yield ARC1725. ARC1113 is a ribo-containing aptamer based on ARC 591 with fully-stabilized helical stems and a 3'-cap (3'-idT). ARC1725 is a ribo-free version based on ARC591, in which ribos have been systematically replaced by DNA, 2'-O-Me, and a phosphorothioate. Surprisingly the fully-ribo free molecule does not have significantly improved stability relative to the parent ARC1113 in this assay (11 hrs. vs. 20 hrs.).

Table 10 lists the sequences for all the optimized constructs generated. Unless otherwise indicated, the nucleic acid sequences listed in Table 10 are in the 5' to 3' direction, and all nucleotides are 2'-OH, except where lower case letters "m" and "f", preceding A, C, G, or U, refer to 2'-O-methyl and 2'-fluoro modified nucleotides respectively. In some embodiments, the invention comprises aptamers with a nucleic acid sequences as described in Table 10 below. In some embodiments, the nucleic acid sequences of the aptamers described in Table 10 below additionally comprise a 3' cap (e.g., an inverted dT cap (3T)), and/or 5' amine (NH$_2$) modification to facilitate chemical coupling, and/or conjugation to a high molecular weight, non-immunogenic compound (e.g., PEG). In other embodiments, the nucleic acid sequences described in Table 10 lack the indicated 3' cap (e.g., an inverted dT cap) and/or 5' amine (NH$_2$) modification to facilitate chemical coupling.

TABLE 10

Optimized sequences from backbone modifications to ARC591 and ARC1113

ARC834
mGmGmAmGmAfCfCfGAAAAAGAfCfCfUGAfCfUf UfCfUAfUAfCfUAAGfUfCfUAfCfGfUmUmCmCmUm CmCA SEQ ID NO 87

TABLE 10-continued

Optimized sequences from backbone modifications to ARC591 and ARC1113

ARC835
mGmGmAmGmACGAAAAAGAfCfCfUGAfCfUfUfC fUAfUAfCfUAAGfUfCfUAfCGfUfUfCfCfUfCfC A SEQ ID NO 122

ARC836
GGAGGAfCfCmGAAAAAGAfCfCfUGAfCfUfUfCfU AfUAfCfUAAGfUfCfUAfCmGfUfUfCfCfUfCfCA SEQ ID NO 123

ARC837
GGAGGAfCfCGAAAAmAmGmAfCfCfUGAfCfUfUfC fUAfUAfCfUAAmGfUfCfUAfCGfUfUfCfCfUfCf CA SEQ ID NO 124

ARC838
GGAGGAfCmCmGAAAAAGAfCfCfUGAfCfUfUfCfU AfUAfCfUAAGfUfCfUAmCmGfUfUfCfCfUfCfCA SEQ ID NO 125

ARC839
GGAGGAfCfCGAAAAmAmGmAmCfCfUGAfCfUfUfC fUAfUAfCfUAAmGmUmCmUAfCGfUfUfCfCfUfCf CA SEQ ID NO 126

ARC941
mGmGmAmGmAfCfCmGAAAAmAmGmAmCfCfUGAf CfUfCfUAfUAfCfUAAmGmUmCmUAfCmGfUmUmC mCmUmCmC-3T SEQ ID NO 127

ARC942
mCmGmGmAmGAAAAmAmGmAmCfCfUGAfCfUfUfCf UAfUAfCfUAAmGmUmCmUAfCmGfUmUmCmCmG-3T SEQ ID NO 128

ARC2037
NH2-mCmGmGmAfCfCmGAAAAmAmGmAmCfCfUGAf CfUfUfCfUAfUAfCfUAAmGmUmCmUAfCmGfUmUm CmCmG-3T SEQ ID NO 129

ARC1026
mCmGmGmAfCfCmGAAAAmAmGmAmCfCfUGAfCfUf UfCfUAfUAfCfUAAmGmUmCmUAfCmGfUmUmCmCm GU SEQ ID NO 130

ARC943
mCmGmGmAfCfCmGmAmGmAmCfCfUGAfCfUfUfCf UAfUAfCfUAAmGmUmCmUfCmGmGmUmCmG-3T SEQ ID NO 131

ARC944
XmCmGmGmAfCfCmGAAAAmAmGmAmCfCfUGAfCfU fUfCfUAfUAfCfUAAmGmUmCmUAfCmGfUmUmCmC mG-3T SEQ ID NO 132 where X = 5'-fluorescein

ARC1508
mCmGmGmAfCfCmGmAAfCAmAmGmGmCfCfUGAfCf UfUfCfUAfUAfCfUAAmGmCmCmUAfCmGfUmUmCm CmG-3T SEQ ID NO 133

ARC1509
mCmGmGmAfCfCmGAmAfCAmAmGmGmCfCfUGAfCf UfUfCfUAfUAfCfUAAmGmCmCmUAfCmGfUmUmCm CmG-3T SEQ ID NO 134

ARC1510
mCmGmGmAfCfCmGAAfCmAmAmGmGmCfCfUGAfCf UfUfCfUAfUAfCfUAAmGmCmCmUAfCmGfUmUmCm CmG-3T SEQ ID NO 135

ARC1511
mCmGmGmAfCfCmGAAfCAmAmGmGmCfCfUmGAfCf UfUfCfUAfUAfCfUAAmGmCmCmUAfCmGfUmUmCm CmG-3T SEQ ID NO 136

TABLE 10-continued

Optimized sequences from backbone modifications to ARC591 and ARC1113

ARC1512
mCmGmGmAfCfCmGAAfCAmAmGmGmCfCfUGmAfCf   SEQ ID NO 137
UfUfCfUAfUAfCfUAAmGmCmCmUAfCmGfUmUmCm
CmG-3T

ARC1513
mCmGmGmAfCfCmGAAfCAmAmGmGmCfCfUGAfCfU   SEQ ID NO 138
fUfCfUmAFuAfCfUAAmGmCmCmUAfCmGfUmUmCm
CmG-3T

ARC1514
mCmGmGmACmGAAfCAmAmGmGmCfCfUGAfCfUfUf   SEQ ID NO 139
CfUAfUmAfCfUAAmGmCmCmUAfCmGfUmUmCmCm
G-3T

ARC1515
mCmGmGmAfCfCmGAAfCAmAmGmGmCfCfUGAfCfU   SEQ ID NO 140
fUfCfUAfUAfCfUmAAmGmCmCmUAfCmGfUmUmCm
CmG-3T

ARC1516
mCGmGmAfCfCmGAAfCAmAmGmGmCfCfUGAfCfUf   SEQ ID NO 141
UfCfUAfUAfCfUAmAmGmCmCmAFfCmGfUmUmCm
mG-3T

ARC1517
mCmGmGmAmGAAfCAmAmGmGmCfCfUGAfCfUfUfC   SEQ ID NO 142
fUAfUAfCfUAAmGmCmCmUAfCmGfUmUmCmCmG-
3T

ARC1574
mCmGmGmAfCfCmGAAfCmAmAmGmGmCfCfUGAfCf   SEQ ID NO 143
UfUfCfUAfUAfCfUAAmGmCmCmUAfCmGfUmUmC
mCmG-3T

ARC1575
mCmGmGmAfCfCmGAAfCAmAmGmGmCfCfUGmAfCf   SEQ ID NO 144
CfUmAfUAfCfUAAmGmCmCmUAfCmGfUmUmCmCm
mG-3T

ARC1576
mCmGmGmAfCfCmGAAfCmAmAmGmGmCfCfUGmAfC   SEQ ID NO 145
fUfCfCfUmAfUmAfCfUAmAmGmCmCmUAfCmGfU
mUmCmCmG-3

ARC1577
mCmGmGmACmGdAAtCAmAmGmGmCfCfUGAfCfUfU   SEQ ID NO 146
fCfUAfUAfCfUAAmGmCmCmUAfCmGfUmUmCmCm
G-3T

ARC1578
mCmGmGmAfCfCmGAdAfCAmAmGmGmCfCfUGAfCf   SEQ ID NO 147
UfUfCfUAfUAfCfUAAmGmCmCmUAfCmGfUmUmCm
CmG-3T

ARC1579
mCmGmGmACmGAAfCAmAmGmGmCfCfUdGAfCfUfU   SEQ ID NO 148
fUAfUAfCfUAAmGmCmCmUAfCmGfUmUmCmCmG-3
T

ARC1580
mCmGmGmAfCfCmGAAfCAmAmGmGmCfCfUGAfCfU   SEQ ID NO 149
fCfCfUAUfAfCfUdAAmGmCmCmUAfCmGfUmUmCm
CmG-3T

ARC1581
mCmGmGmACmGdAdAfCmAmAmGmGmCfCfUdGAfCfUfU   SEQ ID NO 150
fCfUAfUAfCfUdAAmGmCmCmUAfCmGfUmUmCmGm
G-3T

ARC1582
mCmGmGmAfCCmGdAACmAmAmGmGmCfCfGmAfCfU   SEQ ID NO 151
fUfCfUmAfUmAfCfUAmAmGmCmCmCmUAfCmGfUm
mCmCmG-3T

ARC1583
mCmGmGmAfCfCmGAdAfCmAmAmGmGmCfCfUGmAf   SEQ ID NO 152
CfUfCfUmAfUmAfCfuAmAmGmCmCmUmAfCmGf
UmUmCmCmG-3T

ARC1584
mCmGmGmAfCfCmGAAfCmAmAmGmGmCfCfUdGmAf   SEQ ID NO 153
CfUUfCfUmAfUmAfCfUAmAmGmCmCmUmAfCmGfm
UmCmCmG-3T

ARC1585
mCmGmGmAfCfCmGAAfCmAmAmGmGmCfCUGmAfCf   SEQ ID NO 154
UfUfCfUmAfUmAfCfUdAmAmGmCmCmUmAfCmGfU
mUmCmCmG-3T

ARC1586
mCmGmGmAmGdAdAfCfmAmAmGmGmCfCfUdGmAfC   SEQ ID NO 155
fUfUfCfUmAfUmAfCfUdAmAmGmCmCmUmAfCmGf
UmUmCmCmG-3T

ARC1721
mCmGmGmAfCfCmGAAfCAmAmGmGmCfCfUGAfCf   SEQ ID NO 156
UfUfCfUAfUAfCfUAmAmGmCmCmUmAfCmGfUmU
mCmCmG-3T

ARC2033
NH2-mCmGmGmAfCfCmGAAfCAmAmGmGmCfCfUGA   SEQ ID NO 157
fCfUfUfCfUmAfUAfCfUAmAmGmCmCmUmAfCmGf
UmUmCmCmG

ARC2034
NH2-mCmGmGmAfCfCmGAAfCAAfCAmAmGmGmCf   SEQ ID NO 158
CfUGAfCfUfUfCfUmAfUAfCfUAAmGmCmCmUmA
fCmGfUmUmCmCmG-3T

ARC1722
mCmGmGmAfCfCmGdAAfCAmAmGmGmCfCfUGAfCf   SEQ ID NO 159
uFuFcfUmAfUAfCfUAAmGmCmCmUmAfCmGfUmU
mCmCmG-3T

ARC1723
mCmGmGmAfCfCmGdAAfCAmAmGmGmCfCfUGmAf   SEQ ID NO 160
CfUfUfCfUmAfUAfCfUdAmAmGmCmCmUmAfCmG
fUmUmCmCmG-3T

ARC1724
mCmGmGmACmGdAdAfCmAmAmGmGmCfCfUGmAfCf   SEQ ID NO 161
UfUfCfUmAfUmAfCfUdAmAmGmCmCmUmAfCmGfU
mUmCmCmG-3T

ARC1725
mCmGmGmACmGdAdAfCmAmAmGmGmCfCfU-s-dGm   SEQ ID NO 162
AfCfUfUfCfUmAfUmAfCfUdAmAmGmCmCmUmAtC
mGtUmUmCmCmG-3T

ARC2032
NH2-mCmGmGmAfCfCmGdAdAfCmAmAmGmGmCfCf   SEQ ID NO 163
U-s-dGmAfCfUfUfCfUmAfUmAfCfUdAmAmGmCm
CmUmAfCmGfUmUmCmCmGU

ARC1726
mCmGmGmAfCfCmGdA-s-dAfCmAmAmGmGmCfCfU   SEQ ID NO 164
GmAfCfUfUfCfUmAfUmAfCfUdAmAmGmCmCmUmA
fCmGfUmUmCmCmG-3T

ARC1727
mCmGmGmAfCfCmGdA-s-dAfCmAmAmGmGmCfCf   SEQ ID NO 165
U-s-dGmAfCfUfUfCfUmAfUmAfCfUdAmAmGmCm
CmUmAfCmGfUmUmCmCmG-3T

Example 3

Aptamer-Toxin Conjugates

Example 3A

Synthesis of Aptamer-Conjugatable Small Molecule Toxins

Aptamers to PSMA were modified with activated, high potency cytotoxics to enable targeted killing of PSMA-expressing tumor cells (described in Example 4). Initial work focused on conjugation of vinblastine hydrazide to the 3'-end of ribonucleotide-terminated aptamers. Subsequent experiments focused on attachment of DM1, an activated maytansinoid, to aptamers via 5'-amines introduced during solid phase synthesis.

Materials and Methods. To facilitate testing of aptamer-cytotoxin conjugates, conjugatable forms of vinblastine (vinblastine hydrazide) and maytansine (DM1-SPP) were prepared from commercially available precursors. Chemicals were purchased from Honeywell Burdick & Jackson (Morristown, N.J.) and used from the supplier without further purification. Small molecules were analyzed by $^1$H NMR at 400 MHz in an appropriate deuterated solvent. Small molecules were purified where appropriate on a Biotage Horizon system (Charlottesville, Va.) with normal phase silica. Reactions were either monitored by TLC or RP-HPLC (100 mM TEAA buffer A, acetonitrile buffer B) or SAX-HPLC (25 mM phosphate, 25% acetonitrile buffer A and B, 1 M NaCl buffer B). For all RP-HPLC TSKgel OligoDNA-RP columns were used. (Tosoh Biosciences, South San Francisco, Calif.). Synthesized aptamers were analyzed using SAX-HPLC columns: DNA-PAC100 (Dionex, Sunnyvale, Calif.), and purified on Resource columns (ABI Applied Biosystems, Foster City, Calif.).

Figure 12:
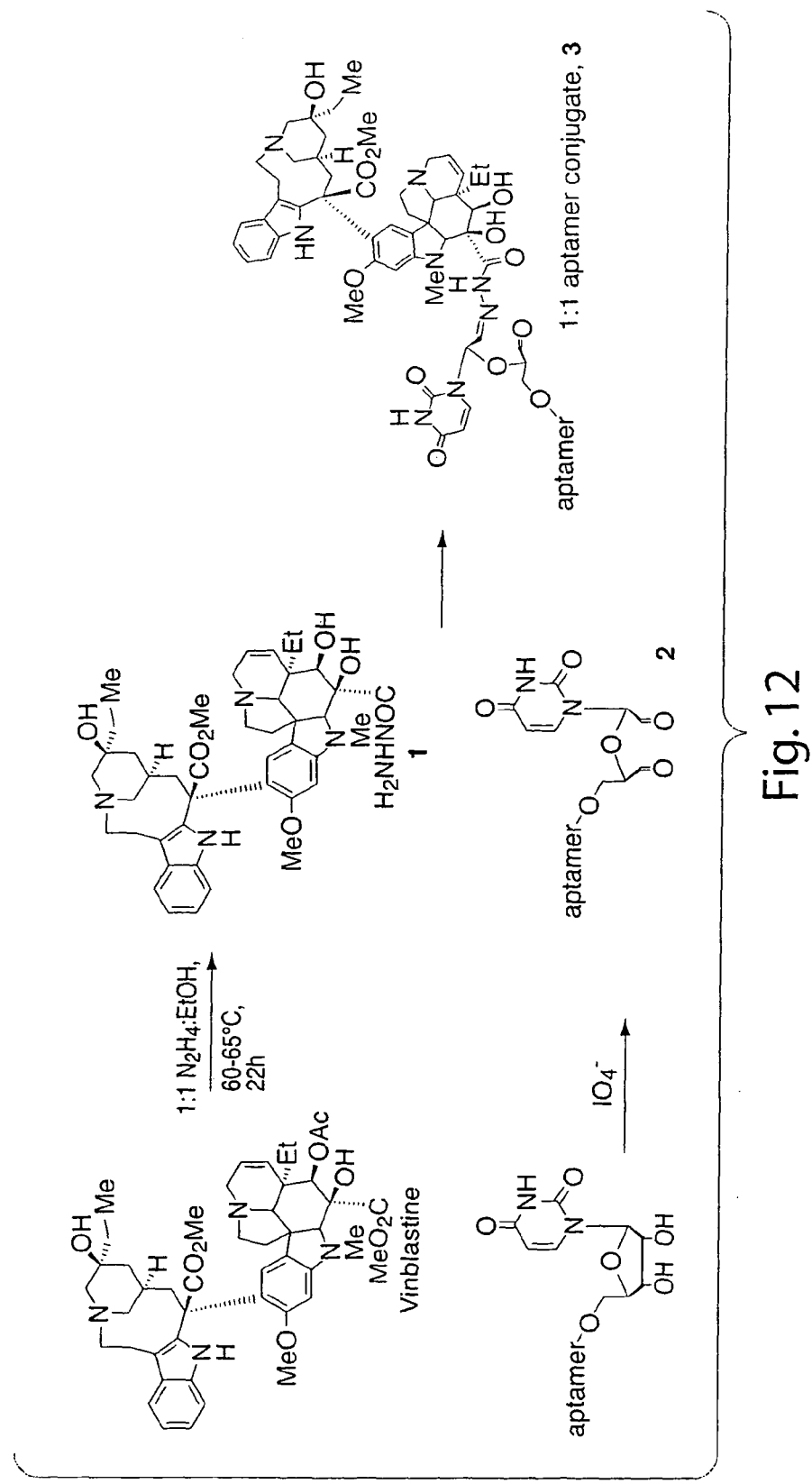
FIG. 12 is an illustration of the chemical synthesis of vinblastine-aptamer conjugates.

Preparation of vinblastine hydrazide. Vinblastine hydrazide was prepared according to the method of Brady et al. *J. Med. Chem.* 2002, 45, 4706-4715, as depicted schematically in FIG. 12, except the product was purified on a short chromatography column in 1:1 ethyl acetate:methanol.

Briefly, vinblastine sulfate (100 mg, 0.1 mmol) (Acros Organics, Morris Plains, N.J.) was suspended in 1:1 hydrazine:ethanol (4 mL) and heated to 65° C. in a sealed flask for 22 hours. Thin layer chromatography ("TLC") indicated the starting material was completely consumed. The reaction mixture was then cooled in ice and diluted with dichloromethane ("DCM"). The solution was then diluted with water and the layers were separated. The organic layer was washed with water, saturated sodium carbonate and brine. The organic layer was evaporated and then azeotroped with 2:1 toluene:ethanol. The crude product was flashed on a short silica column eluting with 1:1 ethyl acetate:methanol to yield compound 1 (FIG. 18), 0.073 grams (87%).

Preparation of DM1. DM1 was prepared as depicted schematically in FIG. 13. Briefly, maytansinol was prepared according the method of Kupchan et al. *J. Med. Chem.* 1978, 21, 31-37. Maytansinol was then coupled to carboxylic acid 3. Disulfide reduction and re-oxidation with 4-(2 pyridyldithio)pentanoate ("SPP") was then conducted to yield DM1.

Figure 13:
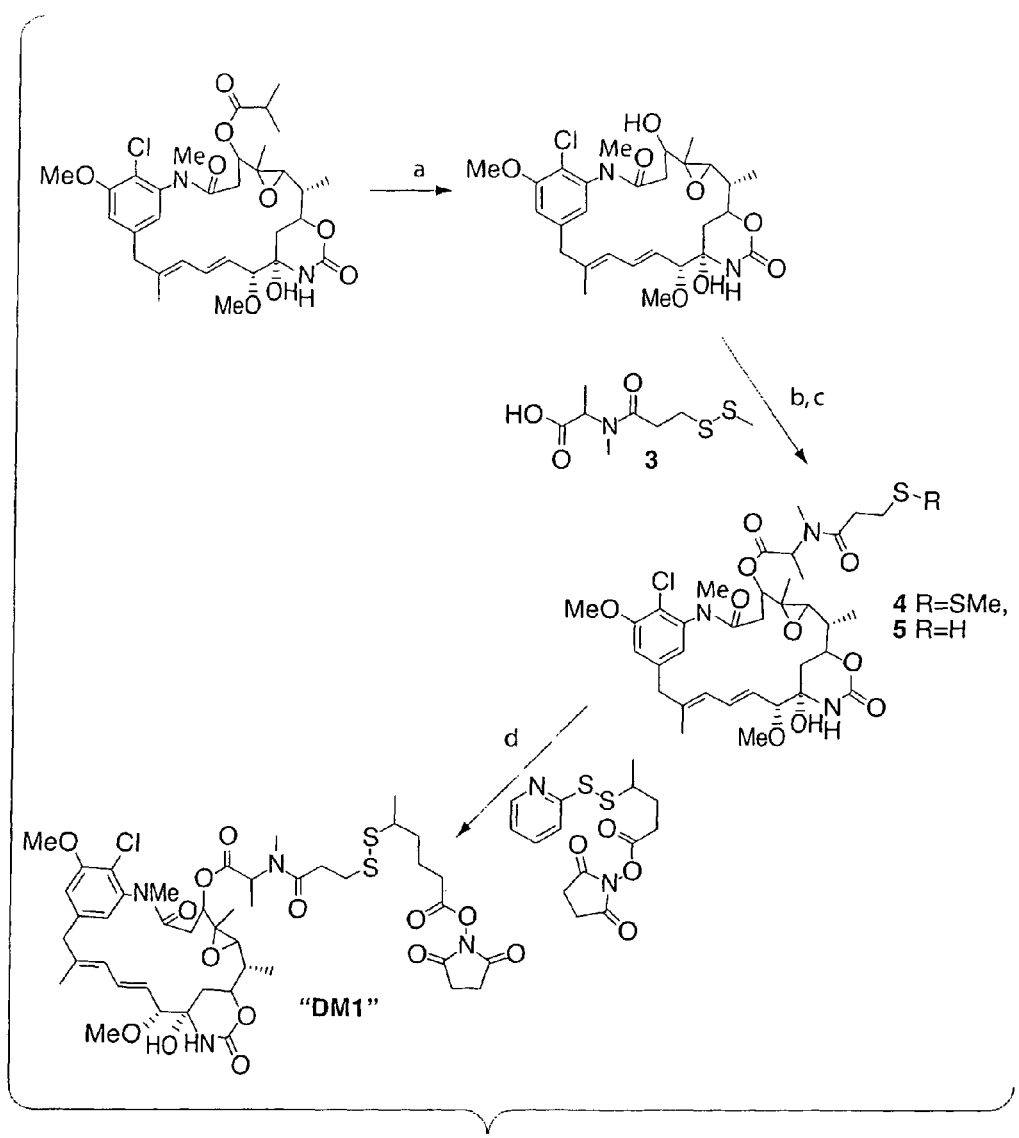
FIG. 13 is an illustration of the chemical synthesis of activated maytansinoid suitable for aptamer conjugation.

For step "a" of the synthesis depicted in FIG. 13, six 5 mg portions of ansamitocin P3 (Sigma, St. Louis, Mo.) were combined and azeotroped with toluene three times. Ansamitocin P3 was then dissolved in THF and cooled to 0° C. in ice. Lithium aluminum hydride ("LAH") was added in portions while the reaction was monitored by TLC. A total of 2-3 mg of LAH was added over 3 hours at which point the reaction was quenched with 1% sulfuric acid. The reaction mixture was diluted with ethyl acetate and transferred to a separatory funnel and the layers separated. The organic layer was washed with water and brine and concentrated to a white solid, which was purified in DCM by column chromatography to give another white solid, maytansinol, 20 mg (65%).

For step "b" of the synthesis depicted in FIG. 13, maytansinol (20 mg) was diluted with DCM (0.5 mL) and acid 3 (prepared as described below and in FIG. 21) was added in 0.5 mL of DCM. To the homogenous mixture was added dicyclohexy-carbo-diimide ("DCC") and 25 µL of 1 M ZnCl$_2$ in ether. The reaction mixture, now heterogeneous, was stirred under argon overnight. The reaction mixture was diluted with DCM and water (1 mL each) and transferred to a separatory funnel. The layers were separated and the organic layer dried over MgSO$_4$ and concentrated to yellow film which was used without further manipulation to yield compound 4.

For step "c" of the synthesis depicted in FIG. 13, compound 4, was dissolved in 1:1 ethyl acetate:methanol and treated with a 10-fold excess of dithiothreitol ("DTT"). After 1 hour the reaction mixture was quenched with water and extracted with ethyl acetate. Evaporation gave a yellow solid which was again used without further purification, 0.027 g (60%) over three steps to yield compound 5.

For step "d" of the synthesis depicted in FIG. 13, compound 5, was treated with SPP (prepared as described below and in FIG. 14) (3 eq.) in N,N-dimethylformamide and methanol (0.5 mL each) for 3 hours at room temperature. Concentration and purification on a small silica pad gave DM1 0.035 g (77%) yield.

Figure 14:
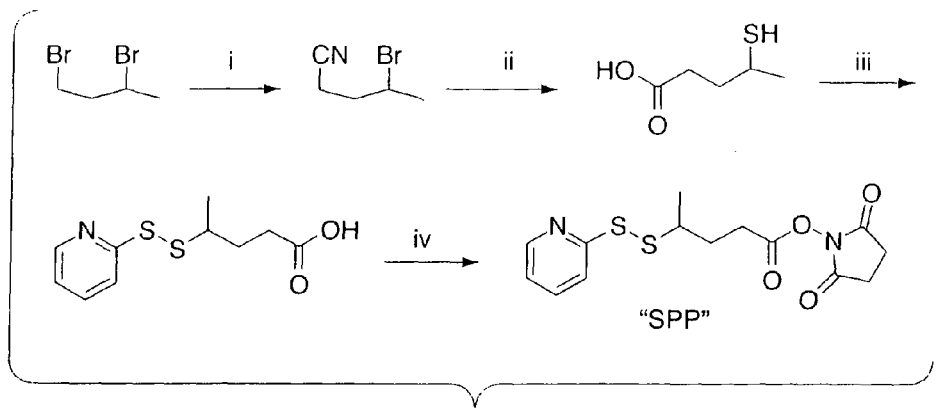
FIG. 14 is an illustration of the synthesis of SPP, a component in the activated maytansinoid linker arm.

Preparation of SPP. SPP which was used in the DM1 synthesis described above and in FIG. 13, was synthesized according to Carlsson et al. Biochem. J. 1978, 173, 723-737, as illustrated in FIG. 14. Briefly, 1,3-Dibromobutane (15 g, 0.069 mol) was dissolved in DMSO. NaCN (3.75 g, 0.076 mol) was dissolved in 8 mL of water and 1 mL was added immediately. The rest of the cyanide solution was added over 0.5 hour. The reaction mixture was then stirred overnight. The reaction mixture was diluted with 70 mL of water and the aqueous mixture extracted with 2×125 mL of 1:1 heptane:ethyl acetate. The combined organic layers were then washed with 70 mL water, and 70 mL of brine. The organic layer was concentrated and dissolved in 21 mL of ethanol. Thiourea (6.64 g, 0.087 mol) was added along with 21 mL of water and the homogenous reaction mixture was heated to reflux for 4 hours. At this point 50 mL of 10M NaOH solution was added and the reaction mixture heated to reflux overnight. The reaction mixture was cooled to room temperature and diluted with 50 mL EtOAc. The EtOAc was separated and the organic layer washed with another portion of EtOAc. The combined organic layers were combined and concentrated to yield a slightly yellow liquid (6.48 g, 70%). 2,2'-Dithiopyridine (25 g) was dissolved in ethanol (100 mL) and acetic acid (4.2 mL). The thiol-acid was added over 15 minutes and the reaction stirred for 2 hours at room temperature. The reaction was concentrated to yield a solution that was purified on a Biotage 40M cartridge eluting with 3:1 toluene:EtOAc to 1:3 toluene:EtOAc to give a while solid, SPP, 13 g (79%).

Figure 15:
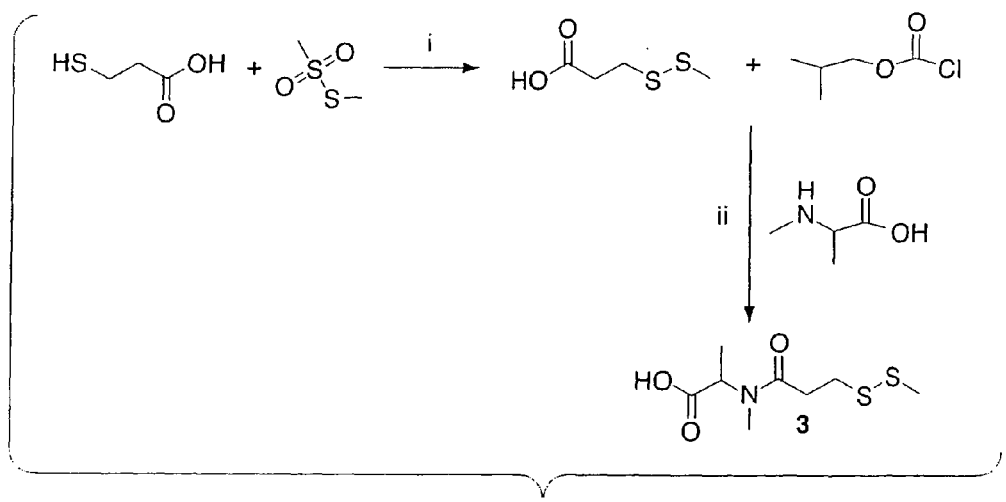
FIG. 15 is an illustration of the synthesis of carboxylic acid 3, a component in the activated maytansinoid arm.

Preparation of Carboxylic acid 3. Carboxylic acid 3 used in the DM1 synthesis described above and in FIG. 13, was synthesized as shown in FIG. 15. Briefly, 3-Mercaptoproapnoic acid (5 g, 0.047 mol) was dissolved in water (150 mL) and methyl methanethiosulfonate (6.54 g, 0.052 mol) was added in ethanol (75 mL). The homogeneous reaction mixture was stirred overnight. The reaction mixture was then diluted with 400 mL of brine and extracted with 2×200 mL of EtOAc. The combined organic layers were washed with 150 mL of brine and then concentrated to yield the acid, which was carried on without further manipulation.

The acid (2 g, 0.013 mol) was dissolved in THF (40 mL). TEA (1.8 mL) was added and the solution cooled to −15° C. under argon. Isobutylchloroformate (1.65 mL, 0.013 mol) was added in 2 portions and the reaction mixture stirred for 15 minutes at −15° C. N-methyl-DL-analine (1.34 g, 0.013 g) was added in 3.6 mL of TEA and 20 mL of water. The reaction mixture, which was heterogeneous, was allowed to warm to room temperature over 1 hour and stirred overnight. The reaction was diluted with 50 mL of water and acidified to pH 6 with 1 M HCl. The solution was extracted with 125 mL of EtOAc and concentrated to yield the acid 3, FIG. 15, 0.61 g (20%).

Preparation of aptamers. All aptamers were synthesized via solid phase chemistry on an AKTA DNA synthesizer (GE Healthcare Biosciences, Piscataway, N.J.) according to standard protocols using commercially available phosphoramidites (Glen Research, Sterling, Va. or ChemGenes Corp., Wilmington, Mass.) and an inverted deoxythymidine CPG support or a ribo guanosine CPG support (Agrawal, S. Ed. *Protocols for Oligonucleotides and Analogs* Humana Press: Totowa, N.J. 1993). Where indicated, terminal amine function (denoted "NH2") was attached with a 5'-amino-modifier, 6-(Trifluoroacetylamino)hexyl-(2-cyanoethyl)-(N,N-diisopropyl)-phosphoramidite, C6-TFA (Glen Research, Sterling, Va. or ChemGenes Corp., Wilmington, Mass.). After deprotection, all aptamers were HPLC purified and ethanol precipitated before use. Aptamer toxin conjugates were successfully made using the following aptamers (all depicted in 5' to 3' direction), where lower case letters "m", "f", and "d" denote 2'-O-methyl, 2'-fluoro, and 2'-deoxy substitutions respectively and all other nucleotides are 2'-OH; 3T denotes an inverted 3' deoxy thymidine; and 5'-amine ($NH_2$) facilitates chemical coupling to toxins.

```
ARC725 (irrelevant control)
mCmUmAmCmUmAmCmAmCmAmUGGGmUmCGGGmUGmA  SEQ ID NO 166
GmUGGmCmAmAmAGGmAmAmUmAGmUmAG
```

-continued

```
ARC964
dCTdCdATdCdGdGdCdAdGdAdCdGdAdCTdCdGdC  SEQ ID NO 167
dCdCdGdAU

ARC1026
mCmGmGmAmAfCfCmGAAAAmAmGmAmCfCfUGAfCf  SEQ ID No 130
UfUfCfUAfUAfCfUAAmGmUmCmUAfCmGfUmUmCm
CmGU

ARC1113
NH2-mCmGmGmAmGAAfCAmmGmGmCfCfUGAfCfUf  SEQ ID NO 88
UfCfUAfUAfUAfCfUAAmGmCmCmUAfCmGfUmUmC
mCmG-3T

ARC1142
NH2-mAGmAGGmAGmAGmAmAmCGmUmUmCmUmAmCm  SEQ ID NO 18
UmAmUGGGmUGGmCmUGGGmAGGGG
```

Preparation of vinblastine conjugates. Aptamer containing a 3'-terminal ribose residue (such as ARC1026, 85 nmole) was oxidized with 50 equivalents of $NaIO_4$ in water, 250 μL, for 1.5 hours in the dark to give compound 2, FIG. 12. After the aging period, the reaction mixture was passed through a C18 column (Waters Corporation, Milford, Mass.) or a G25 column (GE Biosciences, Piscataway, N.J.) and 1.5 equivalents of vinblastine hydrazide were added. The reaction was incubated for 4 hours and then passed through a Centricolumn (Princeton Separations, Princeton, N.J.) to yield 52 nmoles of the ARC1026 vinblastine hydrazide conjugate, compound 3 FIG. 12. Conjugates were used in cell killing assays without further manipulation.

The resulting vinblastine aptamer conjugates comprise the following structure:

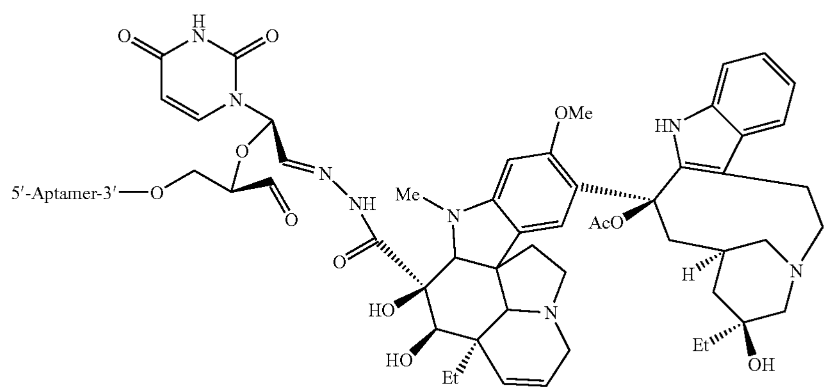

Preparation of DM1 conjugates. Cytotoxic conjugates of 5'-amine terminated aptamers with DM1 were synthesized according to the following method: ARC1113, for example, was mixed with DM1 in phosphate buffer (50 mM sodium phosphate, 100 mM NaCl, pH 7.21) and acetonitrile. The reaction was monitored by HPLC and excess DM1 was typically added (2-4 equivalents). The reaction was allowed to proceed until the aptamer concentration was <10% of the starting concentration, and remaining unconjugated toxin was removed by Centricolumn or G25 column. Yield varied from 70-90% based on the aptamer.

The resulting DM1 conjugates comprise the following structure:

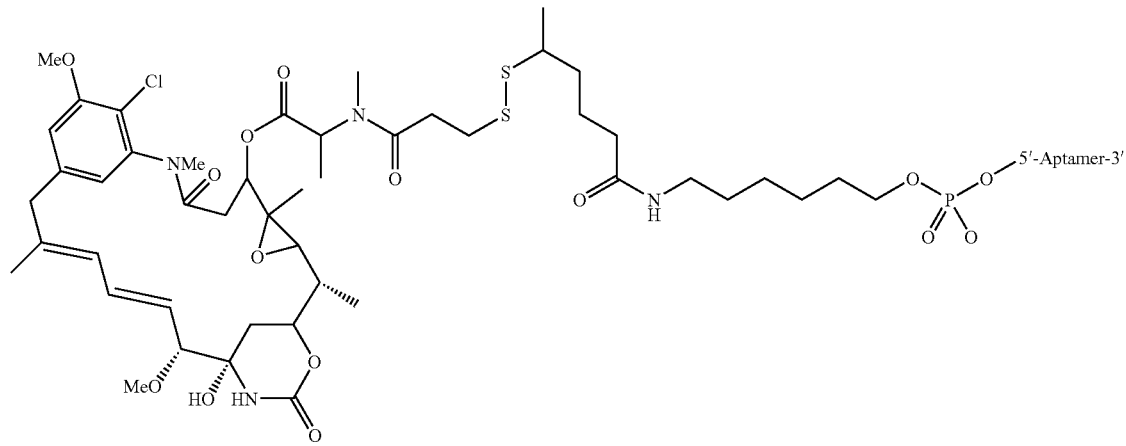

Example 3B

Alternative Aptamer-Toxin Conjugates

In addition to mediating the targeted delivery of small molecule cytotoxic agents to tumor cells, alternative conjugation methods allow the attachment of a variety of other toxic payloads that can similarly induce tumor cell killing. Potential alternatives include radioisotopes, protein toxins, and encapsulated cytotoxics.

Several different radioisotopes, including yttrium-90, indium-111, iodine-131, lutetium-177, copper-67, rhenium-186, rhenium-188, bismuth-212, bismuth-213, astatine-211, and actinium-225, can be used to bring about targeted killing of tumor cells. These isotopes may be conjugated to aptamers in a variety of different ways, depending upon the chemical properties of the specific radiometal. For example, iodine-131 may be covalently incorporated to a carrier molecule which, with subsequent activation, can be attached to the 5'-amine on an aptamer. Appropriate carrier molecules for iodination include (p-iodophenyl)ethylamine and N-succinimidyl-3-(4-hydroxyphenyl)propionate (Bolton-Hunter reagent) (Kurth et al., J Med Chem. 36:1255).

Alternatively, many other radiometals including $^{90}$Y and $^{111}$Ind may be bound to a chelator that is covalently attached to the aptamer. Appropriate chelators include conjugateable forms of diethylenetriaminepentaacetate (DTPA), 1,4,7,10-tetraazacyclododecane-1,4,7,10-tetraacetic acid (DOTA), Mercaptoacetylglycine (MAG3), and hydrazinonicotinamide (HYNIC). Attachment may be afforded by preparing amine-reactive forms of these chelators (e.g. DTPA-ITC, the isothiocyanate form of DTPA) and combining them with 5'-amine-modified aptamers under appropriate reaction conditions.

Protein toxins typically exhibit remarkably high potency, in some cases requiring as little as a single molecule to kill a target cell. Many of these toxins are composed as bipartite molecules with separable domains responsible for targeting/cellular uptake and for cell killing. By isolating the entity responsible for cell killing and effectively substituting the targeting/uptake functionality by an aptamer, potent tumor-specific cytotoxic agents may be generated. Toxins appropriate for conjugation to tumor cell-specific aptamers include diphtheria toxin, ricin, abrin, gelonin, and Pseudomonas exotoxin A. Protein toxins may be conjugated via free lysines to 5'-amine modified aptamers using homobifunctional amine-reactive cross-linking agents such as DSS (Disuccinimidyl suberate), DSG (Disuccinimidyl glutarate), or BS$^3$ (Bis[sulfosuccinimidyl]suberate). Alternatively, cysteine-bearing toxins may be conjugated to amine-bearing aptamers using heterobifunctional cross-linking agents such as SMPT (4-Succinimidyloxycarbonyl-methyl-a-[2-pyridyldithio] toluene) or SPDP (N-succinimidyl-3-(2-pyridyldithio)propionate).

Conventional cytotoxic agents may be effectively encapsulated in nanoparticle forms such as liposomes, dendrimers, or comb polymers to favorably alter their biodistribution and pharmacokinetic properties, favoring lowered toxicities and increased retention in tumors. The addition of targeting agents such as aptamers highly specific for tumor antigens makes it possible to further optimize the delivery of these cytotoxic nanoparticles. Methods for coating the surface of liposomes with aptamers have been previously described and include the covalent attachment of lipophilic moieties to the 5'-terminus of an aptamer (e.g. diacylglycerols). Similarly, polymeric nanoparticles composed of PEG and PLGA may be modified to allow attachment of aptamers through 3'-end modification as described previously (Fahrokzahd et al., Cancer Research (2004) 64:7668-7672).

Example 3C

Radiolabeled Anti-PSMA Aptamers as Diagnostic Agents

In addition to its therapeutic applications, appropriately modified anti-PSMA aptamers can be used as diagnostic agents to detect, stage, and manage the treatment of prostate cancer. Conjugation of aptamers to metal chelating agents as described previously enables labeling with gamma-emitting radioisotopes such as $^{99}$Tc and $^{111}$In. Labeled aptamers administered to a patient localize in a target-specific way to sites of PSMA expression including primary and metastatic tumors. UnPEGylated aptamers are rapidly cleared via renal elimination unless they are sequestered through specific target binding. As such, a large tumor:blood ratio develops quickly, making it possible to image a patient within a matter of hours following administration of the imaging agent. Localized radiometal can be directly imaged using a gamma camera to quantify uptake into tumors. Successive imaging over an extended period makes it possible to monitor disease progression and to guide treatment options.

Example 4

Functional Cell Assays

PSMA aptamer-vinblastine conjugates prepared as described in Example 3 above were tested in vitro for PSMA targeted killing of LNCaP cells. Effects on LNCaP cell viability were assessed in a cell proliferation assay based on chemiluminescent detection of BrdU described below (Cell Proliferation ELISA, BrdU (Roche, Indianapolis, Ind.). PC-3 cells were used as a control cell line.

Methods. LNCaP and PC-3 cells (ATCC, Manassas, Va.) were cultured in RPMI-1640 (ATCC) supplemented with 10% FBS (Gibco, Carlsbad, Calif.). Media from LNCaP (PSMA+) or PC3 (PSMA−) cells growing in 15 cm plates was aspirated off then cells were washed with 10 mL 1×PBS. Cells were trypsinized for 30 sec at 37° C. Following trypsinization, 8 mL 10% FBS media was used to quench trypsin. Cells were spun at 1000 rpm for 3.30 min. Following spin the media was aspirated off and the cell pellet was re-suspended with 10 mL complete media. The cell density was adjusted to 200,000 cells/mL. 50 µl of cells/well was added to collagen coated black 96-well plates (10,000 cells/well). Cells were incubated at 37° C. in 5% $CO_2$ for 24 hrs to allow adequate adherence. Following overnight incubation 25 µl of media, aptamer or antibody was added to each well with the final volume in the well being 100 µl and incubated at 37° C. in 5% $CO_2$ for designated time length. Following incubation cells were washed three times with complete media and further incubated at 37° C. in 5% $CO_2$ for 48 hrs. After 2 days 20 µl BrdU labeling reagent (100×) is mixed with 2 mL of complete media. 10 µl of BrdU labeling reagent mixture was added to each well, and the cells were incubated with BrdU at 37° C. in 5% $CO_2$ for 2.5 hrs. After incubation, the media was removed, and the assay was completed following the manufacturer's protocol: 200 µl/well FixDenat solution was added to each well and incubated for 30 min at RT. Following removal of FixDenat solution 100 µl anti-BrdU POD Fab fragment solution (Luminol/4-iodophenol) was added to each well and incubated for 90 min at RT. After incubation anti-BrdU POD solution was removed and plates were washed with 200 µl/well of washing solution three times with 5 min RT incubations. 100 µl of substrate solution was added to each well and cells were incubated for 3 min at RT in the dark. The plates were read using a luminescence program with a 1 sec count on a Packard TopCount Microplate Scintillation and Luminescence Counter.

Genistein (Wako Chemicals, Richmond, Va.) was used as a positive control for the cytotoxicity assays and consistently showed partial inhibition at 25 µM doses and complete cell killing at 150 µM.

Figure 16:
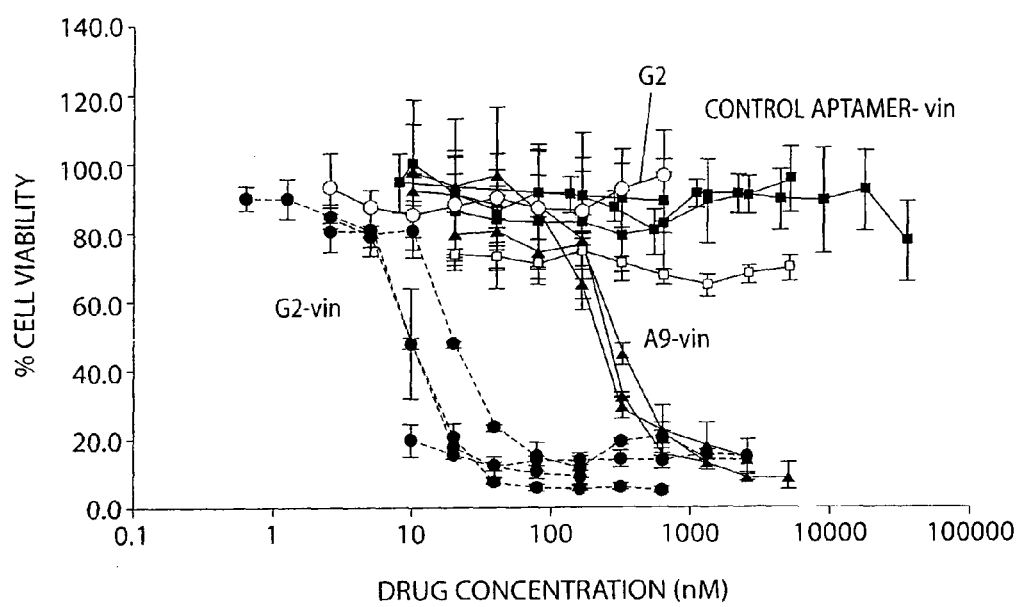
FIG. 16 is a graph illustrating the cytotoxic effect of PSMA aptamers conjugated to vinblastine, versus non-toxin conjugated PSMA aptamers. G2-vin (filled circles) refers to the vinblastine conjugate of ARC1142 (a 5'-amine labeled form of ARC1091, a minimized ARC955 (G2) aptamer). A9-vin (filled triangles) refers to the vinblastine conjugate of ARC1026 (a modified form of ARC942 (minimized A9 aptamer)). G2 (ARC955) (open circles) and A9 (ARC942)

FIG. 16 shows % cell viability of LNCaP cells treated with the vinblastine conjugate of ARC1142 (referred to as G2-vin in the figure), the vinblastine conjugate of ARC1026 (referred to as A9-vin in the figure,) the negative control vinblastine conjugate of ARC725 (referred to as control aptamer-vin in the figure), ARC955 (referred to as G2 in the figure) or ARC942 (referred to as A9 in the figure.) Functional, non-toxin conjugated aptamers specific for PSMA, ARC955 and ARC942, were shown in this assay to have no intrinsic effect on cell viability at any concentration. A vinblastine conjugate of an arbitrary oligonucleotide sequence (ARC725) with a nucleotide composition similar to ARC1142 but no intrinsic PSMA binding similarly failed to show cell killing over the entire concentration range. Vinblastine conjugates of both functional PSMA aptamers, ARC1142 and ARC1026, on the other hand, were able to induce complete cell killing at moderate to low concentrations (10-500 nM) with the ARC955 (G2) derivative showing approximately 30-fold better potency than the ARC942 (A9) derivative. Vinblastine conjugates of both functional PSMA aptamers, ARC1142 and ARC1026, had little to no cytotoxic effect on cell viability of non-PSMA expressing PC-3 cells (data not shown).

The invention having now been described by way of written description and example, those of skill in the art will recognize that the invention can be practiced in a variety of embodiments and that the description and examples above are for purposes of illustration and not limitation of the following claims.

---

What is claimed is:

1. An aptamer that binds to PSMA, comprising a nucleic acid sequence that is at least 90% identical to the full length of a nucleic acid sequence selected from the group consisting of SEQ ID NO's 11-13 and 15-19.

2. The aptamer of claim 1, wherein the aptamer binds to PSMA with a dissociation constant of 1 μM or less.

3. The aptamer of claim 1, wherein the aptamer is further modified to comprise at least one chemical modification.

4. The aptamer of claim 3, wherein the at least one modification is selected from the group consisting: of a chemical substitution at a sugar position; a chemical substitution at a phosphate position; and a chemical substitution at a base position of the nucleic acid.

5. The aptamer of claim 3, wherein the at least one modification is selected from the group consisting of: incorporation of a modified nucleotide, 3' capping, conjugation to an amine linker, conjugation to a high molecular weight, non-immunogenic compound, conjugation to a lipophilic compound, conjugation to a drug, conjugation to a cytotoxic moiety and labeling with a radioisotope.

6. The aptamer of claim 3, wherein the at least one modification is conjugation to a cytotoxic moiety and the cytotoxic moiety is conjugated to the 5' end of the aptamer.

7. The aptamer of claim 3, wherein the at least one modification is conjugation to a cytotoxic moiety and the cytotoxic moiety is conjugated to the 3' end of the aptamer.

8. The aptamer of claim 3, wherein the at least one modification is conjugation to a cytotoxic moiety and the cytotoxic moiety is encapsulated in a nanoparticle.

9. The aptamer of claim 3, wherein the cytotoxic moiety is conjugated to the aptamer by a moiety selected from the group consisting of: liposomes, dendrimers, and comb polymers.

10. The aptamer of claim 3, wherein the at least one modification is conjugation to a cytotoxic moiety and the cytotoxic moiety is a small molecule cytotoxic agent.

11. The aptamer of claim 10, wherein the small molecule cytotoxic moiety is selected from the group consisting of: vinblastine hydrazide, calicheamicin, vinca alkaloid, a cryptophycin, a tubulysin, dolastatin-10, dolastatin-15, auristatin E, rhizoxin, epothilone B, epithilone D, taxoid, maytansinoid, and any variants and derivatives thereof.

12. The aptamer of claim 3, wherein the at least one modification is conjugation to a radioisotope and the radioisotope is selected from the group consisting of: yttrium-90, indium-111, iodine-131, lutetium-177, copper-67, rhenium-186, rhenium-188, bismuth-212, bismuth-213, astatine-211, and actinium-225.

13. The aptamer of claim 3, wherein the at least one modification is conjugation to a cytotoxic moiety and the cytotoxic moiety is a protein toxin.

14. The aptamer of claim 13, wherein the protein toxin is selected from the group consisting of: diphtheria toxin, ricin, abrin, gelonin, and Pseudomonas exotoxin A.

15. The aptamer of claim 10 wherein the small molecule cytotoxic agent is vinblastine.

16. The aptamer of claim 15, wherein the vinblastine is conjugated to the 3' end of the aptamer.

17. The aptamer of claim 3, wherein the at least one modification is conjugation to a polyethylene glycol.

18. A pharmaceutical composition comprising a therapeutically effective amount of the aptamer of claim 10 or a salt thereof, and a pharmaceutically acceptable carrier or diluent.

* * * * *

SEQUENCE LISTING

```
<160> NUMBER OF SEQ ID NOS: 168

<210> SEQ ID NO 1
<211> LENGTH: 93
<212> TYPE: DNA
<213> ORGANISM: artificial sequence
<220> FEATURE:
<223> OTHER INFORMATION: synthetic template
<220> FEATURE:
<221> NAME/KEY: misc_feature
<222> LOCATION: (25)..(54)
<223> OTHER INFORMATION: N is a, t, c, or g

<400> SEQUENCE: 1
catcgatgct agtcgtaacg atccnnnnnn nnnnnnnnnn nnnnnnnnnn nnncgagaa      60 cgttctctcc tctccctata gtgagtcgta tta                                  93

<210> SEQ ID NO 2
<211> LENGTH: 92
<212> TYPE: DNA
<213> ORGANISM: artificial sequence
```

-continued

```
<220> FEATURE:
<223> OTHER INFORMATION: synthetic template
<220> FEATURE:
<221> NAME/KEY: misc_feature
<222> LOCATION: (24)..(53)
<223> OTHER INFORMATION: n is a, t, c, or g

<400> SEQUENCE: 2
catgcatcgc gactgactag ccgnnnnnnn nnnnnnnnnn nnnnnnnnnn nnngtagaac    60
gttctctcct ctccctatag tgagtcgtat ta                                 92

<210> SEQ ID NO 3
<211> LENGTH: 92
<212> TYPE: DNA
<213> ORGANISM: artificial sequence
<220> FEATURE:
<223> OTHER INFORMATION: synthetic template
<220> FEATURE:
<221> NAME/KEY: misc_feature
<222> LOCATION: (24)..(53)
<223> OTHER INFORMATION: n is a, t, c, or g

<400> SEQUENCE: 3
catcgatcga tcgatcgaca gcgnnnnnnn nnnnnnnnnn nnnnnnnnnn nnngtagaac    60
gttctctcct ctccctatag tgagtcgtat ta                                 92

<210> SEQ ID NO 4
<211> LENGTH: 10
<212> TYPE: DNA
<213> ORGANISM: artificial sequence
<220> FEATURE:
<223> OTHER INFORMATION: synthetic CpG sequence

<400> SEQUENCE: 4
aacgttcgag                                                          10

<210> SEQ ID NO 5
<211> LENGTH: 728
<212> TYPE: PRT
<213> ORGANISM: homo sapiens

<400> SEQUENCE: 5
```

Asp Ala Ala Gln Pro Ala Arg Arg Ala Arg Arg Thr Lys Leu His His
1               5                   10                  15

His His His His His His Ser Ser Asn Glu Ala Thr Asn Ile Thr Pro
            20                  25                  30

Lys His Asn Met Lys Ala Phe Leu Asp Glu Leu Lys Ala Glu Asn Ile
        35                  40                  45

Lys Lys Phe Leu Tyr Asn Phe Thr Gln Ile Pro His Leu Ala Gly Thr
    50                  55                  60

Glu Gln Asn Phe Gln Leu Ala Lys Gln Ile Gln Ser Gln Trp Lys Glu
65                  70                  75                  80

Phe Gly Leu Asp Ser Val Glu Leu Ala His Tyr Asp Val Leu Leu Ser
                85                  90                  95

Tyr Pro Asn Lys Thr His Pro Asn Tyr Ile Ser Ile Ile Asn Glu Asp
            100                 105                 110

Gly Asn Glu Ile Phe Asn Thr Ser Leu Phe Glu Pro Pro Pro Pro Gly
        115                 120                 125

Tyr Glu Asn Val Ser Asp Ile Val Pro Pro Phe Ser Ala Phe Ser Pro
    130                 135                 140

Gln Gly Met Pro Glu Gly Asp Leu Val Tyr Val Asn Tyr Ala Arg Thr

-continued

```
              145                 150                 155                 160
        Glu Asp Phe Phe Lys Leu Glu Arg Asp Met Lys Ile Asn Cys Ser Gly
                        165                 170                 175
        Lys Ile Val Ile Ala Arg Tyr Gly Lys Val Phe Arg Gly Asn Lys Val
                        180                 185                 190
        Lys Asn Ala Gln Leu Ala Gly Ala Lys Gly Val Ile Leu Tyr Ser Asp
                        195                 200                 205
        Pro Ala Asp Tyr Phe Ala Pro Gly Val Lys Ser Tyr Pro Asp Gly Trp
                        210                 215                 220
        Asn Leu Pro Gly Gly Val Gln Arg Gly Asn Ile Leu Asn Leu Asn
        225                 230                 235                 240
        Gly Ala Gly Asp Pro Leu Thr Pro Gly Tyr Pro Ala Asn Glu Tyr Ala
                        245                 250                 255
        Tyr Arg Arg Gly Ile Ala Glu Ala Val Gly Leu Pro Ser Ile Pro Val
                        260                 265                 270
        His Pro Ile Gly Tyr Tyr Asp Ala Gln Lys Leu Leu Glu Lys Met Gly
                        275                 280                 285
        Gly Ser Ala Pro Pro Asp Ser Ser Trp Arg Gly Ser Leu Lys Val Pro
                        290                 295                 300
        Tyr Asn Val Gly Pro Gly Phe Thr Gly Asn Phe Ser Thr Gln Lys Val
        305                 310                 315                 320
        Lys Met His Ile His Ser Thr Asn Glu Val Thr Arg Ile Tyr Asn Val
                        325                 330                 335
        Ile Gly Thr Leu Arg Gly Ala Val Glu Pro Arg Tyr Val Ile Leu
                        340                 345                 350
        Gly Gly His Arg Asp Ser Trp Val Phe Gly Gly Ile Asp Pro Gln Ser
                        355                 360                 365
        Gly Ala Ala Val Val His Glu Ile Val Arg Ser Phe Gly Thr Leu Lys
                        370                 375                 380
        Lys Glu Gly Trp Arg Pro Arg Arg Thr Ile Leu Phe Ala Ser Trp Asp
        385                 390                 395                 400
        Ala Glu Glu Phe Gly Leu Leu Gly Ser Thr Glu Trp Ala Glu Glu Asn
                        405                 410                 415
        Ser Arg Leu Leu Gln Glu Arg Gly Val Ala Tyr Ile Asn Ala Asp Ser
                        420                 425                 430
        Ser Ile Glu Gly Asn Tyr Thr Leu Arg Val Asp Cys Thr Pro Leu Met
                        435                 440                 445
        Tyr Ser Leu Val His Asn Leu Thr Lys Glu Leu Lys Ser Pro Asp Glu
                        450                 455                 460
        Gly Phe Glu Gly Lys Ser Leu Tyr Glu Ser Trp Thr Lys Lys Ser Pro
        465                 470                 475                 480
        Ser Pro Glu Phe Ser Gly Met Pro Arg Ile Ser Lys Leu Gly Ser Gly
                        485                 490                 495
        Asn Asp Phe Glu Val Phe Phe Gln Arg Leu Gly Ile Ala Ser Gly Arg
                        500                 505                 510
        Ala Arg Tyr Thr Lys Asn Trp Glu Thr Asn Lys Phe Ser Gly Tyr Pro
                        515                 520                 525
        Leu Tyr His Ser Val Tyr Glu Thr Tyr Glu Leu Val Glu Lys Phe Tyr
                        530                 535                 540
        Asp Pro Met Phe Lys Tyr His Leu Thr Val Ala Gln Val Arg Gly Gly
        545                 550                 555                 560
        Met Val Phe Glu Leu Ala Asn Ser Ile Val Leu Pro Phe Asp Cys Arg
                        565                 570                 575
```

```
Asp Tyr Ala Val Val Leu Arg Lys Tyr Ala Asp Lys Ile Tyr Ser Ile
            580                 585                 590

Ser Met Lys His Pro Gln Glu Met Lys Thr Tyr Ser Val Ser Phe Asp
        595                 600                 605

Ser Leu Phe Ser Ala Val Lys Asn Phe Thr Glu Ile Ala Ser Lys Phe
    610                 615                 620

Ser Glu Arg Leu Gln Asp Phe Asp Lys Ser Asn Pro Ile Val Leu Arg
625                 630                 635                 640

Met Met Asn Asp Gln Leu Met Phe Leu Glu Arg Ala Phe Ile Asp Pro
                645                 650                 655

Leu Gly Leu Pro Asp Arg Pro Phe Tyr Arg His Val Ile Tyr Ala Pro
            660                 665                 670

Ser Ser His Asn Lys Tyr Ala Gly Glu Ser Phe Pro Gly Ile Tyr Asp
        675                 680                 685

Ala Leu Phe Asp Ile Glu Ser Lys Val Asp Pro Ser Lys Ala Trp Gly
    690                 695                 700

Glu Val Lys Arg Gln Ile Tyr Val Ala Ala Phe Thr Val Gln Ala Ala
705                 710                 715                 720

Ala Glu Thr Leu Ser Glu Val Ala
                725

<210> SEQ ID NO 6
<211> LENGTH: 92
<212> TYPE: DNA
<213> ORGANISM: artificial sequence
<220> FEATURE:
<223> OTHER INFORMATION: synthetic template
<220> FEATURE:
<221> NAME/KEY: misc_feature
<222> LOCATION: (40)..(69)
<223> OTHER INFORMATION: n is a, t, c, or g

<400> SEQUENCE: 6
taatacgact cactataggg agaggagaga acgttctacn nnnnnnnnn nnnnnnnnn       60 nnnnnnnnng gtcgatcgat cgatcatcga tg                                   92

<210> SEQ ID NO 7
<211> LENGTH: 39
<212> TYPE: DNA
<213> ORGANISM: artificial sequence
<220> FEATURE:
<223> OTHER INFORMATION: synthetic primer

<400> SEQUENCE: 7
taatacgact cactataggg agaggagaga acgttctac                            39

<210> SEQ ID NO 8
<211> LENGTH: 23
<212> TYPE: DNA
<213> ORGANISM: artificial sequence
<220> FEATURE:
<223> OTHER INFORMATION: synthetic primer

<400> SEQUENCE: 8
catcgatgat cgatcgatcg acc                                             23

<210> SEQ ID NO 9
<211> LENGTH: 18
<212> TYPE: RNA
<213> ORGANISM: artificial sequence
<220> FEATURE:
```

```
<223> OTHER INFORMATION: synthetic fixed aptamer sequence
<220> FEATURE:
<221> NAME/KEY: misc_feature
<222> LOCATION: (1)..(18)
<223> OTHER INFORMATION: all guanosine are 2'-OH, all adenosine,
      cytidine, and uridine are 2'-O-methyl

<400> SEQUENCE: 9
uaauacgacu cacuauag                                                      18

<210> SEQ ID NO 10
<211> LENGTH: 23
<212> TYPE: RNA
<213> ORGANISM: artificial sequence
<220> FEATURE:
<223> OTHER INFORMATION: synthetic fixed aptamer sequence
<220> FEATURE:
<221> NAME/KEY: misc_feature
<222> LOCATION: (1)..(23)
<223> OTHER INFORMATION: all guanosine are 2'-OH, all adenosine,
      cytidine, and uridine are 2'-O-methyl

<400> SEQUENCE: 10
ggucgaucga ucgaucaucg aug                                                23

<210> SEQ ID NO 11
<211> LENGTH: 92
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(92)
<223> OTHER INFORMATION: all adenosine, cytidine, and uridine are
      2'-O-methyl, and all guanosine are 2'-OH

<400> SEQUENCE: 11
uaauacgacu cacuauaggg agaggagaga acguucuacu auggguggcu gggagggaa         60 gagggaguag gucgaucgau cgaucaucga ug                                      92

<210> SEQ ID NO 12
<211> LENGTH: 92
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(92)
<223> OTHER INFORMATION: all adenosine, cytidine and uridine are
      2'-O-methyl, and all guanosine are 2'-OH

<400> SEQUENCE: 12
uaauacgacu cacuauaggg gagaggagag aacguucuac acaugggucg ggugaguggc        60
aaaggaauag gucgaucgau cgaucaucga ug                                      92

<210> SEQ ID NO 13
<211> LENGTH: 35
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(35)
<223> OTHER INFORMATION: all adenosine, cytidine and uridine are
      2'-O-methyl, and all guanosine are 2'-OH
```

<400> SEQUENCE: 13
cuacuauggg uggcugggag gggaagaggg aguag                              35

<210> SEQ ID NO 14
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all adenosine, cytidine and uridine are
      2'-O-methyl, and all guanosine are 2'-OH

<400> SEQUENCE: 14
cuacuacaca ugggucgggu gaguggcaaa ggaauaguag                         40

<210> SEQ ID NO 15
<211> LENGTH: 23
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(23)
<223> OTHER INFORMATION: all adenosine, cytidine and uridine are
      2'-O-methyl, and all guanosine are 2'-OH

<400> SEQUENCE: 15
ggguggcugg gaggggaaga ggg                                           23

<210> SEQ ID NO 16
<211> LENGTH: 33
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(33)
<223> OTHER INFORMATION: all adenosine, cytidine and uridine are
      2'-O-methyl, and all guanosine are 2'-OH

<400> SEQUENCE: 16
cuacugggug gcugggaggg gaagagggag uag                                33

<210> SEQ ID NO 17
<211> LENGTH: 38
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all adenosine, cytidine and uridine are
      2'-O-methyl, and all guanosine are 2'-OH

<400> SEQUENCE: 17
agaggagaga acguucuacu auggguggcu gggagggg                           38

<210> SEQ ID NO 18
<211> LENGTH: 39
<212> TYPE: DNA
<213> ORGANISM: artificial
<220> FEATURE:
<223> OTHER INFORMATION: synthetic aptamer

```
<220> FEATURE:
<221> NAME/KEY: misc_feature
<222> LOCATION: (1)..(38)
<223> OTHER INFORMATION: all adenosine, cytidine and uridine are
      2'-O-methyl, and all guanosine are 2'-OH
<220> FEATURE:
<221> NAME/KEY: misc_feature
<222> LOCATION: (1)..(1)
<223> OTHER INFORMATION: 2'-O-methyl adenosine at position 1 is further
      modified by a 5' amine linker
<220> FEATURE:
<221> NAME/KEY: misc_feature
<222> LOCATION: (39)..(39)
<223> OTHER INFORMATION: thymidine at position 39 is an inverted deoxy
      thymidine (3'-3' linked)

<400> SEQUENCE: 18
agaggagaga acguucuacu auggguggcu gggaggggt                              39

<210> SEQ ID NO 19
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all adenosine, cytidine and uridine are
      2'-O-methyl, and all guanosine are 2'-OH
<220> FEATURE:
<221> NAME/KEY: misc_feature
<222> LOCATION: (1)..(1)
<223> OTHER INFORMATION: 2'-O-methyl adenosine at position 1 is futher
      modified by a 5' amine linker
<220> FEATURE:
<221> NAME/KEY: misc_feature
<222> LOCATION: (39)..(39)
<223> OTHER INFORMATION: thymidine at position 39 is an inverted deoxy
      thymidine (3'-3' linked)

<400> SEQUENCE: 19
agaggagaga acguucuacu auggguggcu gggaggggt                              39

<210> SEQ ID NO 20
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(43)
<223> OTHER INFORMATION: all purines are 2'-OH, all pyrimidines are
      2'-fluoro
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 20
cggaccgaaa aagaccugac uucuauacua agucuacguu ccgt                        44

<210> SEQ ID NO 21
<211> LENGTH: 43
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(43)
```

-continued

```
<223> OTHER INFORMATION: all purines are 2'-OH, all pyrimidines are
      2'-fluoro

<400> SEQUENCE: 21
cggaccgaaa aagaccugac uucuauacua agucuacguu ccg                    43

<210> SEQ ID NO 22
<211> LENGTH: 48
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(48)
<223> OTHER INFORMATION: all purines are 2'-OH, all pyrimidines are
      2'-fluoro

<400> SEQUENCE: 22
ggaggaccga aaagaccug acuucuauac uaagucuacg uuccucca                48

<210> SEQ ID NO 23
<211> LENGTH: 48
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(48)
<223> OTHER INFORMATION: all purines are 2'-OH, all pyrimdines are
      2'-fluoro
<220> FEATURE:
<221> NAME/KEY: misc_feature
<222> LOCATION: (1)..(1)
<223> OTHER INFORMATION: guanosine at position 1 is modified by a
      5'-amine linker

<400> SEQUENCE: 23
ggaggaccga aaagaccug acuucuauac uaagucuacg uuccucca                48

<210> SEQ ID NO 24
<211> LENGTH: 48
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(47)
<223> OTHER INFORMATION: all purines are 2'-OH, all pyrimidines are
      2'-fluoro
<220> FEATURE:
<221> NAME/KEY: misc_feature
<222> LOCATION: (1)..(1)
<223> OTHER INFORMATION: guanosine at position 1 is modified by a 5'
      amine linker
<220> FEATURE:
<221> NAME/KEY: misc_feature
<222> LOCATION: (48)..(48)
<223> OTHER INFORMATION: thymidine at position 48 is an inverted deoxy
      thymidine (3'-3' linked)

<400> SEQUENCE: 24
ggaggaccga aaagaccug acuucuauac uaagucuacg uuccucct                48

<210> SEQ ID NO 25
<211> LENGTH: 48
<212> TYPE: DNA
<213> ORGANISM: artificial sequence
<220> FEATURE:
```

```
<223> OTHER INFORMATION: synthetic aptamer
<220> FEATURE:
<221> NAME/KEY: misc_feature
<222> LOCATION: (1)..(47)
<223> OTHER INFORMATION: all purines are 2'-OH, all pyrimidines are
      2'-fluoro
<220> FEATURE:
<221> NAME/KEY: misc_feature
<222> LOCATION: (1)..(1)
<223> OTHER INFORMATION: guanosine at position 1 is modified by
      5'-fluoroscein
<220> FEATURE:
<221> NAME/KEY: misc_feature
<222> LOCATION: (48)..(48)
<223> OTHER INFORMATION: thymidine at position 48 is an inverted deoxy
      thymidine (3'-3' linked)

<400> SEQUENCE: 25
ggaggaccga aaaagaccug acuucuauac uaagucuacg uuccucct                    48

<210> SEQ ID NO 26
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all guanosine are 2'-OH, except at positions 2,
      3, 7, 13, 32, 38 and 43, wherein guanosine is 2'-O-methyl
<220> FEATURE:
<221> NAME/KEY: misc_feature
<223> OTHER INFORMATION: all adenosine are 2'-OH, except at positions 4,
      12, 14, and 27, wherein adenosine is 2'-O-methyl
<220> FEATURE:
<221> NAME/KEY: misc_feature
<223> OTHER INFORMATION: all all uridine are 2'-fluoro, except at
      positions 33, 35, and 40, wherein uridine is 2'-O-methyl
<220> FEATURE:
<221> NAME/KEY: misc_feature
<223> OTHER INFORMATION: all cytidine are 2'-fluoro, except at positions
      1, 15, 34, 41, and 42, wherein cytidine is 2'-O-methyl
<220> FEATURE:
<221> NAME/KEY: misc_feature
<222> LOCATION: (1)..(1)
<223> OTHER INFORMATION: 2'-O-methyl cytidine at position 1 is further
      modified by 5'-fluoroscein
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 26
cggaccgaaa aagaccugac uucuauacua agucuacguu ccgt                        44

<210> SEQ ID NO 27
<211> LENGTH: 92
<212> TYPE: DNA
<213> ORGANISM: artificial sequence
<220> FEATURE:
<223> OTHER INFORMATION: synthetic template
<220> FEATURE:
<221> NAME/KEY: misc_feature
<222> LOCATION: (19)..(66)
<223> OTHER INFORMATION: nucleotides at positions 19-36 each have an 85%
      chance of being the indicated nucleotide, and a 5% chance of being
      one of the other three nucleotides

<400> SEQUENCE: 27
cgcaaggacg aagggaggac gatgcggacc gaaaagacc tgacttctat actaagtcta        60
cgttcccaga cgactcgccc gaggtcgatt cc                                     92
```

```
<210> SEQ ID NO 28
<211> LENGTH: 35
<212> TYPE: DNA
<213> ORGANISM: artificial sequence
<220> FEATURE:
<223> OTHER INFORMATION: synthetic primer

<400> SEQUENCE: 28
taatacgact cactataggc aaggacgaag ggagg                              35

<210> SEQ ID NO 29
<211> LENGTH: 18
<212> TYPE: DNA
<213> ORGANISM: artificial sequence
<220> FEATURE:
<223> OTHER INFORMATION: synthetic primer

<400> SEQUENCE: 29
tggaatcgac ctcgggcg                                                 18

<210> SEQ ID NO 30
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 30
ggaccggaaa agaccugacu ucuauacuaa gucuacguuc c                       41

<210> SEQ ID NO 31
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 31
ggaccgaaaa agaccugacu ucuauacuaa gucuacguua c                       41

<210> SEQ ID NO 32
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, alll pyrimidines are
      2'-fluoro

<400> SEQUENCE: 32
ggaccgaaaa agaccugacu ucuauacuaa gucuacguug c                       41

<210> SEQ ID NO 33
<211> LENGTH: 41
<212> TYPE: RNA
```

```
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 33
ggaccgaaaa agaccugaau ucuauacuaa gucuacguuc c                    41

<210> SEQ ID NO 34
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 34
ggaccgaaca agaccugacu ucuauacuaa gucuacguuc c                    41

<210> SEQ ID NO 35
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all purines are 2'-OH, all pyrimidines are
      2'-fluoro

<400> SEQUENCE: 35
ggaccggaaa agaccugauu cuauacuaag ucuacguucc                      40

<210> SEQ ID NO 36
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 36
ggaccguaaa agaccugacu ucuauacuaa gucuacguug c                    41

<210> SEQ ID NO 37
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 37
```

```
ggaccgaaaa agaccugacu ucuauacuaa ggcuacguug c                    41
```

<210> SEQ ID NO 38
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 38

```
ggaccgaaca agaccugauu ucuauacuaa gucuacguuc c                    41
```

<210> SEQ ID NO 39
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 39

```
ggaccgaaaa aggccugacu ucuauacuaa gccuacguuc c                    41
```

<210> SEQ ID NO 40
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all purines are 2'-OH, all pyrimidines are
      2'-fluoro

<400> SEQUENCE: 40

```
ggaccguaaa gaccugacuu cuauacuaag ucuacguucc                       40
```

<210> SEQ ID NO 41
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 41

```
ggacccgaaa agaccugacu ucuauacuaa gucuacguua c                    41
```

<210> SEQ ID NO 42
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature

```
<222> LOCATION: (1)..(41)
<223> OTHER INFORMATION: all purines are 2'-OH, all pyrimidines are
      2'-fluoro

<400> SEQUENCE: 42
ggaccgaaca agaccugacu ucuguacuaa gucuacguuc c                           41

<210> SEQ ID NO 43
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 43
ggaccgaaua agaccugacu ucuguacuaa gucuacguuc c                           41

<210> SEQ ID NO 44
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all purines are 2'-OH, all pyrimidines are
      2'-fluoro

<400> SEQUENCE: 44
ggaccggaaa ggaccugauu cuauacuaag ucuacguucc                             40

<210> SEQ ID NO 45
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all purines are 2'-OH, all pyrimidines are
      2'-fluoro

<400> SEQUENCE: 45
cgaccgaaaa agaccugacu ucuauacuaa gucuacguua                             40

<210> SEQ ID NO 46
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 46
ggaccggaaa agaccugaau ucuauacuaa gucuacguac c                           41

<210> SEQ ID NO 47
<211> LENGTH: 41
```

```
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 47
ggaccgaaaa ggaccugacu ucuauacuaa guccacguuc c                41

<210> SEQ ID NO 48
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 48
ggaccgaaca agcccugacu ucuauacuaa ggcuacguuc c                41

<210> SEQ ID NO 49
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all purines are 2'-OH, all pyrimidines are
      2'-fluoro

<400> SEQUENCE: 49
ggaccggaaa gaccugacuu cuauacuaag ucuacguucc                  40

<210> SEQ ID NO 50
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 50
ggaccgagaa agaccugaau ucuauacuaa gucuacguua c                41

<210> SEQ ID NO 51
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all purines are 2'-OH, all pyrimidines are
      2'-fluoro

<400> SEQUENCE: 51
```
ggaccguaaa gaccugacuu cuauacuaag ucuacgugcc                    40

<210> SEQ ID NO 52
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 52
ggaccggaaa agcccugacu ucuauacuaa ggcuccguuc c                  41

<210> SEQ ID NO 53
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 53
cgaccgaaaa agaccugaau ucuauacuaa gucuacguua c                  41

<210> SEQ ID NO 54
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all purines are 2'-OH, all pyrimidines are
      2'-fluoro

<400> SEQUENCE: 54
ggaccguaaa gaccugauuu cuauacuaag ucuacguucc                    40

<210> SEQ ID NO 55
<211> LENGTH: 39
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(39)
<223> OTHER INFORMATION: all purines are 2'-OH, all pyrimidines are
      2'-fluoro

<400> SEQUENCE: 55
ggaccguaaa gaccugauuc uauacuaagu cuacguucc                     39

<210> SEQ ID NO 56
<211> LENGTH: 42
<212> TYPE: RNA
<213> ORGANISM: artificial sequence
<220> FEATURE:
<223> OTHER INFORMATION: synthetic aptamer
<220> FEATURE:

```
<221> NAME/KEY: misc_feature
<222> LOCATION: (1)..(42)
<223> OTHER INFORMATION: all purines are 2'-OH, all pyrimidines are
      2'-fluoro

<400> SEQUENCE: 56
ggacccgaaa aagaccugag uucuauacua agucuacguu cc                          42

<210> SEQ ID NO 57
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 57
ggaccgaaca agcccugacu ucuauacuaa ggcuacgugc c                           41

<210> SEQ ID NO 58
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all purines are 2'-OH, all pyrimidines are
      2'-fluoro

<400> SEQUENCE: 58
ggaccggaaa gaccugauuu cuauacuaag ucuacguuac                             40

<210> SEQ ID NO 59
<211> LENGTH: 42
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(42)
<223> OTHER INFORMATION: all purines are 2'-OH, all pyrimidines are
      2'-fluoro

<400> SEQUENCE: 59
ggacccgaaa aagaccugac uucuauacua agucuacgua cc                          42

<210> SEQ ID NO 60
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 60
ggaccgaaaa acaccugaau ucuauacuaa guguacguuc c                           41

<210> SEQ ID NO 61
```

```
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 61
ggaccgaaca agaccugacu ucuguacuaa gacuacguug c                    41

<210> SEQ ID NO 62
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all purines are 2'-OH, all pyrimidines are
      2'-fluoro

<400> SEQUENCE: 62
ggaccguaaa gaccugauuu cuauacuaag ucuacguuac                      40

<210> SEQ ID NO 63
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 63
ggaccgaaaa acaccugacu ucuauacuaa ggcuacguau g                    41

<210> SEQ ID NO 64
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 64
ggaccgaaua aggccugacu ucuauacuaa gccugcguuc c                    41

<210> SEQ ID NO 65
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all purines are 2'-OH, all pyrimidines are
      2'-fluoro
```

```
<400> SEQUENCE: 65
ggaccguaaa ggccugacuu cuauacuaag ccuacguucc                    40

<210> SEQ ID NO 66
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 66
ggaccgaaua agaccugagu ucguacuaa gucuccguuc c                   41

<210> SEQ ID NO 67
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 67
ggacccaaaa aggccugacu ucuauacuaa gccuauguuc c                  41

<210> SEQ ID NO 68
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 68
guaccggaaa ggcccugacu ucuauacuaa ggcuacguug c                  41

<210> SEQ ID NO 69
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 69
cgaccgaaaa aggccugacu ucuauacuaa gccuacguac c                  41

<210> SEQ ID NO 70
<211> LENGTH: 39
<212> TYPE: RNA
<213> ORGANISM: artificial sequence
<220> FEATURE:
<223> OTHER INFORMATION: synthetic aptamer
```

```
<220> FEATURE:
<221> NAME/KEY: misc_feature
<222> LOCATION: (1)..(39)
<223> OTHER INFORMATION: all purines are 2'-OH, all pyrimidines are
      2'-fluoro

<400> SEQUENCE: 70
ggaccguaaa gaccugauuc uauacuaagu cuacguacc                              39

<210> SEQ ID NO 71
<211> LENGTH: 42
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(42)
<223> OTHER INFORMATION: all purines are 2'-OH, all pyrimidines are
      2'-fluoro

<400> SEQUENCE: 71
ggacccgaaa aagaccugag uucuauacua agucuccguu cc                          42

<210> SEQ ID NO 72
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 72
guaccgagga agaccugacu ucuguacuaa gucuacguua c                           41

<210> SEQ ID NO 73
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 73
guaccggaaa ggcccugacu ucuauacuaa ggccacguug c                           41

<210> SEQ ID NO 74
<211> LENGTH: 41
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(41)
<223> OTHER INFORMATION: all purines are 2'-OH, all pyrimidines are
      2'-fluoro

<400> SEQUENCE: 74
ggaccuguaa agaccugaau ucuauacuaa gucuacaugc c                           41
```

```
<210> SEQ ID NO 75
<211> LENGTH: 43
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(43)
<223> OTHER INFORMATION: all purines are 2'-OH, all pyrimidines are
      2'-fluoro

<400> SEQUENCE: 75
gaaccgaaga aagaccugaa cuucuauacu aaggcuacgu uug                           43

<210> SEQ ID NO 76
<211> LENGTH: 39
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(39)
<223> OTHER INFORMATION: all purines are 2'-OH, all pyrimidines are
      2'-fluoro

<400> SEQUENCE: 76
ggaccguaaa gaccggauuc uauacuaagu cuacguuac                                39

<210> SEQ ID NO 77
<211> LENGTH: 48
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(48)
<223> OTHER INFORMATION: all purines are 2'-OH, all pyrimidines are
      2'-fluoro

<400> SEQUENCE: 77
ggaggacccg aaaaagaccu gacuucuaua cuaagucuac guuccucc                      48

<210> SEQ ID NO 78
<211> LENGTH: 47
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(47)
<223> OTHER INFORMATION: all purines are 2'-OH, all pyrimidines are
      2'-fluoro

<400> SEQUENCE: 78
ggaggaccgg aaaagaccug acuucuauac uaagucuacg uuccucc                       47

<210> SEQ ID NO 79
<211> LENGTH: 47
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(47)
<223> OTHER INFORMATION: all purines are 2'-OH, all pyrimidines are
      2'-fluoro
```

-continued

```
<400> SEQUENCE: 79
ggaggaccga acaagaccug acuucuauac uaagucuacg uuccucc                47

<210> SEQ ID NO 80
<211> LENGTH: 47
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(47)
<223> OTHER INFORMATION: all purines are 2'-OH, all pyrimidines are
      2'-fluoro

<400> SEQUENCE: 80
ggaggaccga aaaggaccug acuucuauac uaaguccacg uuccucc                47

<210> SEQ ID NO 81
<211> LENGTH: 47
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(47)
<223> OTHER INFORMATION: all purines are 2'-OH, all pyrimidines are
      2'-fluoro

<400> SEQUENCE: 81
ggaggaccga aaaacaccug acuucuauac uaaguguacg uuccucc                47

<210> SEQ ID NO 82
<211> LENGTH: 47
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(47)
<223> OTHER INFORMATION: all purines are 2'-OH, all pyrimidines are
      2'-fluoro

<400> SEQUENCE: 82
ggaggaccga aaaagcccug acuucuauac uaaggcuacg uuccucc                47

<210> SEQ ID NO 83
<211> LENGTH: 47
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(47)
<223> OTHER INFORMATION: all purines are 2'-OH, all pyrimidines are
      2'-fluoro

<400> SEQUENCE: 83
ggaggaccga aaaaggccug acuucuauac uaagccuacg uuccucc                47

<210> SEQ ID NO 84
<211> LENGTH: 47
<212> TYPE: RNA
<213> ORGANISM: artificial sequence
<220> FEATURE:
```

```
<223> OTHER INFORMATION: synthetic aptamer
<220> FEATURE:
<221> NAME/KEY: misc_feature
<222> LOCATION: (1)..(47)
<223> OTHER INFORMATION: all purines are 2'-OH, all pyrimidines are
      2'-fluoro

<400> SEQUENCE: 84
ggaggaccga aaagaccug acuucuguac uaagucuacg uuccucc                    47

<210> SEQ ID NO 85
<211> LENGTH: 47
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(47)
<223> OTHER INFORMATION: all purines are 2'-OH, all pyrimidines are
      2'-fluoro

<400> SEQUENCE: 85
ggaggaccga aaagaccug acuucuauac uaagucuacg uaccucc                    47

<210> SEQ ID NO 86
<211> LENGTH: 47
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(47)
<223> OTHER INFORMATION: all purines are 2'-OH, all pyrimidines are
      2'-fluoro

<400> SEQUENCE: 86
ggaggaccga aaagaccug acuucuauac uaagucuacg uuacucc                    47

<210> SEQ ID NO 87
<211> LENGTH: 48
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 3
      and 6, wherein adenosine is 2'-O-methyl
<220> FEATURE:
<221> NAME/KEY: misc_feature
<223> OTHER INFORMATION: all guanosine are 2'-OH, except at positions 1,
      2, 4, and 5, wherein guanosine is 2'-O-methyl
<220> FEATURE:
<221> NAME/KEY: misc_feature
<223> OTHER INFORMATION: all cytidine are 2'-fluoro, except at positions
      43, 44, 46, and 47, wherein cytidine is 2'-O-methyl
<220> FEATURE:
<221> NAME/KEY: misc_feature
<223> OTHER INFORMATION: all uridine are 2'-fluoro, except at positions
      42 and 45, wherein uridine is 2'-O-methyl

<400> SEQUENCE: 87
ggaggaccga aaagaccug acuucuauac uaagucuacg uuccucca                   48

<210> SEQ ID NO 88
<211> LENGTH: 44
<212> TYPE: DNA
<213> ORGANISM: artificial sequence
<220> FEATURE:
```

```
<223> OTHER INFORMATION: synthetic aptamer
<220> FEATURE:
<221> NAME/KEY: misc_feature
<223> OTHER INFORMATION: all adenosine are 2'-OH, except at positions 4
      and 12, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (1)..(1)
<223> OTHER INFORMATION: 2'-O-methyl cytidine at position 1 is further
      modified by a 5'-amine linker
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 88
cggaccgaac aaggccugac uucuauacua agccuacguu ccgt            44

<210> SEQ ID NO 89
<211> LENGTH: 44
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4
      and 12, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41, and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl, and at position 44,
      wherein uridine is 2'-OH
<220> FEATURE:
<221> NAME/KEY: misc_feature
<222> LOCATION: (1)..(1)
<223> OTHER INFORMATION: 2'-O-methyl cytidine at position 1 is further
      modified by a 5' amine linker

<400> SEQUENCE: 89
cggaccgaac aaggccugac uucuauacua agccuacguu ccgu            44

<210> SEQ ID NO 90
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4
      and 12, wherein adenosine is 2'-O-methyl
<220> FEATURE:
<221> NAME/KEY: misc_feature
```

```
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 90
cggaccgaac aaggccugac uucuauacua agccuacguu ccgt            44

<210> SEQ ID NO 91
<211> LENGTH: 18
<212> TYPE: DNA
<213> ORGANISM: artificial sequence
<220> FEATURE:
<223> OTHER INFORMATION: synthetic primer

<400> SEQUENCE: 91
ccgtacgaga gtgcgtaa                                         18

<210> SEQ ID NO 92
<211> LENGTH: 18
<212> TYPE: DNA
<213> ORGANISM: artificial sequence
<220> FEATURE:
<223> OTHER INFORMATION: synthetic primer

<400> SEQUENCE: 92
ggaggaacgt agacttag                                         18

<210> SEQ ID NO 93
<211> LENGTH: 79
<212> TYPE: DNA
<213> ORGANISM: artificial sequence
<220> FEATURE:
<223> OTHER INFORMATION: synthetic template

<400> SEQUENCE: 93
cgtacgagag tgcgtaatac gactcactat aggaggaccc gaaaaagacc tgacttctat    60
actaagtcta cgttcctcc                                                79

<210> SEQ ID NO 94
<211> LENGTH: 18
<212> TYPE: DNA
<213> ORGANISM: artificial sequence
<220> FEATURE:
<223> OTHER INFORMATION: synthetic primer

<400> SEQUENCE: 94
ccgtacgaga gtgcgtaa                                         18

<210> SEQ ID NO 95
<211> LENGTH: 18
<212> TYPE: DNA
<213> ORGANISM: artificial sequence
<220> FEATURE:
<223> OTHER INFORMATION: synthetic primer

<400> SEQUENCE: 95
```

```
ggaggaacgt agacttag                                              18

<210> SEQ ID NO 96
<211> LENGTH: 79
<212> TYPE: DNA
<213> ORGANISM: artificial sequence
<220> FEATURE:
<223> OTHER INFORMATION: synthetic template

<400> SEQUENCE: 96
ccgtacgaga gtgcgtaata cgactcacta taggaggacc ggaaaagacc tgacttctat    60
actaagtcta cgttcctcc                                                 79

<210> SEQ ID NO 97
<211> LENGTH: 18
<212> TYPE: DNA
<213> ORGANISM: artificial sequence
<220> FEATURE:
<223> OTHER INFORMATION: synthetic primer

<400> SEQUENCE: 97
ccgtacgaga gtgcgtaa                                                  18

<210> SEQ ID NO 98
<211> LENGTH: 18
<212> TYPE: DNA
<213> ORGANISM: artificial sequence
<220> FEATURE:
<223> OTHER INFORMATION: synthetic primer

<400> SEQUENCE: 98
ggaggaacgt agacttag                                                  18

<210> SEQ ID NO 99
<211> LENGTH: 79
<212> TYPE: DNA
<213> ORGANISM: artificial sequence
<220> FEATURE:
<223> OTHER INFORMATION: synthetic template

<400> SEQUENCE: 99
ccgtacgaga gtgcgtaata cgactcacta taggaggacc gaacaagacc tgacttctat    60
actaagtcta cgttcctcc                                                 79

<210> SEQ ID NO 100
<211> LENGTH: 18
<212> TYPE: DNA
<213> ORGANISM: artificial sequence
<220> FEATURE:
<223> OTHER INFORMATION: synthetic primer

<400> SEQUENCE: 100
ccgtacgaga gtgcgtaa                                                  18

<210> SEQ ID NO 101
<211> LENGTH: 18
<212> TYPE: DNA
<213> ORGANISM: artificial sequence
<220> FEATURE:
<223> OTHER INFORMATION: synthetic primer

<400> SEQUENCE: 101
ggaggaacgt ggacttag                                                  18
```

```
<210> SEQ ID NO 102
<211> LENGTH: 79
<212> TYPE: DNA
<213> ORGANISM: artificial sequence
<220> FEATURE:
<223> OTHER INFORMATION: synthetic template

<400> SEQUENCE: 102
ccgtacgaga gtgcgtaata cgactcacta taggaggacc gaaaaggacc tgacttctat      60
actaagtcca cgttcctcc                                                   79

<210> SEQ ID NO 103
<211> LENGTH: 18
<212> TYPE: DNA
<213> ORGANISM: artificial sequence
<220> FEATURE:
<223> OTHER INFORMATION: synthetic primer

<400> SEQUENCE: 103
ccgtacgaga gtgcgtaa                                                    18

<210> SEQ ID NO 104
<211> LENGTH: 18
<212> TYPE: DNA
<213> ORGANISM: artificial sequence
<220> FEATURE:
<223> OTHER INFORMATION: synthetic primer

<400> SEQUENCE: 104
ggaggaacgt agccttag                                                    18

<210> SEQ ID NO 105
<211> LENGTH: 79
<212> TYPE: DNA
<213> ORGANISM: artificial sequence
<220> FEATURE:
<223> OTHER INFORMATION: synthetic template

<400> SEQUENCE: 105
ccgtacgaga gtgcgtaata cgactcacta taggaggacc gaaaaacacc tgacttctat      60
actaagtgta cgttcctcc                                                   79

<210> SEQ ID NO 106
<211> LENGTH: 18
<212> TYPE: DNA
<213> ORGANISM: artificial sequence
<220> FEATURE:
<223> OTHER INFORMATION: synthetic primer

<400> SEQUENCE: 106
ccgtacgaga gtgcgtaa                                                    18

<210> SEQ ID NO 107
<211> LENGTH: 18
<212> TYPE: DNA
<213> ORGANISM: artificial sequence
<220> FEATURE:
<223> OTHER INFORMATION: synthetic primer

<400> SEQUENCE: 107
ggaggaacgt agccttag                                                    18

<210> SEQ ID NO 108
<211> LENGTH: 79
```

```
<212> TYPE: DNA
<213> ORGANISM: artificial sequence
<220> FEATURE:
<223> OTHER INFORMATION: synthetic template

<400> SEQUENCE: 108
ccgtacgaga gtgcgtaata cgactcacta taggaggacc gaaaaagccc tgacttctat      60
actaaggcta cgttcctcc                                                   79

<210> SEQ ID NO 109
<211> LENGTH: 18
<212> TYPE: DNA
<213> ORGANISM: artificial sequence
<220> FEATURE:
<223> OTHER INFORMATION: synthetic primer

<400> SEQUENCE: 109
ccgtacgaga gtgcgtaa                                                    18

<210> SEQ ID NO 110
<211> LENGTH: 18
<212> TYPE: DNA
<213> ORGANISM: artificial sequence
<220> FEATURE:
<223> OTHER INFORMATION: synthetic primer

<400> SEQUENCE: 110
ggaggaacgt aggcttag                                                    18

<210> SEQ ID NO 111
<211> LENGTH: 79
<212> TYPE: DNA
<213> ORGANISM: artificial sequence
<220> FEATURE:
<223> OTHER INFORMATION: synthetic template

<400> SEQUENCE: 111
ccgtacgaga gtgcgtaata cgactcacta taggaggacc gaaaaaggcc tgacttctat      60
actaagccta cgttcctcc                                                   79

<210> SEQ ID NO 112
<211> LENGTH: 18
<212> TYPE: DNA
<213> ORGANISM: artificial sequence
<220> FEATURE:
<223> OTHER INFORMATION: synthetic primer

<400> SEQUENCE: 112
ccgtacgaga gtgcgtaa                                                    18

<210> SEQ ID NO 113
<211> LENGTH: 18
<212> TYPE: DNA
<213> ORGANISM: artificial sequence
<220> FEATURE:
<223> OTHER INFORMATION: synthetic primer

<400> SEQUENCE: 113
ggaggaacgt agacttag                                                    18

<210> SEQ ID NO 114
<211> LENGTH: 79
<212> TYPE: DNA
<213> ORGANISM: artificial sequence
<220> FEATURE:
```

```
<223> OTHER INFORMATION: synthetic template

<400> SEQUENCE: 114
ccgtacgaga gtgcgtaata cgactcacta taggaggacc gaaaaagacc tgacttctgt    60
actaagtcta cgttcctcc                                                 79

<210> SEQ ID NO 115
<211> LENGTH: 18
<212> TYPE: DNA
<213> ORGANISM: artificial sequence
<220> FEATURE:
<223> OTHER INFORMATION: synthetic primer

<400> SEQUENCE: 115
ccgtacgaga gtgcgtaa                                                  18

<210> SEQ ID NO 116
<211> LENGTH: 18
<212> TYPE: DNA
<213> ORGANISM: artificial sequence
<220> FEATURE:
<223> OTHER INFORMATION: synthetic primer

<400> SEQUENCE: 116
ggaggtacgt agacttag                                                  18

<210> SEQ ID NO 117
<211> LENGTH: 79
<212> TYPE: DNA
<213> ORGANISM: artificial sequence
<220> FEATURE:
<223> OTHER INFORMATION: synthetic template

<400> SEQUENCE: 117
ccgtacgaga gtgcgtaata cgactcacta taggaggacc gaaaaagacc tgacttctat    60
actaagtcta cgtacctcc                                                 79

<210> SEQ ID NO 118
<211> LENGTH: 18
<212> TYPE: DNA
<213> ORGANISM: artificial sequence
<220> FEATURE:
<223> OTHER INFORMATION: synthetic primer

<400> SEQUENCE: 118
ccgtacgaga gtgcgtaa                                                  18

<210> SEQ ID NO 119
<211> LENGTH: 18
<212> TYPE: DNA
<213> ORGANISM: artificial sequence
<220> FEATURE:
<223> OTHER INFORMATION: synthetic primer

<400> SEQUENCE: 119
ggagtaacgt agacttag                                                  18

<210> SEQ ID NO 120
<211> LENGTH: 79
<212> TYPE: DNA
<213> ORGANISM: artificial sequence
<220> FEATURE:
<223> OTHER INFORMATION: synthetic template

<400> SEQUENCE: 120
```

```
ccgtacgaga gtgcgtaata cgactcacta taggaggacc gaaaaagacc tgacttctat    60
actaagtcta cgttactcc                                                  79
```

<210> SEQ ID NO 121
<211> LENGTH: 0
<212> TYPE: RNA
<213> ORGANISM: artificial sequence
<220> FEATURE:
<223> OTHER INFORMATION: synthetic aptamer

<400> SEQUENCE: 121

000

<210> SEQ ID NO 122
<211> LENGTH: 48
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 3
      and 6, wherein adenosine is 2'-O-methyl
<220> FEATURE:
<221> NAME/KEY: misc_feature
<223> OTHER INFORMATION: all guanosine are 2'-OH, except at positions 1,
      2, 4 and 5, wherein adenosine is 2'-O-methyl
<220> FEATURE:
<221> NAME/KEY: misc_feature
<223> OTHER INFORMATION: all cytidine are 2'-fluoro
<220> FEATURE:
<221> NAME/KEY: misc_feature
<223> OTHER INFORMATION: all uridine are 2'-fluoro

<400> SEQUENCE: 122

```
ggaggaccga aaaagaccug acuucuauac uaagucuacg uuccucca                  48
```

<210> SEQ ID NO 123
<211> LENGTH: 48
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH
<220> FEATURE:
<221> NAME/KEY: misc_feature
<223> OTHER INFORMATION: all guanosine are 2'-OH, except at positions 9
      and 40, wherein guanosine is 2'-O-methyl
<220> FEATURE:
<221> NAME/KEY: misc_feature
<223> OTHER INFORMATION: all cytidine  2'-fluoro
<220> FEATURE:
<221> NAME/KEY: misc_feature
<223> OTHER INFORMATION: all uridine 2'-fluoro

<400> SEQUENCE: 123

```
ggaggaccga aaaagaccug acuucuauac uaagucuacg uuccucca                  48
```

<210> SEQ ID NO 124
<211> LENGTH: 48
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH
<220> FEATURE:

<221> NAME/KEY: misc_feature
<223> OTHER INFORMATION: all guanosine are 2'-OH, except at positions 15
     and 34, wherein guanosine are 2'-O-methyl
<220> FEATURE:
<221> NAME/KEY: misc_feature
<223> OTHER INFORMATION: all cytidine are 2'-fluoro
<220> FEATURE:
<221> NAME/KEY: misc_feature
<223> OTHER INFORMATION: all uridine are 2'-fluoro

<400> SEQUENCE: 124
ggaggaccga aaaagaccug acuucuauac uaagucuacg uuccucca                48

<210> SEQ ID NO 125
<211> LENGTH: 48
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH
<220> FEATURE:
<221> NAME/KEY: misc_feature
<223> OTHER INFORMATION: all guanosine are 2'-OH, except at positions 9
     and 40, wherein guanosine is 2'-O-methyl
<220> FEATURE:
<221> NAME/KEY: misc_feature
<223> OTHER INFORMATION: all cytidine are 2'-fluoro, except at positions
     8 and 39, wherein cytidine is 2'-O-methyl
<220> FEATURE:
<221> NAME/KEY: misc_feature
<223> OTHER INFORMATION: all uridine are 2'-fluoro

<400> SEQUENCE: 125
ggaggaccga aaaagaccug acuucuauac uaagucuacg uuccucca                48

<210> SEQ ID NO 126
<211> LENGTH: 48
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 14
     and 16, wherein adenosine is 2'-O-methyl
<220> FEATURE:
<221> NAME/KEY: misc_feature
<223> OTHER INFORMATION: all guanosine are 2'-OH, except at positions 15
     and 34, wherein guanosine is 2'-O-methyl
<220> FEATURE:
<221> NAME/KEY: misc_feature
<223> OTHER INFORMATION: all cytidine are 2'-fluoro, except at positions
     17 and 36, wherein cytidine is 2'-O-methyl
<220> FEATURE:
<221> NAME/KEY: misc_feature
<223> OTHER INFORMATION: all uridine are 2'-fluoro, except at positions
     35 and 37, wherein uridine is 2'-O-methyl

<400> SEQUENCE: 126
ggaggaccga aaaagaccug acuucuauac uaagucuacg uuccucca                48

<210> SEQ ID NO 127
<211> LENGTH: 48
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 3,
     6, 14 and 16, wherein adenosine is 2'-O-methyl

```
<220> FEATURE:
<221> NAME/KEY: misc_feature
<223> OTHER INFORMATION: all guanosine are 2'-O-methyl, except at
      position 20, wherein guanosine is 2'-OH
<220> FEATURE:
<221> NAME/KEY: misc_feature
<223> OTHER INFORMATION: all cytidine are 2'-fluoro, except at positions
      17, 36, 43, 44, 46 and 47, wherein cytidine is 2'-O-methyl
<220> FEATURE:
<221> NAME/KEY: misc_feature
<223> OTHER INFORMATION: all uridine are 2'-fluoro, except at positions
      35, 37, 42, and 45, wherein uridine is 2'-O-methyl
<220> FEATURE:
<221> NAME/KEY: misc_feature
<222> LOCATION: (48)..(48)
<223> OTHER INFORMATION: thymidine at position 48 is an inverted deoxy
      thymidine (3'-3' linked)

<400> SEQUENCE: 127
ggaggaccga aaaagaccug acuucuauac uaagucuacg uuccucct                    48

<210> SEQ ID NO 128
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      12, and 14, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are  2'-fluoro, except at
      positions 1, 15, 34, 41 and 42, wherein cytidine is 2'-O-methyl
<220> FEATURE:
<221> NAME/KEY: misc_feature
<223> OTHER INFORMATION: all uridine are  2'-fluoro, except at positions
      33, 35, and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3' 3' linked)

<400> SEQUENCE: 128
cggaccgaaa aagaccugac uucuauacua agucuacguu ccgt                       44

<210> SEQ ID NO 129
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      12, and 14, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      33, 35 and 40, wherein  uridine is 2'-O-methyl
<220> FEATURE:
```

```
<221> NAME/KEY: misc_feature
<222> LOCATION: (1)..(1)
<223> OTHER INFORMATION: 2'-O-methyl cytidine at position 1 is further
      modified by a 5'-amine linker
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 129
cggaccgaaa aagaccugac uucuauacua agucuacguu ccgt                44

<210> SEQ ID NO 130
<211> LENGTH: 44
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      12, and 14, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 34, 41, and 42, wherein cytidine is 2'-O-methyl
<220> FEATURE:
<221> NAME/KEY: misc_feature
<223> OTHER INFORMATION: all uridine are 2'-fluoro, except at positions
      33, 35 and 40, wherein uridine is 2'-O-methyl, and at position 44,
      wherein uridine is 2'-OH

<400> SEQUENCE: 130
cggaccgaaa aagaccugac uucuauacua agucuacguu ccgu                44

<210> SEQ ID NO 131
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      8, and 10, wherein adenosine is 2'-O-methyl
<220> FEATURE:
<221> NAME/KEY: misc_feature
<223> OTHER INFORMATION: all guanosine are 2'-O-methyl, except at
      position 14, wherein guanosine is 2'-OH
<220> FEATURE:
<221> NAME/KEY: misc_feature
<223> OTHER INFORMATION: all cytidine are 2'-fluoro, except at positions
      1, 11, 30, 36, and 37, wherein cytidine is 2'-O-methyl
<220> FEATURE:
<221> NAME/KEY: misc_feature
<223> OTHER INFORMATION: all uridine are 2'-fluoro, except at positions
      29, 31 and 35, wherein uridine is 2'-O-methyl
<220> FEATURE:
<221> NAME/KEY: misc_feature
<222> LOCATION: (39)..(39)
<223> OTHER INFORMATION: thymidine at position 39 is an inverted deoxy
      thymidine (3'-3' linked)

<400> SEQUENCE: 131
cggaccgaga ccugacuucu auacuaaguc ucggccgt                       39

<210> SEQ ID NO 132
<211> LENGTH: 44
```

```
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      12 and 14, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      33, 35 and 40, wherein uridine is 2'-O-methyl
<220> FEATURE:
<221> NAME/KEY: misc_feature
<223> OTHER INFORMATION: 2'-O-methyl cytidine at position 1 is further
      modified by a 5'-fluoroscein
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 132
cggaccgaaa aagaccugac uucuauacua agucuacguu ccgt            44

<210> SEQ ID NO 133
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      8, and 12, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      33, 35, and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 133
cggaccgaac aaggccugac uucuauacua agccuacguu ccgt            44

<210> SEQ ID NO 134
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      9, and 12, wherein adenosine is 2'-O-methyl
<220> FEATURE:
```

<221> NAME/KEY: misc_feature
<223> OTHER INFORMATION: all guanosine are 2'-O-methyl, except at
     position 18, wherein guanosine is 2'-OH
<220> FEATURE:
<221> NAME/KEY: misc_feature
<223> OTHER INFORMATION: all cytidine are 2'-fluoro, except at positions
     1, 15, 33, 34, 41, and 42, wherein cytidine is 2'-O-methyl
<220> FEATURE:
<221> NAME/KEY: misc_feature
<223> OTHER INFORMATION: all uridine are 2'-fluoro, except at positions
     35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
     thymidine (3'-3' linked)

<400> SEQUENCE: 134
cggaccgaac aaggccugac uucuauacua agccuacguu ccgt          44

<210> SEQ ID NO 135
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
     11 and 12, wherein adenosine is 2'-O-methyl
<220> FEATURE:
<221> NAME/KEY: misc_feature
<223> OTHER INFORMATION: all guanosine are 2'-O-methyl, except at
     position 18, wherein guanosine is 2'-OH
<220> FEATURE:
<221> NAME/KEY: misc_feature
<223> OTHER INFORMATION: all cytidine are 2'-fluoro, except at positions
     1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
     35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
     thymidine (3'-3' linked)

<400> SEQUENCE: 135
cggaccgaac aaggccugac uucuauacua agccuacguu ccgt          44

<210> SEQ ID NO 136
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4
     and 12, wherein adenosine is 2'-O-methyl
<220> FEATURE:
<221> NAME/KEY: misc_feature
<223> OTHER INFORMATION: all guanosine are 2'-O-methyl
<220> FEATURE:
<221> NAME/KEY: misc_feature
<223> OTHER INFORMATION: all cytidine are 2'-fluoro, except at positions
     1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
     35 and 40, wherein uridine is 2'-O-methyl
<220> FEATURE:
<221> NAME/KEY: misc_feature
<222> LOCATION: (44)..(44)

<223> OTHER INFORMATION: thymidine at position 44 is an inverted deoxy
      thymidine (3'-3' linked)

<400> SEQUENCE: 136
cggaccgaac aaggccugac uucuauacua agccuacguu ccgt        44

<210> SEQ ID NO 137
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      12 and 19, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 137
cggaccgaac aaggccugac uucuauacua agccuacguu ccgt        44

<210> SEQ ID NO 138
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      12 and 25, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 138
cggaccgaac aaggccugac uucuauacua agccuacguu ccgt        44

<210> SEQ ID NO 139
<211> LENGTH: 44
<212> TYPE: DNA
<213> ORGANISM: artificial sequence
<220> FEATURE:

```
<223> OTHER INFORMATION: synthetic aptamer
<220> FEATURE:
<221> NAME/KEY: misc_feature
<223> OTHER INFORMATION: all adenosine are 2'-OH, except at positions 4,
      12 and 27, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 139
cggaccgaac aaggccugac uucuauacua agccuacguu ccgt                    44

<210> SEQ ID NO 140
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      12 and 30, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 140
cggaccgaac aaggccugac uucuauacua agccuacguu ccgt                    44

<210> SEQ ID NO 141
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      12 and 31, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
```

```
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 141
cggaccgaac aaggccugac uucuauacua agccuacguu ccgt                    44

<210> SEQ ID NO 142
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      12, and 36, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 142
cggaccgaac aaggccugac uucuauacua agccuacguu ccgt                    44

<210> SEQ ID NO 143
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      11, 12, and 36, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 143
cggaccgaac aaggccugac uucuauacua agccuacguu ccgt                    44
```

<210> SEQ ID NO 144
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH except at positions 4, 12, 19, 25, 27, and 31, wherein adenosine is 2'-O-methyl
<220> FEATURE:
<221> NAME/KEY: misc_feature
<223> OTHER INFORMATION: all guanosine are 2'-O-methyl, except at position 18, wherein guanosine is 2'-OH
<220> FEATURE:
<221> NAME/KEY: misc_feature
<223> OTHER INFORMATION: all cytidine are 2'-fluoro, except at positions 1, 15, 33, 34, 41 and 41, wherein cytidine is 2'-O-methyl
<220> FEATURE:
<221> NAME/KEY: misc_feature
<223> OTHER INFORMATION: all uridine are 2'-fluoro, except at positions 35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy thymidine (3'-3' linked)

<400> SEQUENCE: 144
cggaccgaac aaggccugac uucuauacua agccuacguu ccgt                    44

<210> SEQ ID NO 145
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-O-methyl, except at positions 8, 9, and 30, wherein adenosine is 2'-OH
<220> FEATURE:
<221> NAME/KEY: misc_feature
<223> OTHER INFORMATION: all guanosine are 2'-O-methyl, except at position 18, wherein guanosine is 2'-OH
<220> FEATURE:
<221> NAME/KEY: misc_feature
<223> OTHER INFORMATION: all cytidine are 2'-fluoro, except at positions 1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions 35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy thymidine (3'-3' linked)

<400> SEQUENCE: 145
cggaccgaac aaggccugac uucuauacua agccuacguu ccgt                    44

<210> SEQ ID NO 146
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4 and 12, wherein adenosine is 2'-O-methyl, and at position 8, wherein adenosine is deoxy

```
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 146
cggaccgaac aaggccugac uucuauacua agccuacguu ccgt                44

<210> SEQ ID NO 147
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4
      and 12, wherein adenosine is 2'-O-methyl, and at position 9,
      wherein adenosine is deoxy
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 147
cggaccgaac aaggccugac uucuauacua agccuacguu ccgt                44

<210> SEQ ID NO 148
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4
      and 12, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is deoxy
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
```

```
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 148
cggaccgaac aaggccugac uucuauacua agccuacguu ccgt                          44

<210> SEQ ID NO 149
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4
      and 12, wherein adenosine is 2'-O-methyl, and position 30, wherein
      adenosine is deoxy
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 149
cggaccgaac aaggccugac uucuauacua agccuacguu ccgt                          44

<210> SEQ ID NO 150
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4
      and 12, wherein adenosine is 2'-O-methyl, and at positions 8, 9,
      and 30, wherein adenosine is deoxy
<220> FEATURE:
<221> NAME/KEY: misc_feature
<223> OTHER INFORMATION: all guanosine are 2'-O-methyl, except at
      position 18, wherein guanosine is deoxy
<220> FEATURE:
<221> NAME/KEY: misc_feature
<223> OTHER INFORMATION: all cytidine are 2'-fluoro, except at positions
      1, 15, 33, 34, 41 and 42, wherein cytidine are 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 150
cggaccgaac aaggccugac uucuauacua agccuacguu ccgt                          44
```

```
<210> SEQ ID NO 151
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: thymidine at position 44 is an inverted deoxy
      thymidine (3'-3' linked)
<220> FEATURE:
<221> NAME/KEY: misc_feature
<223> OTHER INFORMATION: all adenosine are 2'-O-methyl, except at
      positions 9 and 30, wherein adensoine is 2'-OH, and position 8,
      wherein adenosine is deoxy
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl

<400> SEQUENCE: 151
cggaccgaac aaggccugac uucuauacua agccuacguu ccgt                      44

<210> SEQ ID NO 152
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-O-methyl, except at
      positions 8 and 30, wherein adenosine is 2'-OH, and position 9
      wherein adenosine is deoxy
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 152
cggaccgaac aaggccugac uucuauacua agccuacguu ccgt                      44

<210> SEQ ID NO 153
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-O-methyl, except at
      positions 8, 9 and 30, wherein adenosine is 2'-OH
<220> FEATURE:
<221> NAME/KEY: misc_feature
```

-continued

```
<223> OTHER INFORMATION: all guanosine are 2'-O-methyl, except at
      position 18, wherein guanosine is deoxy
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'O-methyl
<220> FEATURE:
<221> NAME/KEY: misc_feature
<223> OTHER INFORMATION: all uridine are 2'fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 153
cggaccgaac aaggccugac uucuauacua agccuacguu ccgt                   44

<210> SEQ ID NO 154
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-O-methyl, except at
      positions 8 and 9, wherein adenosine is 2'-OH, and position 30,
      wherein adenosine is deoxy
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'O-methyl
<220> FEATURE:
<221> NAME/KEY: misc_feature
<223> OTHER INFORMATION: all uridine are 2'-fluoro, except at positions
      35 and 40, wherein uridine is 2'O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 154
cggaccgaac aaggccugac uucuauacua agccuacguu ccgt                   44

<210> SEQ ID NO 155
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-O-methyl, except at
      positions 8, 9 and 30, wherein adenosine is deoxy
<220> FEATURE:
<221> NAME/KEY: misc_feature
<223> OTHER INFORMATION: all guanosine are 2'-O-methyl, except at
      position 18, wherein guanosine is deoxy
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
```

```
<222> LOCATION: (44)..(44)
<223> OTHER INFORMATION: thymidine at position 44 is an inverted deoxy
      thymidine (3'-3' linked)

<400> SEQUENCE: 155
cggaccgaac aaggccugac uucuauacua agccuacguu ccgt                    44

<210> SEQ ID NO 156
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      12, 25, 31, and 36, wherein adenosine is 2'O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 156
cggaccgaac aaggccugac uucuauacua agccuacguu ccgt                    44

<210> SEQ ID NO 157
<211> LENGTH: 43
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      12, 25, 31 and 36, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (1)..(1)
<223> OTHER INFORMATION: 2'-O-methyl cytidine at positions 1 is further
      modified by a 5' amine linker

<400> SEQUENCE: 157
cggaccgaac aaggccugac uucuauacua agccuacguu ccg                     43

<210> SEQ ID NO 158
<211> LENGTH: 44
<212> TYPE: DNA
<213> ORGANISM: artificial sequence
```

```
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      12, 25, 31 and 36, wherein adenosine is 2'-O-methyl
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O'methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (1)..(1)
<223> OTHER INFORMATION: 2'-O-methyl cytidine at position 1 is further
      modified by a 5'-amine linker
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 158
cggaccgaac aaggccugac uucuauacua agccuacguu ccgt                      44

<210> SEQ ID NO 159
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-OH, except at positions 4,
      12, 25, 31 and 36, wherein adenosine is 2'-O-methyl, and position
      8, wherein adenosine is deoxy
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 159
cggaccgaac aaggccugac uucuauacua agccuacguu ccgt                      44

<210> SEQ ID NO 160
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-O-methyl, except at
      position 9, wherein adenosine is 2'-OH, and positions 8 and 30,
      wherein adenosine is deoxy
```

```
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 160
cggaccgaac aaggccugac uucuauacua agccuacguu ccgt                    44

<210> SEQ ID NO 161
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-O-methyl, except at
      positions 8, 9 and 30, wherein adenosine is deoxy
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 161
cggaccgaac aaggccugac uucuauacua agccuacguu ccgt                    44

<210> SEQ ID NO 162
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-O-methyl, except at
      positions 8, 9 and 30, wherein adenosine is deoxy
<220> FEATURE:
<221> NAME/KEY: misc_feature
<223> OTHER INFORMATION: all guanosine are 2'-O-methyl, except at
      position 18, wherein guanosine is deoxy
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
```

```
<221> NAME/KEY: misc_feature
<222> LOCATION: (17)..(18)
<223> OTHER INFORMATION: 2'-fluoro uridine at position 17 is linked to
      deoxy guanosine at position 18 via a phosphorothioate
      internucleotide linkage
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 162
cggaccgaac aaggccugac uucuauacua agccuacguu ccgt                         44

<210> SEQ ID NO 163
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-O-methyl, except at
      positions 8, 9 and 30, wherein adenosine is deoxy
<220> FEATURE:
<221> NAME/KEY: misc_feature
<223> OTHER INFORMATION: all guanosine are 2'-O-methyl, except at
      position 18, wherein guanosine is deoxy
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
      35 and 40, wherein uridine is 2'-O-methyl
<220> FEATURE:
<221> NAME/KEY: misc_feature
<222> LOCATION: (1)..(1)
<223> OTHER INFORMATION: 2'-O-methyl cytidine at position 1 is further
      modified by a 5' amine linker
<220> FEATURE:
<221> NAME/KEY: misc_feature
<222> LOCATION: (17)..(18)
<223> OTHER INFORMATION: all 2'-fluoro uridine at position 17 is linked
      to deoxy guanosine at position 18 via a phosphorothioate
      internucleotide linkage
<220> FEATURE:
<221> NAME/KEY: misc_feature
<222> LOCATION: (44)..(44)
<223> OTHER INFORMATION: thymidine at position 44 is an inverted deoxy
      thymidine (3'-3' linked)

<400> SEQUENCE: 163
cggaccgaac aaggccugac uucuauacua agccuacguu ccgt                         44

<210> SEQ ID NO 164
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-O-methyl, except at
      positions 8, 9 and 30, wherein adenosine is deoxy
<220> FEATURE:
<221> NAME/KEY: misc_feature
<223> OTHER INFORMATION: all guanosine are 2'-O-methyl, except at
      position 18, wherein guanosine is 2'-OH
<220> FEATURE:
<221> NAME/KEY: misc_feature
<223> OTHER INFORMATION: all cytidine are 2'-fluoro, except at positions
      1, 15, 33, 34, 41 and 42, wherein cytidine is 2'-O-methyl
<220> FEATURE:
```

<221> NAME/KEY: misc_feature
<223> OTHER INFORMATION: all uridine are 2'-fluoro, except at positions
     35 and 40, wherein uridine is 2'-O-methyl
<220> FEATURE:
<221> NAME/KEY: misc_feature
<222> LOCATION: (8)..(8)
<223> OTHER INFORMATION: deoxy adenosine at position 8 is linked to
     deoxy adenosine at position 9 via a phosphorothioate
     internucleotide linkage
<220> FEATURE:
<221> NAME/KEY: misc_feature
<222> LOCATION: (44)..(44)
<223> OTHER INFORMATION: thymidine at position 44 is an inverted deoxy
     thymidine (3'-3' linked)

<400> SEQUENCE: 164
cggaccgaac aaggccugac uucuauacua agccuacguu ccgt                44

<210> SEQ ID NO 165
<211> LENGTH: 44
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: all adenosine are 2'-O-methyl, except at
     positions 8, 9 and 30, wherein adenosine deoxy
<220> FEATURE:
<221> NAME/KEY: misc_feature
<223> OTHER INFORMATION: all guanosine are 2'-O-methyl, except at
     position 18, wherein guanosine is deoxy
<220> FEATURE:
<221> NAME/KEY: misc_feature
<223> OTHER INFORMATION: all cytidine are 2'-fluoro, except at positions
     1, 15, 33, 34, 41 and 42, wherein cytidine is 2'-O-methyl
<220> FEATURE:
<221> NAME/KEY: misc_feature
<223> OTHER INFORMATION: all uridine are 2'-fluoro, except at positions
     35 and 40, wherein uridine is 2'-O-methyl
<220> FEATURE:
<221> NAME/KEY: misc_feature
<222> LOCATION: (8)..(9)
<223> OTHER INFORMATION: deoxy adenosine at position 8 is linked to
     deoxy adenosine at position 9 via a phopshorothioate
     internucleotide linkage
<220> FEATURE:
<221> NAME/KEY: misc_feature
<222> LOCATION: (17)..(18)
<223> OTHER INFORMATION: 2'-fluoro uridine at position 17 is linked to
     deoxy guanosine at position 18 via a phosphorothioate
     internucleotide linkage
<220> FEATURE:
<221> NAME/KEY: misc_feature
<222> LOCATION: (44)..(44)
<223> OTHER INFORMATION: thymidine at position 44 is an inverted deoxy
     thymidine (3'-3' linked)

<400> SEQUENCE: 165
cggaccgaac aaggccugac uucuauacua agccuacguu ccgt                44

<210> SEQ ID NO 166
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all adenosine are 2'-O-methyl, all guanosine
     are 2'-OH, and all cytidine and uridine are 2'-O-methyl

<400> SEQUENCE: 166

```
-continued cuacuacaca ugggucgggu gaguggcaaa ggaauaguag                  40

<210> SEQ ID NO 167
<211> LENGTH: 25
<212> TYPE: DNA
<213> ORGANISM: artificial sequence
<220> FEATURE:
<223> OTHER INFORMATION: synthetic aptamer

<400> SEQUENCE: 167
ctcatcggca gacgactcgc ccgau                                 25

<210> SEQ ID NO 168
<211> LENGTH: 70
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(70)
<223> OTHER INFORMATION: all purines (a and g) are 2'-OH, all
      pyrimidines (c and u) are 2'-fluoro

<400> SEQUENCE: 168
gggaggacga ugcggaccga aaaagaccug acuucuauac uaagucuacg uucccagacg  60
acucgcccga                                                        70
```